US010526408B2

(12) United States Patent
Georgiou et al.

(10) Patent No.: US 10,526,408 B2
(45) Date of Patent: Jan. 7, 2020

(54) ENGINEERED ANTIBODY FC VARIANTS

(71) Applicant: Research Development Foundation, Carson City, NV (US)

(72) Inventors: George Georgiou, Austin, TX (US); Chang-Han Lee, Austin, TX (US)

(73) Assignee: Research Development Foundation, Carson City, NV (US)

( * ) Notice: Subject to any disclaimer, the term of this patent is extended or adjusted under 35 U.S.C. 154(b) by 307 days.

(21) Appl. No.: 15/249,730

(22) Filed: Aug. 29, 2016

(65) Prior Publication Data
US 2017/0058030 A1 Mar. 2, 2017

Related U.S. Application Data

(60) Provisional application No. 62/211,147, filed on Aug. 28, 2015.

(51) Int. Cl.
*C07K 1/00* (2006.01)
*C07K 16/00* (2006.01)
*C12P 21/08* (2006.01)
*A61K 39/395* (2006.01)
*A61K 39/40* (2006.01)
*C07K 16/28* (2006.01)

(52) U.S. Cl.
CPC ............ *C07K 16/283* (2013.01); *C07K 16/00* (2013.01); *C07K 16/2887* (2013.01); *C07K 2317/14* (2013.01); *C07K 2317/41* (2013.01); *C07K 2317/524* (2013.01); *C07K 2317/70* (2013.01); *C07K 2317/75* (2013.01); *C07K 2317/92* (2013.01); *C07K 2319/30* (2013.01)

(58) Field of Classification Search
None
See application file for complete search history.

(56) References Cited

U.S. PATENT DOCUMENTS

| 6,737,056 | B1 * | 5/2004 | Presta ................ | C07K 16/4291 424/133.1 |
| 7,094,571 | B2 | 8/2006 | Harvey et al. | |
| 7,217,798 | B2 * | 5/2007 | Hinton ............... | C07K 14/5437 435/326 |
| 7,361,740 | B2 * | 4/2008 | Hinton .................. | C07K 16/00 530/387.3 |
| 7,419,783 | B2 | 9/2008 | Georgiou et al. | |
| 7,611,866 | B2 | 11/2009 | Georgiou et al. | |
| 8,043,621 | B2 | 10/2011 | Benhar et al. | |
| 2003/0219870 | A1 | 11/2003 | Georgiou et al. | |
| 2013/0058919 | A1 | 3/2013 | Lazar et al. | |
| 2014/0093496 | A1 | 4/2014 | Mimoto et al. | |
| 2015/0315284 | A1 | 11/2015 | Lazar et al. | |

FOREIGN PATENT DOCUMENTS

| EP | 2 679 681 | 1/2014 |
| WO | WO 2005/018572 | 3/2005 |
| WO | WO 2008/137475 | 11/2008 |
| WO | WO 2012/115241 | 8/2012 |

OTHER PUBLICATIONS

Barrington, R. A. et al., "B Lymphocyte Memory," *J. Exp. Med.* 196:1189-1199, 2002.
Bolland and Ravetch, "Inhibitory Pathways Triggered by ITIM-Containing Receptors," *Adv. Immunol.*, 72:149-177, 1999.
Borrok et al., "Revisiting the Role of Glycosylation in the Structure of Human IgG Fc," *ACS Chem. Biol.*, 7:1596-1602, 2012.
Boruchov et al., "Activating and inhibitory IgG Fc receptors on human DCs mediate opposing functions," *J. Clin. Invest.*, 115:2914-2923, 2005.
Daeron, "Fc Receptor Biology," *Annu. Rev. Immunol.*, 15:203-234, 1997.
Daugherty et al., "Development of an optimized expression system for the screening of antibody libraries displayed on the *Escherichia coli* surface," *Protein Eng.*, 12:613-621,1999.
Elvin et al., "Therapeutic antibodies: Market considerations, disease targets and bioprocessing," *Int. J. Pharm.*, 440:83-98, 2013.
Fromant et al., "Direct random mutagenesis of gene-sized DNA fragments using polymerase chain reaction," *Anal. Biochem.*, 224:347-353, 1995.
Gaboriaud et al., "The Crystal Structure of the Globular Head of Complement Protein C1q Provides a Basis for Its Versatile Recognition Properties," *J. Biol. Chem.*, 278:46974-46982, 2003.
Harvey et al., "Anchored periplasmic expression, a versatile technology for the isolation of high-affinity antibodies from *Escherichia coli*-expressed libraries," *Proc. Natl. Acad. Sci. USA*, 101:9193-9198, 2004.
Harvey et al., "Engineering of recombinant antibody fragments to methamphetamine by anchored periplasmic expression," *J. Immunol. Methods.* 308:43-52, 2006.
International Search Report and Written Opinion issued in corresponding PCT Application No. PCT/US2016/049214, dated Mar. 1, 2017.
Jefferis, "Glycosylation of Natural and Recombinant Antibody Molecules," *Adv. Exp. Med. Biol.*, 564:143-148, 2005.
Jefferis, "Glycosylation of Recombinant Antibody Therapeutics," *Biotechnol. Prog.*, 21:11-16, 2005.
Jung et al., "Aglycosylated IgG variants expressed in bacteria that selectively bind Fc gamma RI potentiate tumor cell killing by monocyte-dendritic cells," *Proc. Natl. Acad. Sci., USA*, 107(2):604-609, 2010.

(Continued)

*Primary Examiner* — Chun W Dahle
(74) *Attorney, Agent, or Firm* — Parker Highlander PLLC

(57) ABSTRACT

In some aspects, mutant or variant Fc domains are provided that can exhibit increased affinity or selectivity for FcγRIIB. The variant Fc domain may be a mutant IgG1 Fc domain. In some embodiments, a mutant or variant Fc domain may be present in a therapeutic antibody such as, e.g., an agonistic antibody. Additional methods for using and identifying mutant Fc domains are also provided.

23 Claims, 30 Drawing Sheets

Specification includes a Sequence Listing.

(56) References Cited

OTHER PUBLICATIONS

Jung et al., "Effective Phagocytosis of Low Her2 Tumor Cell Lines with Engineered, Aglycosylated IgG Displaying High Fc[gamma]RIIa Affinity and Selectivity," *ACS Chem. Biol.*, 8(2):368-375, 2013.

Jung et al., "Engineering an aglycosylated Fc variant for enhanced Fc[gamma]RI engagement and pH-dependent human FcRn binding," *Biotechnol. Bioprocess Engineer.*, 19(5):780-789, 2014.

Kalergis and Ravetch, "Inducing Tumor Immunity through the SelectiveEngagement of Activating Fc Receptors on Dendritic Cells," *J. Exp. Med.*, 195:1653-1659, 2002.

Kelton et al., "IgGA: A "Cross-Isotype" Engineered Human Fc Antibody Domain that Displays Both IgG-like and IgA-like Effector Functions," *Chemistry & Biology*, 21(12): 1603-1609, 2014.

Lanio and Jeltsch, "PCR-Based Random Mutagenesis Method Using Spiked Oligonucleotides to Randomize Selected Parts of a Gene without any Wild-Type Background," *Biotechniques*, 25:962-955, 1998.

Leysath et al., "Crystal Structure of the Engineered Neutralizing Antibody M18 Complexed to Domain 4 of the Anthrax Protective Antigen," *J. Mol. Biol.*, 387:680-693, 2009.

Mimoto et al., "Engineered antibody Fc variant with selectively enhanced Fc RIIb binding over both Fc RIIaR131 and Fc RIIaH131," *Protein Engineer. Design Select.*, 26(10):589-598, 2013.

Nimmerjahn F. and Ravetch JV, "Divergent Immunoglobulin G Subclass Activity Through Selective Fc Receptor Binding," *Science*. 310(5753):1510-1512, 2005.

Qin, D. et al. "Fc[gamma] Receptor IIB on Follicular Dendritic Cells Regulates the B Cell Recall Response," *J. Immunol.* 164, 6268-6275, 2000.

Wilson et al., "An Fcγ Receptor-Dependent Mechanism Drives Antibody-Mediated Target-Receptor Signaling in Cancer Cells," *Cancer Cell*, 19(1):101-113, 2011.

\* cited by examiner pBAD30-Trastuzumab Light Chain pMopac12-Trastuzumab Heavy Chain

```
            235           245           255           265           275           285           295
            |             |             |             |             |             |             |
IgG1 Fc  CPPCPAPELLGGPSVFLFPPKPKDTLMISRTPEVTCVVVDVSHEDPEVKFNWYVDGVEVHNAKTKPREEQ
B13      ......................................................................
B21      ...........REE.R......................................................
B25      ......................................................................
Bn2      .........................................A............................
Bn15     ......................................................................
Bn17     ..............Q..........................A............................
Bn20     ..............Q..........................A............................
Bn22     .........................................A............................
Bn28     ......................................................................
Bn31     ........................................................A.............
Bn31     ........................................................A.............
```

FIG. 19

|       | 305        | 315        | 325        | 335        | 345        | 355        | 365   |
|-------|------------|------------|------------|------------|------------|------------|-------|
| IgG1 Fc | YNSTYRVVSV | LTVLHQDWLNGKEYKCKVSN | KALPAPIEKTISKAKGQPREPQVYTLPPSRDELTKNQVSL |
| B13   | . . . . . . . . . . | . . . . . . . . . . | . . . . . . . . . . | . . . . . . . . . . | . . . . . . . . . . | . . . . . . . . . . | . . . . . |
| B21   | . . . . . . . . . . | . . . . K . . . . . | . . . . . . . . . . | S C W . . . . . . . | . . . . . . . . . . | . . Q . . . . . . . | . . . . . |
| B25   | . L . . . . . . . . | . . . . . . . . . . | . . . . . . . . . . | . N G . V . . . . . | . . . . . . . . . . | . . . . . . . . . . | . . . . . |
| Bn2   | . . . . . . . . . . | . . . . . . . . . . | . . . . . . . . . . | . . . . . . . . . . | . . . . . . . . . . | . . Q . . . . . . . | . . . . . |
| Bn15  | C . . . . . . . . . | . . . . . . . . . . | . . . . . . . . . . | . . . . . . . . . . | . . . . . . . . . . | . . . . . . . . . . | . . . . . |
| Bn17  | . . . . . . . . . . | . . . S . . . . . . | . . . . . . . . . . | . M . . . R . D . . | . . . . . . . . . . | . . . . . . . . . . | . . . . . |
| Bn20  | . . . . . . . . . . | . . . . . . . . . . | . . . . . . . . . . | . . . . . . . . . . | . . . . . . . . . . | . . Q . . . . . . . | . . . . . |
| Bn22  | . . . . . . . . . . | . . . . . . . . . . | . . . . . . . . . . | . . . . . . . . . . | . . . . . . . . . . | . . . . . . . . . . | . . . . . |
| Bn28  | C Q . . . . . . . . | . . . . K . . . . . | . . . . . . . . . . | . . . . . . . . . . | . . . . . Q . . . . | . . Q . . . . . . . | . . . . . |
| Bn31  | . Q . . . . . . . . | . . . . . . . . . . | . . . . . . . . . . | . . . . . . . . . . | . . . . . . . . . . | . . . . . . . . . . | . . . . . |

Sequence alignment (positions 375–435):

```
              375         385         395         405         415         425         435
              |           |           |           |           |           |           |
IgG1 Fc  TCLVKGFYPSDIAVEWESNGQPENNYKTTPPVLDSDGSFFLYSKLTVDKSRWQQGNVFSCSVMHEALHNH
B13      .....................................................................
B21      .....................................................................
B25      .....................................................................
Bn2      ...........................R................F.M......................
Bn15     ...........................R..........................................
Bn17     ......T....................R...........................................
Bn20     ...........................R.......................................R..
Bn22     ...........................R................S.M......................
Bn28     ..............................................S.M.....................
Bn31     ....................................................................R..
```

(Dots indicate identity with the IgG1 Fc reference sequence; letters indicate amino acid substitutions at the corresponding positions.)

```
                              445
                              |
IgG1 Fc  . . . . Y T Q K S L S L S P G K  . .
B13      . . . . . . . . . . . . . . . .  . .
B21      . . . . . . . . . . . . . . . .  . .
B25      . . . . . . . . . . . . . . . .  . .
Bn2      . . . . . . . . . . . . . . . .  . .
Bn15     . . . . . . . . . . . . . . . .  . .
Bn17     . . . . . . . . . . . . . . . .  . .
Bn20     . . . . . . . . . . . . . . . .  . .
Bn22     . . . . . . . . . . . . . . . .  . .
Bn28     . . . . . . . . . . . . . . . .  . .
Bn31     . . . . . . . . . . . . . . . .  . .
```

ENGINEERED ANTIBODY FC VARIANTS

This application claims the benefit of U.S. Provisional Patent Application No. 62/211,147 filed Aug. 28, 2015, the entirety of which is incorporated herein by reference.

BACKGROUND OF THE INVENTION

1. Field of the Invention

The present invention relates generally to the field of protein engineering. More particularly, it concerns improved compositions of Fc antibody domains conferring high binding to FcγRIIB and altered effector function.

2. Description of Related Art

Currently, the top 25 marketed recombinant therapeutic antibodies have sales of well over $43.5 billion/year, and with a forecasted annual growth rate of 9.2% from 2010 to 2015, they are projected to increase to $62.7 billion/year by 2015 (J. G. Elvin et al., 2013). Monoclonal antibodies (mAbs) comprise the majority of recombinant proteins currently in the clinic, with 1064 products undergoing company-sponsored clinical trials in the USA or EU, of which 164 are phase III (Elvin et al., 2013). In terms of therapeutic focus, the mAb market is heavily focused on oncology and inflammatory disorders, and products within these therapeutic areas are set to continue to be the key growth drivers over the forecast period. As a group, genetically engineered mAbs generally have a higher probability of FDA approval success than small-molecule drugs. At least 50 biotechnology companies and all major pharmaceutical companies have active antibody discovery programs in place. The original method for isolation and production of mAbs was first reported at 1975 by Milstein and Kohler (Kohler and Milstein, 1975), and it involved the fusion of mouse lymphocyte and myeloma cells, yielding mouse hybridomas. Therapeutic murine mAbs entered clinical study in the early 1980s; however, problems with lack of efficacy and rapid clearance due to patients' production of human anti-mouse antibodies (HAMA) became apparent. These issues, as well as the time and cost consumption related to the technology, became driving forces for the evolution of mAb production technology. Polymerase Chain Reaction (PCR) facilitated the cloning of monoclonal antibody genes directly from lymphocytes of immunized animals and the expression of combinatorial libraries of antibody fragments in bacteria (Orlandi et al., 1989). Later libraries were created entirely by in vitro cloning techniques using naive genes with rearranged complementarity determining region 3 (CDR3) (Griffiths and Duncan, 1998; Hoogenboom et al., 1998). As a result, the isolation of antibody fragments with the desired specificity was no longer dependent on the immunogenicity of the corresponding antigen. These advantages have facilitated the development of antibody fragments to a number of unique antigens including small molecular compounds (haptens) (Hoogenboom and Winter, 1992), molecular complexes (Chames et al., 2000), unstable compounds (Kjaer et al., 1998), and cell surface proteins (Desai et al., 1998).

One method for screening large combinatorial libraries of antibodies to identify clones that bind to a ligand with desired affinity involves expression and display of antibody fragments or full length antibodies on the surface of bacterial cells and more specifically *E. coli*. Cells displaying antibodies or antibody fragments are incubated with a solution of fluorescently labeled ligand and those cells that bind said ligand by virtue of the displayed antibody on their surface are isolated by flow cytometry. In particular, Anchored Periplasmic Expression (APEx) is based on anchoring the antibody fragment on the periplasmic face of the inner membrane of *E. coli* followed by disruption of the outer membrane, incubation with fluorescently-labeled target, and sorting of the spheroplasts (U.S. Pat. No. 7,094,571, Harvey et al., 2004; Harvey et al., 2006).

The receptors for Fc domain of antibodies are expressed on diverse immune cells and are important in both promoting and regulating the immunological response to antibody antigen complexes (called immune complexes). The binding of the Fc region of antibodies that have formed immune complexes with a pathogenic target cell to different Fc receptors expressed on the surface of leukocytes to elicit antibody-dependent cell cytotoxicity (ADCC) and antibody-dependent cell phagocytosis (ADCP) or complement-mediated reactions including complement dependent cytotoxicity (CDC).

In humans there are two general classes of FcγRs for IgG class antibodies: activating receptors, characterized by the presence of a cytoplasmic immunoreceptor tyrosine-based activation motif (ITAM) sequence associated with the receptor, and the inhibitory receptor, characterized by the presence of an immunoreceptor tyrosine-based inhibitory motif (ITIM) sequence (Daeron M, 1997 and Bolland S et al., 1999). Of note, activating FcγRs, FcγRI, FcγRIIA, FcγRIIIA, FcγRIIIB induce activating or pro-inflammatory responses, while inhibitory FcγRIIB induces anti-inflammatory or inhibitory responses. Among activating FcγRs, FcγRIIA and FcγRIIIA have natural allotypes which can affect binding capacity of IgG. FcγRIIA$_{H131}$ showed higher binding affinity than FcγRIIA$_{R131}$ for IgG and FcγRIIIA$_{V158}$ showed higher binding affinity than FcγRIIIA$_{F158}$ for IgG. All naturally produced antibodies and also recombinant glycosylated antibodies produced by tissue culture contain Fc domains that bind to both the activating and the inhibitory FcγRs. (Boruchov et al. 2005; Kalergis et al., 2002).

As mentioned above, aglycosylated antibodies do not display any detectable binding to FcγRIIB. Due to the physiological importance of Fc binding to FcγRIIB and the importance of Fc binding to FcγRIIB with therapeutic antibodies (e.g., agonistic antibodies), there is a clear need for new Fc domains, and in particular aglycosylated Fc domains, that can selectively bind FcγRIIB.

SUMMARY OF THE INVENTION

In some aspects, the present invention overcomes limitations in the prior art by providing aglycosylated Fc domain variants which display increased affinity and selectivity for FcγRIIB. As shown in the below examples, the inventors have succeeded in not only providing engineered aglycosylated IgG1 Fc domains that bind to FcγRIIB with affinities far exceeding that of wild-type, authentic human IgG1, for FcγRIIB, but in some aspects the aglycosylated Fc domains were further observed to have very low to negligible or undetectable binding to other Fcγ receptors (e.g., activating Fcγ receptors). In some embodiments and as shown in the below examples, the engineered FcγRIIB mutants may also result in increased expression. Such high selectivity is very desirable for many therapeutic applications where inflammatory effects mediated by antibodies due to the binding of activating FcγRs or complement need to be avoided.

In some aspects of the present invention, methods are provided for isolating aglycosylated antibody Fc domains that display increased affinity and selectivity for FcγRIIB. In another aspect of the present invention, specific mutations and combinations of mutations in IgG1 Fc domains are provided that can result in selective binding and/or increased affinity to FcγRIIB.

More specifically, in some embodiments, mutant or variant Fc domains are provided that, as compared to a corresponding wild-type Fc domain, exhibit: (i) enhanced binding for FcγRIIB and (ii) reduced binding or no detectable finding to activating Fcγ receptors (e.g., human FcγRI, FcγRIIa H131, FcγRIIa R131, FcγRIIIa F158, or FcγRIIIa V158). The mutant or variant Fc domain may be a mutant or variant IgG domain. In some preferred embodiments, the mutant or variant Fc domains are human mutant or variant Fc domains. The mutant or variant Fc domain may be comprised in a polypeptide, such as an antibody. In some embodiments, the mutant or variant Fc domain may be comprised in a therapeutic antibody such as, e.g., an agonistic antibody. In some embodiments, there are compositions involving a polypeptide that has an aglycosylated Fc domain from a human IgG1 antibody ("antibody Fc domain"). In additional embodiments, the aglycosylated Fc domain is a variant of the human IgG1 Fc domain (SEQ ID NO: 1) that enables highly selective binding only to FcγRIIIB and not to any of the effector Fc receptors namely FcγRI, FcγRIIA, and FcγRIIIA. In other embodiments, an engineered Fc domain binds highly selectively to FcγRIIIB and displays little or no binding to effector Fc receptors, both when it is expressed in aglycosylated form. In additional embodiments, engineered Fc domains display increased affinity for FcγRIIIB, e.g., from about 13.7 to about 224.9-fold of a polypeptide having a glycosylated wild-type Fc domain. In some embodiments, the mutant human Fc domains that selectively bind FcγRIIIB can also result in increased expression in mammalian cells.

An aspect of the present invention relates to a polypeptide comprising an aglycosylated mutant or variant human IgG Fc domain capable of binding human FcγRIIb; and at least one of: (i) substitution mutations of arginine at position 234 (L234R), glutamic acid at position 235 (L235E), glutamic acid at position 236 (G236E), arginine at position 238 (P238R), and glutamine at position 351 (L351Q); (ii) substitution mutations of glutamine at position 246 (K246Q), alanine at position 260 (T260A); glutamine at position (L351Q), arginine at position 386 (Q386R); phenylalanine at position 396 (P396F), and methionine at position 397 (V397M); (iii) substitution mutations of alanine at amino acid 264 (V264A), serine at amino acid 328 (L328S), cysteine at amino acid 329 (P329C), tryptophan at amino acid 330 (A330W), asparagine at amino acid 332 (I332N), glycine at position 333 (E333G), and valine at amino acid position 336 (I336V); or (iv) substitution mutations at the positions of an engineered Fc domain of Table 1. In some embodiments, the Fc domain has substitution mutations of arginine at position 234 (L234R), glutamic acid at position 235 (L235E), glutamic acid at position 236 (G236E), arginine at position 238 (P238R), and glutamine at position 351 (L351Q). The Fc domain may comprise or consist of the sequence of B21 or SEQ ID NO: 7. In some embodiments, the Fc domain has substitution mutations of glutamine at position 246 (K246Q), alanine at position 260 (T260A); glutamine at position (L351Q), arginine at position 386 (Q386R); phenylalanine at position 396 (P396F), and methionine at position 397 (V397M). The Fc domain may comprise or consist of the sequence of Bn2 or SEQ ID NO:9. In some embodiments, the Fc domain has substitution mutations of alanine at amino acid 264 (V264A), serine at amino acid 328 (L328S), cysteine at amino acid 329 (P329C), tryptophan at amino acid 330 (A330W), asparagine at amino acid 332 (I332N), glycine at position 333 (E333G), and valine at amino acid position 336 (I336V). The Fc domain may comprise or consist of the sequence of B13 or SEQ ID NO: 6. In some aspects, the present invention relates to a polypeptide comprising an aglycosylated mutant or variant human IgG Fc domain capable of binding human FcγRIIb; wherein the Fc domain comprises at least one of: (i) substitution mutations at Fc domain amino acids V264, L328, P329, A330, I332, E333, and I336; (ii) substitution mutations at Fc domain amino acids L234, L235, G236, P238, and L351; (iii) substitution mutation at Fc domain amino acid 311; (iv) substitution mutations at 2, 3, 4, 5, 6, 7, 8, 9, 10, 11, 12, or all of Fc domain amino acids E233, L234, L235, G236, G237, P238, T307, L328, P329, A330, P331, I332, and/or L351; or (v) substitution mutations at the positions of an engineered Fc domain of Table 1. In some embodiments, the aglycosylated mutant or variant human IgG Fc domain comprises a substitution mutation at 1, 2, 3, 4, 5, 6, 7, 8, 9, 10, or all of Fc domain amino acids Q386, V397, P396, P396, V397, K246, V264, N297, L351, T260, and/or Y296; for example, the aglycosylated mutant or variant human IgG Fc domain may comprise 1, 2, 3, 4, 5, 6, 7, 8, 9, 10, or all of substitution mutations at Fc domain amino acids Q386R, V397M, P396S, P396F, V397M, K246Q, V264A, N297Q, L351Q, T260A, and/or Y296C. In some embodiments, the Fc domain does not selectively or detectably bind to a human FcγRI, FcγRIIa H131, FcγRIIa R131, FcγRIIIa F158, and/or FcγRIIIa V158 polypeptide. In some embodiments, the Fc domain does not selectively or detectably bind to a human FcγRI. In some embodiments, the Fc domain does not detectably bind to human FcγRIIa H131, FcγRIIa R131, FcγRIIIa F158, and FcγRIIIa V158. The Fc domain may comprise a substitution mutation at amino acid 299 such as, e.g., a leucine at amino acid position 299 (T299L). In some embodiments, the Fc domain comprises the substitution mutations of alanine at amino acid 264 (V264A), serine at amino acid 328 (L328S), cysteine at amino acid 329 (P329C), tryptophan at amino acid 330 (A330W), asparagine at amino acid 332 (I332N), glycine at position 333 (E333G), and valine at amino acid position 336 (I336V). The Fc domain may comprise or consist of the sequence of B13, with the T299L mutation (SEQ ID NO: 2) or without it (SEQ ID NO: 6). In some embodiments, the Fc domain comprises the substitution mutations of arginine at position 234 (L234R), glutamic acid at position 235 (L235E), glutamic acid at position 236 (G236E), arginine at position 238 (P238R), and glutamine at position 351 (L351Q). The Fc domain may comprise or consist of the sequence of B21, with the T299L mutation (SEQ ID NO: 3) or without it (SEQ ID NO: 7). In some embodiments, the Fc domain comprises the substitution mutations of threonine at position 299 (T299L) and glutamine at position 311 (Q311K). The Fc domain may comprise or consist of the sequence of B25, with the T299L mutation (SEQ ID NO: 4) or without it (SEQ ID NO: 8). The Fc domain may comprise or consist of the sequence of Bn2, with the T299L mutation (SEQ ID NO: 5) or without it (SEQ ID NO: 9). In some embodiments, the Fc domain has the substitution mutations of an engineered Fc domain of Table 1. In some embodiments, The Fc domain binds FcγRIIB with an equilibrium constand of less than about 1M and does not display detectable binding to FcγRI, FcγRIIa H131, FcγRIIa R131, FcγRIIIa F158, and FcγRIIIa V158. The polypeptide may further comprise a non-Fc receptor (non-FcR) binding domain. The non-FcR binding domain may be an Ig variable domain. In some embodiments, the polypeptide is a full-length antibody. The antibody may be an agonistic antibody. In some embodiments, the antibody selectively binds CD20, CD40, IL-10, or 4-1BB. The antibody may be chemically conjugated to or covalently bound to a toxin. In some embodiments, the non-FcR binding region is not an antigen binding site of an antibody. The non-FcR binding region may bind a cell-surface protein or a soluble protein.

Another aspect of the present invention involves a nucleic acid encoding any of the polypeptides of the present invention, e.g., as described above or herein. The nucleic acid may be a DNA segment. In some embodiments, the nucleic acid is an expression vector.

Yet another aspect of the presented invention relates to a host cell comprising the nucleic acid of the present invention, e.g., as described above or herein. In some embodiments, said cell expresses said nucleic acid.

Another aspect of the present invention relates to a method for preparing an aglycosylated polypeptide comprising: a) obtaining a host cell in accordance with claim 28; b) incubating the host cell in culture under conditions to promote expression of the aglycosylated polypeptide; and c) purifying the expressed polypeptide from the host cell. In some embodiments, the host cell is a eukaryotic cell and the polypeptide further comprises a leucine substitution at amino acid 299 (T299L). In some embodiments, the host cell is a prokaryotic cell.

Yet another aspect of the present invention relates to a pharmaceutical formulation comprising a polypeptide of the present invention (e.g., as described above), or the nucleic acid of the present invention (e.g., as described above) in a pharmaceutically acceptable carrier.

Another aspect of the present invention relates to a method of binding a protein in a subject comprising providing to the subject an antibody, wherein the antibody is aglycosylated, binds the protein, and comprises an Fc domain of the present invention. In some embodiments, the aglycosylated antibody is capable of specifically binding human FcγRIIb, and wherein the aglycosylated antibody has a reduced binding of one or more activating Fcγ receptors as compared to a human wild-type IgG Fc domain. The aglycosylated antibody may be capable of specifically binding a human FcγRI. In some embodiments, the aglycosylated antibody is capable of specifically binding an activating human Fcγ receptor polypeptide at a level that is at least 50-fold less than a glycosylated, wild-type version of the antibody. In some embodiments, the aglycosylated antibody does not specifically bind an activating human Fcγ receptor polypeptide such as, e.g., FcγRI, FcγRIIa H131, FcγRIIa R131, FcγRIIIa F158, or FcγRIIIa V158. In some embodiments, the antibody is an aglycosylated version of a therapeutic antibody.

Yet another aspect of the present invention relates to a method of treating a subject having a disease comprising administering to the subject an effective amount of a pharmaceutical formulation comprising a polypeptide of the present invention, or a nucleic acid of the present invention in a pharmaceutically acceptable carrier. In some embodiments, the method does not induce antibody-dependent cytotoxicity. The disease may be a cancer, an infection, or an autoimmune disease. In some embodiments, the subject is a human patient. The formulation may be administered intratumorally, intravenously, intradermally, intraarterially, intraperitoneally, intralesionally, intracranially, intraarticularly, intraprostaticaly, intrapleurally, intratracheally, intraocularly, intranasally, intravitreally, intravaginally, intrarectally, intramuscularly, subcutaneously, subconjunctival, intravesicularlly, mucosally, intrapericardially, intraumbilically, orally, by inhalation, by injection, by infusion, by continuous infusion, by localized perfusion bathing target cells directly, via a catheter, or via a lavage. In some embodiments, the disease is a cancer, and wherein the method further comprises administering at least a second anticancer therapy to the subject. The second anticancer therapy may be a surgical therapy, chemotherapy, radiation therapy, cryotherapy, hormone therapy, immunotherapy or cytokine therapy.

Another aspect of the present invention relates to a polypeptide of the present invention (e.g., as described above) for use in the treatment of disease. The disease may be a cancer, an infection, or an autoimmune disease. In some embodiments, the disease is a bacterial infection or a viral infection.

Yet another aspect of the present invention relates to the use of a polypeptide of the present invention in the preparation of a medicament for the treatment of a disease such as a cancer, infection, bacterial infection, viral infection, or an autoimmune disease.

Another aspect of the present invention relates to a pharmaceutically acceptable composition comprising a polypeptide of the present invention and a pharmaceutically acceptable excipient.

Yet another aspect of the present invention relates to a composition for use in a method of treating a disease in a subject in need thereof, said composition comprising a polypeptide of the present invention. In some embodiments, said disease is a cancer, an infection, a bacterial infection, a viral infection, or an autoimmune disease.

In some aspects, engineered mouse Fc domains that selectively bind mouse FcγRII and not to other mouse Fcγ receptors are provided. The mouse FcγRII is the functional equivalent of the human FcγRIIIB. Mouse engineered Fc domains selective for mouse FcRII may specifically trigger anti-inflammatory responses via phosphorylation of the ITIM domain in FcRII. Mouse Fc domains selective for the mouse FcRII receptor can be useful, e.g., for mechanistic studies.

In some aspects, methods are provided for isolating aglycosylated antibody Fc domains that display increased affinity and selectivity for FcγRIIB. The aglycosylated antibody Fc domains may comprise one or more or the specific substitution mutations or combinations of substitution mutations as described herein, e.g., to affect binding or selectively and with increased affinity of the Fc domain to FcγRIIB.

In some embodiments, there are compositions involving a polypeptide that has an aglycosylated Fc domain from a human IgG1 antibody ("antibody Fc domain"). In additional embodiments, the aglycosylated Fc domain is a variant of the human IgG1 Fc domain (SEQ ID NO: 1) that can display (i) increased or selective binding to FcγRIIIB and (ii) reduced or no detectable binding to any of the effector Fc receptors: FcγRI, FcγRIIA, and FcγRIIIA. In some embodiments, the engineered Fc domain, when it is expressed in aglycosylated form, both (i) binds selectively to FcγRIIIB and (ii) displays little or no binding to effector Fc receptors. In additional embodiments engineered Fc domains display increased affinity for FcγRIIIB between within 13.7 to 224.9-fold of a polypeptide having a glycosylated wild-type Fc domain.

An antibody Fc domain may be the Fc domain of an IgG antibody or a variant thereof. Furthermore, the antibody Fc domain may be defined as a human Fc domain. In certain aspects, the Fc domain may be an IgG1 Fc domain, such as the Fc domain of an anti-HER2 antibody, more specifically, the Fc domain of trastuzumab and the Fc domain of an anti-CD20 antibody, more specifically, the Fc domain of rituximab. It is also contemplated that a polypeptide may comprise a fusion of an engineered Fc domain as disclosed herein fused to a polypeptide not derived from an antibody molecule.

In some embodiments, a polypeptide comprising an aglycosylated antibody Fc domain comprises particular amino acid substitutions. In some embodiments there are multiple amino acid substitutions at one of more positions from the following list: (264, 328, 329, 330, 332, 333) and (336; 234, 235, 236, 238), and (351; 311); in some embodiments, the engineered Fc domain may have a substitution mutation at 2, 3, 4, 5, 6, 7, 8, 9, 10, 11, 12, or all of these positions.

In some cases it is contemplated that the antibodies also have a substitution at amino acid 297 or 299 that impairs N-linked glycosylation when the antibody is expressed in mammalian cells that recognize the glycosylation motif in the antibody Fc domain. It is anticipated that any mutation in amino acid 297 or 299 known to abolish glycosylation can be used (e.g., WO2005018572A2) can be employed including, e.g., replacement of 299T by a leucine residue.

In other preferred embodiments an aglycosylated antibody Fc domains may a substitution at amino acid 264 to alanine (V264A), a substitution at amino acid 328 by serine (L328S), a substitution at amino acid 329 to cysteine (P329C), a substitution at amino acid 330 to tryptophan (A330W), a substitution at amino acid 332 to asparagine (I332N), a substitution at amino acid 333 to glycine (E333G), a the substitution at amino acid 336 to valine (I336V) or combinations of these substitutions thereof.

In some embodiments, an engineered IgG Fc domain may comprise one or more additional amino acid substitutions. For example, the engineered Fc domain may further comprise one or more substitution(s) at amino acid 234, 235, 236, 238, and 351; and in some preferred embodiments, the substitution at amino acid 234 is arginine (L234R), the substitution at amino acid 235 is glutamate (L235E), the substitution at amino acid 236 is glutamate (G236E), the substitution at amino acid 238 is arginine (P238R), and the substitution at amino acid 351 is glutamine (L351Q). In some embodiments, the engineered Fc domain contains an additional amino acid substitutions at residue 311 such as, e.g., lysine (i.e., Q311K) in some preferred embodiments.

In some aspects, various combinations of substitution mutations may be present in a mutant or variant Fc domain of the present invention. The mutant or variant human IgG Fc domain may comprise 1, 2, 3, or 4 of: substitution mutations of alanine at amino acid 264 (V264A), cysteine at amino acid 329 (P329C), glycine at position 333 (E333G), and valine at amino acid position 336 (I336V); optionally in combination with 1, 2, or 3 of: tryptophan at amino acid 330 (A330W), asparagine at amino acid 332 (I332N), and serine at amino acid 328 (L328S); optionally in combination with threonine at position 299 (T299L). In some embodiments, the variant Fc domain may comprise 1, 2, 3, 4, 5, 6, or all of: V264A, L328S, P329C, A330W, I332N, E333G, I336V mutations, optionally in combination with a mutation at position 299 such as T299L. In some embodiments, the variant Fc domain may comprise 1, 2, 3, 4, 5, or all of: L234R, L235E, G236E, P238R, T299L, L351Q mutations. In some embodiments, the variant Fc domain comprises the Q311K mutation, optionally in combination with T299L mutation.

A variant Fc domain polypeptide (also referred to as a mutant or engineered Fc domain) may be characterized as having a certain percentage of identity as compared to an unmodified polypeptide (e.g., a wild-type Fc domain polypeptide, such as a wild-type IgG Fc domain, or a human wild-type IgG Fc domain) or to any polypeptide sequence disclosed herein. The percentage identity may be about, at least 60%, 65%, 70%, 75%, 80%, 85%, 90%, 95%, 96%, 97%, 98%, 99%, 99.5%, or 100% (or any range derivable therein) between the unmodified portions of a modified polypeptide (i.e., the sequence of the modified polypeptide excluding any specified substitutions) and the corresponding wild-type polypeptide. For example, a variant Fc domain may have, e.g., at least 90% (or at least about 95%, etc.) sequence identity as compared to a wild-type Fc domain (e.g., a wild-type human Fc domain) for regions of the variant Fc domain excluding specified substitution mutations (e.g., a substitution mutation at position 299 (e.g., T299L), in addition to any other specified substitution mutation(s)). The variant Fc domain may contain additional mutations, as compared to a wild-type Fc domain, in addition to the specified substitution mutations in the mutant Fc domain. It is also contemplated that percentage of identity discussed above may relate to the entirety of a variant Fc domain polypeptide as compared to a wild-type Fc domain (e.g., a human IgG Fc domain). For example, a variant Fc domain polypeptide characterized as having at least 90% identity to a wild-type Fc domain means that at least 90% of the amino acids in that variant polypeptide are identical to the amino acids in the wild-type polypeptide.

An antibody Fc domain may be an Fc domain of a human IgG antibody or a variant thereof. In certain aspects, the Fc domain may be an IgG1 Fc domain. It is also contemplated that a polypeptide may comprise a fusion of an engineered variant Fc domain as disclosed herein fused to a polypeptide not derived from an antibody molecule. In some embodiments, an engineered Fc domain of the present invention is comprised in an agonistic antibody such as, e.g., an antibody targeting CD40, death receptor 5 (DR5), or a TNF receptor (TNFR) molecule.

Polypeptides comprising a variant Fc domain described herein may include a linker in some embodiments. In further embodiments, the linker is a conjugatable linker. In some embodiments, the polypeptide contains an Fc domain from an antibody. It may contain other regions from an antibody, such as another binding domain. The additional binding domain may not be not an FcR binding domain in some embodiments. In some embodiments, the polypeptide may contain an antigen binding site or domain from an antibody, such as all or part of the variable region from an antibody. The polypeptide may contain an Fc domain from an antibody and another binding domain that is a non-FcR binding domain. In some embodiments, the non-Fc binding region is not an antigen binding site of an antibody but specifically binds a cell-surface protein or a soluble protein. In some cases, a cell-surface protein that the non-Fc binding region recognizes is a receptor, such as, e.g., a receptor expressed on a cell surface.

Other polypeptides include those having an aglycosylated variant Fc domain (e.g., capable of binding a FcγRIIb polypeptide while exhibiting reduced binding to an activating FcR) and a second binding domain that is a non-Fc receptor binding domain, wherein the second binding domain is capable of specifically binding a cell-surface molecule or a soluble protein. In some embodiments, the second binding domain is an antigen binding domain of an antibody ("Ig variable domain"). In some aspects, the polypeptide may be a full-length antibody. In some cases, the second binding domain is not an antibody antigen binding domain. In some embodiments, the second binding domain is capable of specifically binding a cell-surface molecule that is a protein or proteinaceous molecule. In some aspects, the second binding domain is capable of specifically binding a soluble protein.

Some aspects concern a nucleic acid that encodes any of the polypeptides discussed herein. The nucleic acid may be isolated and/or recombinant. It may be a nucleic acid segment that is isolated and/or recombinant. In some embodiments, the nucleic acid is DNA, while in others it is RNA. In some embodiments, the nucleic acid is a DNA segment. In some embodiments, the nucleic acid is an expression vector that is capable of expressing any of the polypeptides having an Fc binding domain with one or more substitutions that specifically binds FcγRIIb. A nucleic acid may encode one or more polypeptides herein, which, depending on the presence or absence of certain mutations, as well as how the polypeptide is produced, may or may not be glycosylated.

In some embodiments, the nucleic acid encodes a polypeptide comprising or consisting of a variant or mutant Fc domain capable of selectively binding FcγRIIb as described herein. The nucleic acid may be placed (e.g., transfected or transformed) into a host cell that can express the polypeptide, such as an aglycosylated version of the polypeptide. The host cell may be a prokaryotic cell, such as a bacterial cell. Alternatively, the host cell may be a eukaryotic cell, such as a mammalian cell. In some embodiments, a host cell contains a first expression vector, though it may comprises a second expression vector as well. Because some antibodies are made of multiple polypeptides, a host cell that contains the expression vector(s) needed to express the polypeptides may be utilized in some embodiments. For example, in some embodiments the host cell includes a second expression vector that encodes a polypeptide comprising or consisting of an immunoglobulin light chain. In some embodiments, the host cell expresses a first expression vector encoding a polypeptide comprising or consisting of an immunoglobulin heavy chain (e.g., containing a variant or mutant Fc domain that selectively binds FcγRIIb). The host cell may comprise, e.g., one or two expression vectors to allow for the expression of an antibody comprising a heavy chain and a light chain.

In some aspects, a population of host cells is provided, wherein the population contains a plurality of host cells that express polypeptides having different Fc domains. It is contemplated that the amino acid sequence of any two different Fc domains may differ in identity by less than 20%, 15%, 10%, 5%, or less.

In some aspects, provided are methods of making the polypeptides described herein (e.g., polypeptides having an aglycosylated Fc region that can selectively bind FcγRIIb) as well as methods of using these polypeptides. It is anticipated that methods described herein or known to one of ordinary skill may be to generate or use any of the polypeptides described herein.

In some embodiments, there are methods for preparing an aglycosylated polypeptide comprising: a) obtaining a host cell capable of expressing an aglycosylated polypeptide comprising an Fc domain capable of selectively binding FcγRIIb as described herein; b) incubating the host cell in culture under conditions to promote expression of the aglycosylated polypeptide; and, c) purifying expressed polypeptide from the host cell. In some embodiments, the host cell is a prokaryotic cell, such as a bacterial cell. In other embodiments the host cell is a eukaryotic cell and the polypeptide comprises a substitution mutation at position 299 (e.g., T299L) of the variant or mutant IgG Fc domain. In further embodiments, methods involve collecting the expressed variant polypeptide (e.g., from the supernatant), which may be done prior to purification.

In some embodiments, methods involve purifying the polypeptide from the supernatant. This may involve subjecting the polypeptides from the supernatant to filtration, HPLC, anion or cation exchange, high performance liquid chromatography (HPLC), affinity chromatography or a combination thereof. In some embodiments, methods involve affinity chromatography using staphylococcal Protein A, which binds the IgG Fc region. Other purification methods are well known to those of ordinary skill in the art.

In some embodiments, there is provided a pharmaceutical formulation comprising a polypeptide or nucleic acid of the present embodiments in a pharmaceutically acceptable carrier or a pharmaceutical preparation comprising an excipient.

In some embodiments, an immune response may be induced in a subject by a method comprising providing or administering (e.g., intravenously, etc.) to the subject an antibody, wherein the antibody is aglycosylated and comprises an Fc domain that selectively binds FcγRIIb, as described herein. In some aspects, the aglycosylated antibody may be capable of specifically binding human FcγRIIb. In some aspects, the aglycosylated antibody may be capable of specifically binding any of the activating FcγR polypeptides at a level that is at least 10-fold lower than glycosylated, wild-type human IgG1 antibodies. In some embodiments, the aglycosylated antibody may comprise a variant Fc domain that exhibits no specific or detectable binding an FcγRI polypeptide. In some aspects, the antibody may be an aglycosylated version of a therapeutic antibody.

In a further embodiment, cancer, infection, autoimmune or inflammatory diseases may be treated by administering a therapeutic polypeptide comprising a variant or mutant Fc domain that selectively binds FcγRIIb as described herein. It is envisioned that a polypeptide comprising a mutant or variant Fc domain as described herein may exhibit a decreased CDC compared to the CDC induced by a polypeptide comprising a wild-type human IgG Fc region. In still a further embodiment, the polypeptides according to the present invention may exhibit a reduced ADCC or ADCP as compared to wild-type human IgG antibodies.

In a further embodiment therapeutic inhibition of a protein target may be achieved by antibodies comprising variant Fc polypeptides as contemplated herein. In some embodiments involving a polypeptide comprising a variant or mutant Fc domain that can selectively bind the inhibitory FcγRIIb while exhibiting decreased binding to activating Fc, the polypeptide may exhibit a reduced CDC compared to the CDC induced by a polypeptide comprising a wild-type human IgG Fc region.

In one embodiment, a method is provided for treating a subject having a disease comprising administering to the subject an effective amount of a pharmaceutical formulation of the present embodiments. In some aspects, the tumor may be a solid tumor or a hematological tumor. In certain aspects, the subject may be a human patient. In some aspects, the pharmaceutical formulation may be administered intratumorally, intravenously, intradermally, intraarterially, intraperitoneally, intralesionally, intracranially, intraarticularly, intraprostaticaly, intrapleurally, intratracheally, intraocularly, intranasally, intravitreally, intravaginally, intrarectally, intramuscularly, subcutaneously, subconjunctival, intravesicularlly, mucosally, intrapericardially, intraumbilically, orally, by inhalation, by injection, by infusion, by continuous infusion, by localized perfusion bathing target cells directly, via a catheter, or via a lavage. In some aspects, the method may further comprise administering at least a second anticancer therapy to the subject, such as, for example, a surgical therapy, chemotherapy, radiation therapy, cryotherapy, hormone therapy, immunotherapy or cytokine therapy.

In one embodiment, a composition comprising a variant Fc domain of the present embodiments or a nucleic acid encoding a variant Fc domain of the present embodiments is provided for use in the treatment of a disease. Treating the disease may involve binding a select protein to achieve a therapeutic effect (e.g., resulting from binding of a toxin, or stimulation of a receptor with an agonistic antibody, etc.) while generating a reduced immune activation or reduced complement dependent cytotoxicity. In some aspects, the disease may be a cancer, an autoimmune disease, an inflammatory disease, or an infectious disease. In another embodiment, the use of a polypeptide according to the present embodiments or a nucleic acid encoding a polypeptide according to the present embodiments in the manufacture of a medicament for the treatment of a disease such as cancer is provided.

As used herein, "selectively binding FcγRIIb" or "selectively binds FcγRIIb" refer to a property of a polypeptide such as a Fc domain (e.g., a mutant or variant IgG Fc domain) to have the ability to bind FcγRIIb, and preferably the polypeptide or Fc domain has the ability to display increased binding of FcγRIIb as compared to a wild-type Fc domain (e.g., a wild-type Fc IgG domain). In some embodiments, a Fc domain or polypeptide that selectively binds FcγRIIb also displays either reduced binding as compared to wild-type (e.g., a wild-type IgG Fc domain) or no detectable binding of an activating Fcγ receptor. In some embodiments, a Fc domain or polypeptide that selectively binds FcγRIIb also displays either reduced binding as compared to wild-type (e.g., a wild-type IgG Fc domain) or no detectable binding of 1, 2, 3, 4, or all of FcγRI, FcγRIIa H131, FcγRIIa R131, FcγRIIIa F158, and/or FcγRIIIa V158.

As used herein, "essentially free," in terms of a specified component, is used herein to mean that none of the specified component has been purposefully formulated into a composition and/or is present only as a contaminant or in trace amounts. The total amount of the specified component resulting from any unintended contamination of a composition is therefore well below 0.05%, preferably below 0.01%. Most preferred is a composition in which no amount of the specified component can be detected with standard analytical methods.

As used herein, the term "affinity" refers to the equilibrium constant for the reversible binding of two agents and is expressed as $K_D$. Affinity of a binding domain to its target can be, for example, from about 100 nanomolar (nM) to about 0.1 nM, from about 100 nM to about 1 picomolar (pM), or from about 100 nM to about 1 femtomolar (fM); alternatively, it can be between 100 nM and 1 nM or between 0.1 nM and 10 nM. Moreover, it is contemplated that agents specifically bind when there is an affinity between the two agents that is in the affinity ranges discussed above.

As used herein the terms "encode" or "encoding," with reference to a nucleic acid, are used to make the invention readily understandable by the skilled artisan; however, these terms may be used interchangeably with "comprise" or "comprising," respectively.

As used herein in the specification, "a" or "an" may mean one or more. As used herein in the claim(s), when used in conjunction with the word "comprising," the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Throughout this application, the term "about" is used to indicate that a value includes the inherent variation of error for the device, the method being employed to determine the value, or the variation that exists among the study subjects.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 19: Alignment of wild-type human IgG1 Fc ("IgG1 Fc"; SEQ ID NO:1) and different Fc mutants, as shown. Numbering of the amino acids in the WT IgG1 Fc and mutations in the different Fc mutants are shown.

DESCRIPTION OF ILLUSTRATIVE EMBODIMENTS

Figure 1A:
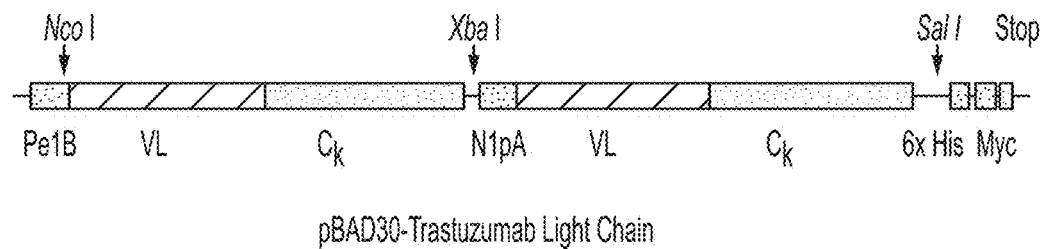
FIGS. 1A-B: Brief schematic of two plasmid system for bacterial anchored periplasmic display (APEx of Harvey et al., 2004) of Trastuzumab light chain (FIG. 1A) and Trastuzumab heavy chain (FIG. 1B).

Provided herein are methods and compositions involving polypeptides having engineered antibody Fc domains displaying improved binding to FcγRIIB. Such polypeptides may comprise an aglycosylated Fc domain that comprises one or more substitutions compared to a native Fc domain (SEQ ID NO: 1). Additionally, some Fc domains may bind selectively to FcγRIIB but not others. For example, polypeptides may comprise an aglycosylated Fc domain that selectively binds FcγRIIB, but that does not detectably bind to any FcγRs.

I. Antibody FC Domains

FcγRIIB-bound Fc domain of IgG have been shown to suppress the activation of diverse immune cells in a variety of different assays (Sidman, C. L. and Unanue, E. R. 1976; Phillips, N. E. and Parker, D. C. 1984). FcγRIIB is the only FcγR expressed by B cells, and if it is cross-linked to the B cell receptor (BCR) the threshold for B cell activation is increased and B cell differentiation and eventually antibody production are decreased. In other immune cells, including dendritic cells (DCs), macrophages, activated neutrophils, mast cells and basophils, FcγRIIB inhibits the functions mediated by activating FcγRs including phagocytosis and pro-inflammatory cytokine release. When expressed by follicular DCs (FDCs), FcγRIIB is important for trapping the antigen-containing immune complexes that are thought to be crucial for driving the germinal center response (Qin, D. et al. 2000; Barrington, R. A. 2002). The diversity of FcγRIIB expression and function underlies its importance in regulating defense against infection and in susceptibility to autoimmune disease.

Importantly binding to FcγRIIB on effector and stromal cells has been shown to be critical for the agonistic function of TNFRS therapeutic antibodies (agonistic antibodies targeting key TNF receptor (TNFR) molecules). Many TNFRS agonistic antibodies including anti-CD40 or death receptor 5 (DR5) have been shown to be of key importance for immune regulation and activation. Signaling by agonistic antibodies to targets such as CD40 has been shown to depend on ligation of the Fc domain of the antibody by FcγRIIB expressed on neighboring cells in the microenvironment (Nimmerjahn F. et al. 2005; Nicholas S. Wilson et al. 2011).

The FcγR binding sites on IgG1 have been determined by co-crystal structures of Fc fragments and the extracellular domains of FcγRs. The binding sites are generally located on the CH2 domain. The IgG1 lower hinge region (Leu234-Ser239) and Asp265-Ser267 segment in CH2 domain have a key role in the interaction with all FcγRs (Christine Gaboriaud et al., 2003 and Jenny M. Woof et al., 2004).

The CH2 domain has one N-glycosylation site at Apn297 and the N-linked glycosylation at Asn297 bridges the gap between the two CH2 domains. This bridge maintains the proper conformation of CH2 domains for binding to FcγRs. On the other hand, the removal of glycan at Asn297 drastically increases the conformation of CH2 domains such that aglycosylated Fcs bind to FcγRs with significantly reduced affinity or not at all, thus significantly diminishing ADCC, ADCP and other biological effects mediated by the Fc:FcγR interaction (M. Jack Borrok et al., 2012).

In light of the importance of FcγRIIB binding for the biological function of antibodies there have been extensive efforts on engineering IgG1 Fc domains that bind to this receptor with increased affinity and/or selectivity relative to other Fcγ receptors. These efforts have all involved the engineering of glycosylated IgG1 to bind with higher affinity to FcγRIIB since antibodies that lack the glycan at position 297 and hence they are aglycosylated do not exhibit any binding to FcγRIIB. Two IgG1 Fc variants with markedly increased binding to FcγRIIB have been reported: the so called "EF-Fc" variant developed by Xencor and the "V12-Fc" variant by Chugai (Seung Y. Chu et al. 2008; F. Mimoto et al. 2013; WO 2012115241 A1) The EF-Fc variant contains two mutations: S267E and L328F. The V12-Fc variant has five mutations: E233D, G237D, H268D, P271G, and A330R. The EF variant was reported to have 430-fold lower KD (equilibrium dissociation constant for FcγRIIB while the V-12 variant showed 64-fold greater affinity. However Fc domain was selective for FcγRIIB. Specifically the EF Fc domain showed similar affinity for FcγRI and FcγRIIA$_{H131}$ relative to authentic (wild-type) human IgG1 Fc domain and significantly enhanced affinity for FcγRIIA$_{R131}$. V12-Fc variant was reported to have similar affinity for FcγRIIA$_{R131}$ and a decreased affinity for FcγRI and FcγRIIA$_{H131}$, relative to the native IgG1 Fc domain.

In certain embodiments, there are compositions comprising a proteinaceous molecule that has been modified relative to a native or wild-type protein. In some embodiments that proteinaceous compound has been deleted of amino acid residues; in other embodiments, amino acid residues of the proteinaceous compound have been replaced; while in still further embodiments both deletions and replacements of amino acid residues in the proteinaceous compound have been made. Furthermore, a proteinaceous compound may include an amino acid molecule comprising more than one polypeptide entity. As used herein, a "proteinaceous molecule," "proteinaceous composition," "proteinaceous compound," "proteinaceous chain," or "proteinaceous material" generally refers, but is not limited to, a protein of greater than about 200 amino acids or the full-length endogenous sequence translated from a gene; a polypeptide of 100 amino acids or greater; and/or a peptide of 3 to 100 amino acids. All the "proteinaceous" terms described above may be used interchangeably herein; however, it is specifically contemplated that embodiments may be limited to a particular type of proteinaceous compound, such as a polypeptide. Furthermore, these terms may be applied to fusion proteins or protein conjugates as well. A protein may include more than one polypeptide. An IgG antibody, for example, has two heavy chain polypeptides and two light chain polypeptides, which are joined to each other through disulfide bonds.

As used herein, a protein or peptide generally refers, but is not limited to, a protein of greater than about 200 amino acids, up to a full length sequence translated from a gene; a polypeptide of greater than about 100 amino acids; and/or a peptide of from about 3 to about 100 amino acids. For convenience, the terms "protein," "polypeptide," and "peptide" are used interchangeably herein.

As used herein, an "amino acid residue" refers to any amino acid, amino acid derivative, or amino acid mimic as would be known to one of ordinary skill in the art. In certain embodiments, the residues of the proteinaceous molecule are sequential, without any non-amino acid residue interrupting the sequence of amino acid residues. In other embodiments, the sequence may comprise one or more non-amino acid moieties. In particular embodiments, the sequence of residues of the proteinaceous molecule may be interrupted by one or more non-amino acid moieties.

As used herein a "distinct Fc domain" may be defined as a domain that differs from another Fc by as little as one amino acid. Methods for making a library of distinct antibody Fc domains or nucleic acids that encode antibodies are well known in the art. For example, in some cases Fc domains may be amplified by error prone PCR. Furthermore, in certain cases a plurality of antibody Fc domains may comprise a stretch (1, 2, 3, 4, 5, 6, 7, 8, 9, 10 or more) of amino acids that have been randomized. In certain cases, specific mutations may be engineered into Fc domains. For example, in some aspects, residues that are normally glycosylated in an antibody Fc domain may be mutated. Furthermore, in certain aspects, residues that are normally glycosylated (or adjacent residues) may be used as a site for an insertion of 1, 2, 3, 4, 5, 6, 7, 8, 9, 10 or more amino acids.

A polypeptide may comprise an aglycosylated antibody Fc domain capable of binding an FcR polypeptide. In some aspects, the aglycosylated Fc domain may be further defined as having a specific affinity for an FcR polypeptide under physiological conditions. For instance an Fc domain may have an equilibrium dissociation constant between about $10^{-6}$M to about $10^{-9}$ M under physiological conditions. Furthermore in some aspects an aglycosylated Fc domain may be defined as comprising one or more amino acid substitutions or insertions relative to a wild-type sequence, such as a human wild-type sequence.

Means of preparing such a polypeptide include those discussed in PCT Publn. WO 2008/137475, which is hereby incorporated by reference. One can alternatively prepare such polypeptides directly by genetic engineering techniques such as, for example, by introducing selected amino acid substitutions or insertions into a known Fc background, wherein the insertion or substitution provides an improved FcR binding capability to aglycosylated Fc regions, as discussed above. In some embodiments, an Fc domain is engineered to bind one or more specific Fc receptors. Additionally or alternatively, an Fc domain may be engineered so that it does not specifically bind one or more specific Fc receptors.

In some embodiments, an aglycosylated Fc domain comprises a specific binding affinity for an FcR such as human FcγRIA, FcγRIIA, FcγRIIB, FcγRIIc, FcγRIIIA, FcγRIIIb, FcαRI, or for C1q. Thus, in some aspects an aglycosylated Fc domain of the invention is defined as an Fc domain with a specific affinity for FcγRIIB. The binding affinity of an antibody Fc or other binding protein can, for example, be determined by the Scatchard analysis of Munson and Pollard (1980). Alternatively, binding affinity can be determined by surface plasmon resonance or any other well known method for determining the kinetics and equilibrium constants for protein:protein interactions.

Amino acids sequences of Fc domains of the isolated IgG variants with specific affinity for FcγRIIB with changes shown relative to wild-type Fc (SEQ ID NO: 1) are as follows:

TABLE 1

Isolated IgG variants with affinity for FcγRIIB (Sequence numbering is based on Kabat and mutations are specified below)

| | |
|---|---|
| B5 | (E233Q; L234F; L235I; G237R; K322E; L351Q), |
| B7 | (E233V; L235F; G236K; F241Y; Q386R), |

TABLE 1-continued

Isolated IgG variants with affinity for FcγRIIB (Sequence numbering is based on Kabat and mutations are specified below)

| | |
|---|---|
| B13 | (V264A; L328S; P329C; A330W; I332N; E333G; I336V), |
| B15 | (M428T), |
| B19 | (L235E; G236S; P238A; S239E; K288E; K290R; K340R; Q342P; P396S), |
| B21 | (L234R; L235E; G236E; P238R; L351Q), |
| B25 | (Q311K), |
| B26 | (L234T; L235T; G236E; G237A; G238A; V263A; S375G; S408N; S440G), |
| B28 | (K290R; S375I; F423L), |
| B29 | (E233V; L234F; G236P; G237V; W81G; V348A; Q362R), |
| B33 | (S403P), |
| B34 | (E233A; G237D; T411A), |
| B36 | (V262A; L306P; K334E; E380K), |
| B39 | (K248R; L328F; Q418R), |
| B41 | (L235E; G236E; L351Q), |
| B46 | (E233K; L234H; G236V; G237T; T307A; D399G; K409R), |
| B49 | (L234H; L235P; G237V; T260A; E269G; K274E; Q295H; T299M; N389D), |
| B51 | (V263A; E269G; N297T; L328S; P329A; A330P; P331A; I332T; K360E; S383N; T394P), |
| B56 | (E233V; L234F; G236P; G237V; W313G; V348A; Q362R), |
| B57 | (E233Q; L235H; G236R; G237V; K246R; M252V; K288M; E294K; Y296H; T307A; P352L; E388G; F404L), |
| B67 | (E233D; L235P; G237E), |
| B70 | (E233A; L235Q; G236R; Q295R; L328D; P329V; A330T; I332S; K338E; H433Y; Y436C), |
| B78 | (G236C; L251P; M252K; E269D; V279M; V306I; I336V; L351Q), |
| B80 | (SEQ ID NO: 22; E233D; L235P; G237E; L351Q), |
| B81 | (F243S; H285Q; N286S; E294C; T307A; N315S; T394I; K414R), |
| B87 | (L234H; G236V; G237R; H268Q), |
| B88 | (L234H; L235N; G236M; P238M; F243S; H263Y; T307A; Q386R; L406P; H429R; Y436C), |
| B89 | (T250I; E272K; K288E; Y296C; V303I), |
| B90 | (L234G; L235C; G236Q; P238L; S239L; C311R; F404L; L406P) |
| B91 | (L314P; L328R; P329S; A330D; S337N), |
| Bn2 | (K246Q; T260A; L351Q; Q386R; P396F; V397M), |
| Bn15 | (Y296C; Q386R), |
| Bn17 | (K246Q; T260A; N315S; I336M; K340R; Q342D; A378T; Q386R), |
| Bn20 | (T260A; L351Q; Q386R; P396S; V397M), |
| Bn22 | (L351Q; Q386R; P396S; V397M), |
| Bn28 | (V264A; Y296C; N297Q; Q311K; R344Q; Q418R), |
| Bn31 | (V264A; N297Q) |

Specific point mutations listed for the mutant or variant Fc domains in Table 1 above; these mutations indicate differences between the mutant or variant Fc domain and a wild-type IgG Fc domain (SEQ ID NO:1). Some aspects of the present invention relate to an polypeptide having or a nucleic acid encoding an IgG Fc domain (such as an aglycosylated IgG Fc domain) having at least 85%, 90%, 95%, 96%, 97%, 98%, 99%, or 100%, or any range derivable therein, sequence identity to a mutant or variant Fc domain of Table 1. In some embodiments, a substitution mutation at T299 (e.g., T299L) is also included in a Fc mutant of Table 1, e.g., to allow for the production of an aglycosylated Fc domain in mammalian cells.

By "position" as used herein is meant a location in the sequence of a protein. Positions may be numbered sequentially, or according to an established format, for example the EU index for antibody numbering.

For all positions discussed in the present invention, numbering is according to the EU index. The "EU index" or "EU index as in Kabat" or "EU numbering scheme" refers to the numbering of the EU antibody (Edelman et al., 1969; Kabat et al., 1991; both incorporated herein by reference in their entirety).

In certain embodiments the size of the at least one Fc polypeptide proteinaceous molecule may comprise, but is not limited to, about or at least 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100, 110, 120, 130, 140, 150, 160, 170, 180, 190, 200, 210, 220, 230, 240, 250, 275, 300, 350, 400, 450, 500, 550, 600, 650, 700, 750, 800, 850, 900, 950, 1000 or greater amino molecule residues, and any range derivable therein. Compounds may include the above-mentioned number of contiguous amino acids from SEQ ID NO:1 (human IgG Fc polypeptide) or from a variant Fc domain as listed in Table 1 and these may be further qualified as having a percent identity or homology to SEQ ID NO: 1 (discussed herein).

A. Modified Proteins and Polypeptides

Some embodiments concern modified proteins and polypeptides, particularly a modified protein or polypeptide that exhibits at least one functional activity that is comparable to the unmodified version, yet the modified protein or polypeptide possesses an additional advantage over the unmodified version, such as suppressing B-cell activation, being easier or cheaper to produce, eliciting fewer side effects, and/or having better or longer efficacy or bioavailability. Thus, when the present application refers to the function or activity of "modified protein" or a "modified polypeptide" one of ordinary skill in the art would understand that this includes, for example, a protein or polypeptide that 1) performs at least one of the same activities or has at least one of the same specificities as the unmodified protein or polypeptide, but that may have a different level of another activity or specificity; and 2) possesses an additional advantage over the unmodified protein or polypeptide. Determination of activity may be achieved using assays familiar to those of skill in the art, particularly with respect to the protein's activity, and may include for comparison purposes, for example, the use of native and/or recombinant versions of either the modified or unmodified protein or polypeptide. It is specifically contemplated that embodiments concerning a "modified protein" may be implemented with respect to a "modified polypeptide," and vice versa. In addition to the modified proteins and polypeptides discussed herein, embodiments may involve domains, polypeptides, and proteins described in PCT Publn. WO 2008/137475, which is hereby specifically incorporated by reference.

Modified proteins may possess deletions and/or substitutions of amino acids; thus, a protein with a deletion, a protein with a substitution, and a protein with a deletion and a substitution are modified proteins. In some embodiments these modified proteins may further include insertions or added amino acids, such as with fusion proteins or proteins with linkers, for example. This may include the insertion of a targeting peptide or polypeptide or simply a single residue. Terminal additions, called fusion proteins, are discussed below.

A "modified deleted protein" lacks one or more residues of the native protein, but possesses the specificity and/or activity of the native protein. A "modified deleted protein" may also have reduced immunogenicity or antigenicity. An example of a modified deleted protein is one that has an amino acid residue deleted from at least one antigenic region (i.e., a region of the protein determined to be antigenic in a particular organism, such as the type of organism that may be administered the modified protein).

Substitutional or replacement variants typically contain the exchange of one amino acid for another at one or more sites within the protein and may be designed to modulate one or more properties of the polypeptide, particularly its effector functions and/or bioavailability. Substitutions may or may not be conservative, that is, one amino acid is replaced with one of similar shape and charge. Conservative substitutions are well known in the art and include, for example, the changes of: alanine to serine; arginine to lysine; asparagine to glutamine or histidine; aspartate to glutamate; cysteine to serine; glutamine to asparagine; glutamate to aspartate; glycine to proline; histidine to asparagine or glutamine; isoleucine to leucine or valine; leucine to valine or isoleucine; lysine to arginine; methionine to leucine or isoleucine; phenylalanine to tyrosine, leucine, or methionine; serine to threonine; threonine to serine; tryptophan to tyrosine; tyrosine to tryptophan or phenylalanine; and valine to isoleucine or leucine.

The term "biologically functional equivalent" is well understood in the art and is further defined in detail herein. Accordingly, sequences that have between about 70% and about 80%, or between about 81% and about 90%, or even between about 91% and about 99% of amino acids that are identical or functionally equivalent to the amino acids of a native polypeptide are included, provided the biological activity of the protein is maintained. A modified protein may be biologically functionally equivalent to its native counterpart.

It also will be understood that amino acid and nucleic acid sequences may include additional residues, such as additional N- or C-terminal amino acids or 5' or 3' sequences, and yet still be essentially as set forth in one of the sequences disclosed herein, so long as the sequence meets the criteria set forth above, including the maintenance of biological protein activity where protein expression is concerned. The addition of terminal sequences particularly applies to nucleic acid sequences that may, for example, include various non-coding sequences flanking either of the 5' or 3' portions of the coding region or may include various internal sequences, i.e., introns, which are known to occur within genes.

The following is a discussion based upon changing of the amino acids of a protein to create an equivalent, or even an improved, second-generation molecule. For example, certain amino acids may be substituted for other amino acids in a protein structure with or without appreciable loss of interactive binding capacity with structures such as, for example, binding sites to substrate molecules. Since it is the interactive capacity and nature of a protein that defines that protein's biological functional activity, certain amino acid substitutions can be made in a protein sequence, and in its underlying DNA coding sequence, and nevertheless produce a protein with like properties. It is thus contemplated that various changes may be made in the DNA sequences of genes without appreciable loss of their biological utility or activity, as discussed below. A proteinaceous molecule has "homology" or is considered "homologous" to a second proteinaceous molecule if one of the following "homology criteria" is met: 1) at least 30% of the proteinaceous molecule has sequence identity at the same positions with the second proteinaceous molecule; 2) there is some sequence identity at the same positions with the second proteinaceous molecule and at the nonidentical residues, at least 30% of them are conservative differences, as described herein, with respect to the second proteinaceous molecule; or 3) at least 30% of the proteinaceous molecule has sequence identity with the second proteinaceous molecule, but with possible gaps of nonidentical residues between identical residues. As used herein, the term "homologous" may equally apply to a region of a proteinaceous molecule, instead of the entire molecule. If the term "homology" or "homologous" is qualified by a number, for example, "50% homology" or "50% homologous," then the homology criteria, with respect to 1), 2), and 3), is adjusted from "at least 30%" to "at least 50%." Thus it is contemplated that there may homology or sequence identity of at least 30%, 35%, 40%, 45%, 50%, 55%, 60%, 65%, 70%, 75%, 80%, 85%, 90%, 95%, or more between two proteinaceous molecules or portions of proteinaceous molecules.

Alternatively, a modified polypeptide may be characterized as having a certain percentage of identity to an unmodified polypeptide or to any polypeptide sequence disclosed herein, including a mutant of variant Fc domain listed in Table 1. The percentage identity may be at most or at least 50%, 55%, 60%, 65%, 70%, 75%, 80%, 85%, 90%, 95%, 96%, 97%, 98%, 99% or 100% (or any range derivable therein) between two proteinaceous molecules or portions of proteinaceous molecules. It is contemplated that percentage of identity discussed above may relate to a particular region of a polypeptide compared to an unmodified region of a polypeptide. For instance, a polypeptide may contain a modified or mutant Fc domain that can be characterized based on the identity of the amino acid sequence of the modified or mutant Fc domain to an unmodified or mutant Fc domain from the same species. A modified or mutant human Fc domain characterized, for example, as having 90% identity to an unmodified Fc domain means that 90% of the amino acids in that domain are identical to the amino acids in the unmodified human Fc domain (SEQ ID NO: 1).

In making such changes, the hydropathic index of amino acids may be considered. The importance of the hydropathic amino acid index in conferring interactive biologic function on a protein is generally understood in the art (Kyte and Doolittle, 1982). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

It also is understood in the art that the substitution of like amino acids can be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with a biological property of the protein. As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). It is understood that an amino acid can be substituted for another having a similar hydrophilicity value and still produce a biologically equivalent and immunologically equivalent protein. In such changes, the substitution of amino acids whose hydrophilicity values are within ±2 is preferred, those that are within ±1 are particularly preferred, and those within ±0.5 are even more particularly preferred.

As outlined above, amino acid substitutions generally are based on the relative similarity of the amino acid side-chain substituents, for example, their hydrophobicity, hydrophilicity, charge, size, and the like. Exemplary substitutions that take into consideration the various foregoing characteristics are well known to those of skill in the art and include: arginine and lysine; glutamate and aspartate; serine and threonine; glutamine and asparagine; and valine, leucine, and isoleucine.

B. Modified Antibodies and Proteinaceous Compounds with Heterologous Regions Once an Fc domain has been isolated, it may be desired to link the molecule to at least one agent to form a conjugate to enhance the utility of that molecule. For example, in order to increase the efficacy of Fc domains or antibody molecules as diagnostic or therapeutic agents, it is conventional to link or covalently bind or complex at least one desired molecule or moiety. Such a molecule or moiety may be, but is not limited to, at least one effector or reporter molecule. Effecter molecules comprise molecules having a desired activity, e.g., cytotoxic activity. Non-limiting examples of effector molecules that have been attached to antibodies include toxins, anti-tumor agents, therapeutic enzymes, radio-labeled nucleotides, antiviral agents, chelating agents, cytokines, growth factors, and oligo- or poly-nucleotides. By contrast, a reporter molecule is defined as any moiety that may be detected using an assay. Non-limiting examples of reporter molecules that have been conjugated to antibodies include enzymes, radiolabels, haptens, fluorescent labels, phosphorescent molecules, chemiluminescent molecules, chromophores, luminescent molecules, photoaffinity molecules, colored particles, or ligands, such as biotin. Another such example is the formation of a conjugate comprising an antibody linked to a cytotoxic or anti-cellular agent, and may be termed "immunotoxins." Techniques for labeling such a molecule are known to those of skill in the art and have been described herein above.

Labeled proteins, such as Fc domains that have been prepared in accordance with the invention may also then be employed, for example, in immunodetection methods for binding, purifying, removing, quantifying, and/or otherwise generally detecting biological components, such as protein (s), polypeptide(s), or peptide(s). Some immunodetection methods include enzyme linked immunosorbent assay (ELISA), radioimmunoassay (RIA), immunoradiometric assay, fluoroimmunoassay, chemiluminescent assay, bioluminescent assay, and Western blot to mention a few. The steps of various useful immunodetection methods have been described in the scientific literature, such as, e.g., Doolittle and Ben-Zeev, 1999; Gulbis and Galand, 1993; and De Jager et al., 1993, each incorporated herein by reference.

The Fc domain molecules, including antibodies, may be used, for example, in conjunction with both fresh-frozen and/or formalin-fixed, paraffin-embedded tissue blocks prepared for study by immunohistochemistry (IHC). The method of preparing tissue blocks from these particulate specimens has been successfully used in previous IHC studies of various prognostic factors, and/or is well known to those of skill in the art (Abbondanzo et al., 1990).

Some embodiments concern an Fc polypeptide proteinaceous compound that may include amino acid sequences from more than one naturally occurring or native polypeptides or proteins. Embodiments discussed above are contemplated to apply to this section, and vice versa. For instance, a modified antibody is one that contains a modified Fc domain with an antigen binding domain. Moreover, the antibody may have two different antigen binding regions, such as a different region on each of the two heavy chains. Alternatively or additionally, in some embodiments, there are polypeptides comprising multiple heterologous peptides and/or polypeptides ("heterologous" meaning they are not derived from the same polypeptide). A proteinaceous compound or molecule, for example, could include a modified Fc domain with a protein binding region that is not from an antibody. In some embodiments, there are polypeptides comprising a modified Fc domain with a protein binding region that binds a cell-surface receptor. These proteinaceous molecules comprising multiple functional domains may be two or more domains chemically conjugated to one another or it may be a fusion protein of two or more polypeptides encoded by the same nucleic acid molecule. It is contemplated that proteins or polypeptides may include all or part of two or more heterologous polypeptides.

Thus, a multipolypeptide proteinaceous compound may be comprised of all or part of a first polypeptide and all or part of a second polypeptide, a third polypeptide, a fourth polypeptide, a fifth polypeptide, a sixth polypeptide, a seventh polypeptide, an eight polypeptide, a ninth polypeptide, a tenth polypeptide, or more polypeptides.

Amino acids, such as selectively-cleavable linkers, synthetic linkers, or other amino acid sequences, may be used to separate proteinaceous moieties.

Polypeptides or proteins (including antibodies) having an antigen binding domain or region of an antibody and an aglycosylated Fc domain can be used against any antigen or epitope, including but not limited to proteins, subunits, domains, motifs, and/or epitopes belonging to the following list of targets: 17-IA, 4-1BB, 4Dc, 6-keto-PGF1a, 8-iso-PGF2a, 8-oxo-dG, A1 Adenosine Receptor, A33, ACE, ACE-2, Activin, Activin A, Activin AB, Activin B, Activin C, Activin RIA, Activin RIA ALK-2, Activin RIB ALK-4, Activin RIIA, Activin RIIB, ADAM, ADAM10, ADAM12, ADAM15, ADAM17/TACE, ADAM8, ADAM9, ADAMTS, ADAMTS4, ADAMTS5, Addressins, aFGF, ALCAM, ALK, ALK-1, ALK-7, alpha-1-antitrypsin, alpha-V/beta-1 antagonist, ANG, Ang, APAF-1, APE, APJ, APP, APRIL, AR, ARC, ART, Artemin, anti-Id, ASPARTIC, Atrial natriuretic factor, av/b3 integrin, Ax1, b2M, B7-1, B7-2, B7-H, B-lymphocyte Stimulator (BlyS), BACE, BACE-1, Bad, BAFF, BAFF-R, Bag-1, BAK, Bax, BCA-1, BCAM, Bcl, BCMA, BDNF, b-ECGF, bFGF, BID, Bik, BIM, BLC, BL-CAM, BLK, BMP, BMP-2 BMP-2a, BMP-3 Osteogenin, BMP-4 BMP-2b, BMP-5, BMP-6 Vgr-1, BMP-7 (OP-1), BMP-8 (BMP-8a, OP-2), BMPR, BMPR-IA (ALK-3), BMPR-IB (ALK-6), BRK-2, RPK-1, BMPR-II (BRK-3), BMPs, b-NGF, BOK, Bombesin, Bone-derived neurotrophic factor, BPDE, BPDE-DNA, BTC, complement factor 3 (C3), C3a, C4, C5, C5a, C10, CA125, CAD-8, Calcitonin, cAMP, carcinoembryonic antigen (CEA), carcinoma-associated antigen, Cathepsin A, Cathepsin B, Cathepsin C/DPPI, Cathepsin D, Cathepsin E, Cathepsin H, Cathepsin L, Cathepsin O, Cathepsin S, Cathepsin V, Cathepsin X/ZIP, CBL, CCI, CCK2, CCL, CCL1, CCL11, CCL12, CCL13, CCL14, CCL15, CCL16, CCL17, CCL18, CCL19, CCL2, CCL20, CCL21, CCL22, CCL23, CCL24, CCL25, CCL26, CCL27, CCL28, CCL3, CCL4, CCL5, CCL6, CCL7, CCL8, CCL9/10, CCR, CCR1, CCR10, CCR10, CCR2, CCR3, CCR4, CCR5, CCR6, CCR7, CCR8, CCR9, CD1, CD2, CD3, CD3E, CD4, CD5, CD6, CD7, CD8, CD10, CD11a, CD11b, CD11c, CD13, CD14, CD15, CD16, CD18, CD19, CD20, CD21, CD22, CD23, CD25, CD27L, CD28, CD29, CD30, CD30L, CD32, CD33 (p67 proteins), CD34, CD38, CD40, CD40L, CD44, CD45, CD46, CD49a, CD52, CD54, CD55, CD56, CD61, CD64, CD66e, CD74, CD80 (B7-1), CD89, CD95, CD123, CD137, CD138, CD140a, CD146, CD147, CD148, CD152, CD164, CEACAM5, CFTR, cGMP, CINC, *Clostridium botulinum* toxin, *Clostridium perfringens* toxin, CKb8-1, CLC, CMV, CMV UL, CNTF, CNTN-1, COX, C-Ret, CRG-2, CT-1, CTACK, CTGF, CTLA-4, CX3CL1, CX3CR1, CXCL, CXCL1, CXCL2, CXCL3, CXCL4, CXCL5, CXCL6, CXCL7, CXCL8, CXCL9, CXCL10, CXCL11, CXCL12, CXCL13, CXCL14, CXCL15, CXCL16, CXCR, CXCR1, CXCR2, CXCR3, CXCR4, CXCR5, CXCR6, cytokeratin tumor-associated antigen, DAN, DCC, DcR3, DC-SIGN, Decay accelerating factor, des(1-3)-IGF-I (brain IGF-1), Dhh, digoxin, DNAM-1, Dnase, Dpp, DPPIV/CD26, Dtk, ECAD, EDA, EDA-A1, EDA-A2, EDAR, EGF, EGFR (ErbB-1), EMA, EMMPRIN, ENA, endothelin receptor, Enkephalinase, eNOS, Eot, eotaxin1, EpCAM, Ephrin B2/EphB4, EPO, ERCC, E-selectin, ET-1, Factor IIa, Factor VII, Factor VIIIc, Factor IX, fibroblast activation protein (FAP), Fas, FcR1, FEN-1, Ferritin, FGF, FGF-19, FGF-2, FGF3, FGF-8, FGFR, FGFR-3, Fibrin, FL, FLIP, Flt-3, Flt-4, Follicle stimulating hormone, Fractalkine, FZD1, FZD2, FZD3, FZD4, FZD5, FZD6, FZD7, FZD8, FZD9, FZD10, G250, Gas 6, GCP-2, GCSF, GD2, GD3, GDF, GDF-1, GDF-3 (Vgr-2), GDF-5 (BMP-14, CDMP-1), GDF-6 (BMP-13, CDMP-2), GDF-7 (BMP-12, CDMP-3), GDF-8 (Myostatin), GDF-9, GDF-15 (MIC-1), GDNF, GDNF, GFAP, GFRa-1, GFR-alpha1, GFR-alpha2, GFR-alpha3, GITR, Glucagon, Glut 4, glycoprotein IIb/IIIa (GP IIb/IIIa), GM-CSF, gp130, gp72, GRO, Growth hormone releasing factor, Hapten (NP-cap or NIP-cap), HB-EGF, HCC, HCMV gB envelope glycoprotein, HCMV) gH envelope glycoprotein, HCMV UL, Hemopoietic growth factor (HGF), Hep B gp120, heparanase, Her2, Her2/neu (ErbB-2), Her3 (ErbB-3), Her4 (ErbB-4), herpes simplex virus (HSV) gB glycoprotein, HSV gD glycoprotein, HGFA, High molecular weight melanoma-associated antigen (HMW-MM), HIV gp120, HIV IIIB gp120 V3 loop, HLA, HLA-DR, HM1.24, HMFG PEM, HRG, Hrk, human cardiac myosin, human cytomegalovirus (HCMV), human growth hormone (HGH), HVEM, 1-309, IAP, ICAM, ICAM-1, ICAM-3, ICE, ICOS, IFNg, Ig, IgA receptor, IgE, IGF, IGF binding proteins, IGF-1R, IGFBP, IGF-I, IGF-II, IL, IL-1, IL-1R, IL-2, IL-2R, IL-4, IL-4R, IL-5, IL-5R, IL-6, IL-6R, IL-8, IL-9, IL-10, IL-12, IL-13, IL-15, IL-18, IL-18R, IL-23, interferon (INF)-alpha, INF-beta, INF-gamma, Inhibin, iNOS, Insulin A-chain, Insulin B-chain, Insulin-like growth factor 1, integrin alpha2, integrin alpha3, integrin alpha4, integrin alpha4/beta1, integrin alpha4/beta7, integrin alpha5 (alphaV), integrin alpha5/beta1, integrin alpha5/beta3, integrin alpha6, integrin beta1, integrin beta2, interferon gamma, IP-10, I-TAC, JE, Kallikrein 2, Kallikrein 5, Kallikrein 6, Kallikrein 11, Kallikrein 12, Kallikrein 14, Kallikrein 15, Kallikrein L1, Kallikrein L2, Kallikrein L3, Kallikrein L4, KC, KDR, Keratinocyte Growth Factor (KGF), laminin 5, LAMP, LAP, LAP (TGF-1), Latent TGF-1, Latent TGF-1 bp1, LBP, LDGF, LECT2, Lefty, Lewis-Y antigen, Lewis-Y related antigen, LFA-1, LFA-3, Lfo, LIF, LIGHT, lipoproteins, LIX, LKN, Lptn, L-Selectin, LT-a, LT-b, LTB4, LTBP-1, Lung surfactant, Luteinizing hormone, Lymphotoxin Beta Receptor, Mac-1, MAdCAM, MAG, MAP2, MARC, MCAM, MCAM, MCK-2, MCP, M-CSF, MDC, Mer, METALLOPROTEASES, MGDF receptor, MGMT, MHC (HLA-DR), MIF, MIG, MIP, MIP-1-alpha, MK, MMAC1, MMP, MMP-1, MMP-10, MMP-11, MMP-12, MMP-13, MMP-14, MMP-15, MMP-2, MMP-24, MMP-3, MMP-7, MMP-8, MMP-9, MPIF, Mpo, MSK, MSP, mucin (Muc1), MUC18, Muellerian-inhibitin substance, Mug, MuSK, NAIP, NAP, NCAD, N-Cadherin, NCA 90, NCAM, NCAM, Neprilysin, Neurotrophin-3, -4, or -6, Neurturin, Neuronal growth factor (NGF), NGFR, NGF-beta, nNOS, NO, NOS, Npn, NRG-3, NT, NTN, OB, OGG1, OPG, OPN, OSM, OX40L, OX40R, p150, p95, PADPr, Parathyroid hormone, PARC, PARP, PBR, PBSF, PCAD, P-Cadherin, PCNA, PDGF, PDGF, PDK-1, PECAM, PEM, PF4, PGE, PGF, PGI2, PGJ2, PIN, PLA2, placental alkaline phosphatase (PLAP), PIGF, PLP, PP14, Proinsulin, Prore-laxin, Protein C, PS, PSA, PSCA, prostate specific membrane antigen (PSMA), PTEN, PTHrp, Ptk, PTN, R51, RANK, RANKL, RANTES, RANTES, Relaxin A-chain, Relaxin B-chain, renin, respiratory syncytial virus (RSV) F, RSV Fgp, Ret, Rheumatoid factors, RLIP76, RPA2, RSK, S100, SCF/KL, SDF-1, SERINE, Serum albumin, sFRP-3, Shh, SIGIRR, SK-1, SLAM, SLPI, SMAC, SMDF, SMOH, SOD, SPARC, Stat, STEAP, STEAP-II, TACE, TACI, TAG-72 (tumor-associated glycoprotein-72), TARC, TCA-3, T-cell receptors (e.g., T-cell receptor alpha/beta), TdT, TECK, TEM1, TEM5, TEM7, TEM8, TERT, testicular PLAP-like alkaline phosphatase, TfR, TGF, TGF-alpha, TGF-beta, TGF-beta Pan Specific, TGF-beta RI (ALK-5), TGF-beta RII, TGF-beta RIIb, TGF-beta RIII, TGF-beta1, TGF-beta2, TGF-beta3, TGF-beta4, TGF-beta5, Thrombin, Thymus Ck-1, Thyroid stimulating hormone, Tie, TIMP, TIQ, Tissue Factor, TMEFF2, Tmpo, TMPRSS2, TNF, TNF-alpha, TNF-alpha beta, TNF-beta2, TNFc, TNF-RI, TNF-RII, TNFRSF10A (TRAIL R1 Apo-2, DR4), TNFRSF10B (TRAIL R2 DR5, KILLER, TRICK-2A, TRICK-B), TNFRSF10C (TRAIL R3 DcR1, LIT, TRID), TNFRSF10D (TRAIL R4 DcR2, TRUNDD), TNFRSF11A (RANK ODF R, TRANCE R), TNFRSF11B (OPG OCIF, TR1), TNFRSF12 (TWEAK R FN14), TNFRSF13B (TACI), TNFRSF13C (BAFF R), TNFRSF14 (HVEM ATAR, HveA, LIGHT R, TR2), TNFRSF16 (NGFR p75NTR), TNFRSF17 (BCMA), TNFRSF18 (GITR AITR), TNFRSF19 (TROY TAJ, TRADE), TNFRSF19L (RELT), TNFRSF1A (TNF RI CD120a, p55-60), TNFRSF1B (TNF RII CD120b, p75-80), TNFRSF26 (TNFRH3), TNFRSF3 (LTbR TNF RIII, TNFCR), TNFRSF4 (OX40 ACT35, TXGP1R), TNFRSF5 (CD40p50), TNFRSF6 (Fas Apo-1, APT1, CD95), TNFRSF6B (DcR3 M68, TR6), TNFRSF7 (CD27), TNFRSF8 (CD30), TNFRSF9 (4-1BB CD137, ILA), TNFRSF21 (DR6), TNFRSF22 (DcTRAIL R2 TNFRH2), TNFRST23 (DcTRAIL R1 TNFRH1), TNFRSF25 (DR3 Apo-3, LARD, TR-3, TRAMP, WSL-1), TNFSF10 (TRAIL Apo-2 Ligand, TL2), TNFSF11 (TRANCE/RANK Ligand ODF, OPG Ligand), TNFSF12 (TWEAK Apo-3 Ligand, DR3 Ligand), TNFSF13 (APRIL TALL2), TNFSF13B (BAFF BLYS, TALL1, THANK, TNFSF20), TNFSF14 (LIGHT HVEM Ligand, LTg), TNFSF15 (TL1A/VEGI), TNF SF 18 (GITR Ligand AITR Ligand, TL6), TNF SF 1A (TNF-a Conectin, DIF, TNFSF2), TNFSF1B (TNF-b LTa, TNFSF1), TNFSF3 (LTb TNFC, p33), TNFSF4 (OX40 Ligand gp34, TXGP1), TNFSF5 (CD40 Ligand CD154, gp39, HIGM1, IMD3, TRAP), TNFSF6 (Fas Ligand Apo-1 Ligand, APT1 Ligand), TNFSF7 (CD27 Ligand CD70), TNFSF8 (CD30 Ligand CD153), TNFSF9 (4-1BB Ligand CD137 Ligand), TP-1, t-PA, Tpo, TRAIL, TRAIL R, TRAIL-R1, TRAIL-R2, TRANCE, transferring receptor, TRF, Trk, TROP-2, TSG, TSLP, tumor-associated antigen CA 125, tumor-associated antigen expressing Lewis Y related carbohydrate, TWEAK, TXB2, Ung, uPAR, uPAR-1, Urokinase, VCAM, VCAM-1, VECAD, VE-Cadherin, VE-cadherin-2, VEFGR-1 (flt-1), VEGF, VEGFR, VEGFR-3 (flt-4), VEGI, VIM, Viral antigens, VLA, VLA-1, VLA-4, VNR integrin, von Willebrands factor, WIF-1, WNT1, WNT2, WNT2B/13, WNT3, WNT3A, WNT4, WNT5A, WNT5B, WNT6, WNT7A, WNT7B, WNT8A, WNT8B, WNT9A, WNT9B, WNT10A, WNT10B, WNT11, WNT16, XCL1, XCL2, XCR1, XCR1, XEDAR, XIAP, XPD, and receptors for hormones and growth factors. In some embodiments, a polypeptide or protein has an antigen binding domain specific for one or more cell surface tumor antigens or B-cell antigen. Methods and compositions may be employed to target a tumor cell or B-cell.

Any antibody of sufficient selectivity, specificity, or affinity may be employed as the basis for an antibody conjugate. Such properties may be evaluated using conventional immunological screening methodology known to those of skill in the art. Sites for binding to biological active molecules in the antibody molecule, in addition to the canonical antigen binding sites, include sites that reside in the variable domain that can bind pathogens, B-cell superantigens, the T cell co-receptor CD4, and the HIV-1 envelope (Sasso et al., 1989; Shorki et al., 1991; Silvermann et al., 1995; Cleary et al., 1994; Lenert et al., 1990; Berberian et al., 1993; Kreier et al., 1991). In addition, the variable domain is involved in antibody self-binding (Kang et al., 1988), and contains epitopes (idiotopes) recognized by anti-antibodies (Kohler et al., 1989).

Fc domains can bind to an FcR, however, it is contemplated that the regulation of immune response can be directed not only through an antigen binding domain on the polypeptide containing the Fc domain, but through some other protein binding domain. Consequently, some embodiments may concern an Fc domain and a heterologous non-antigen binding domain. In certain embodiments, the non-antigen binding domain binds to the cell surface. Therefore, these agents require either chemical conjugation to, or fusion with, agents/proteins that are capable of binding to specific target cells. Embodiments may further include adjoining all or part of an aglycosylated Fc domain to all or part of any of the proteins listed in Table 2. It is contemplated that embodiments include, but are not limited to, the examples provided in Table 2 and the description herein.

A ligand for a receptor may be employed to target a cell expressing on its surface the receptor for the ligand. Ligands also include, for instance, CD95 ligand, TRAIL, TNF (such as TNF-α or TNF-β), growth factors, including those discussed above, such as VEGF, and cytokines, such as interferons or interleukins, and variants thereof. Embodiments with multiple domains are also contemplated, such as a VEGF Trap fusion protein that includes the second extracellular domain of the VEGF receptor 1 (Flt-1) with the third domain of the VEGF receptor 2 (KDR/Flk-1) and an IgG Fc region.

TABLE 2

Agents/proteins capable of binding specific target cells

| Protein Genus | Subgenus | Species | Subspecies |
|---|---|---|---|
| Antibodies | Polyclonal | | |
| | Monoclonal | Non-recombinant | |
| | | Recombinant | |
| | | | Chimeric |
| | | | Single chain |
| | | | Diabody |
| | | | Multimeric |
| Ligands for cell-surface receptors | | | IL-1, IL-2, IL-3, IL-4, IL-5, IL-6, IL-7, IL-8, IL-9, IL-10, IL-11, IL-12, IL-13, IL-14, IL-15, IL-16, IL-17, IL-18, IL-19 |
| | Cytokines/ growth factors | | |
| | | Cytokines/ growth factors for receptor | |

TABLE 2-continued

Agents/proteins capable of binding specific target cells

| Protein Genus | Subgenus | Species | Subspecies |
|---|---|---|---|
| | | tyrosine kinases | |
| | | | GM-CSF, G-CSF, M-CSF, EGF, VEGF, FGF, PDGF, HGF, GDNF, Trk, AXL, LTK, TIE, ROR, DDR, KLG, RYK, MuSK ligands |
| Non-Ab binding protein for cell-surface molecule | | | |
| | Binders of cell surface proteins | | |
| | | Cluster of differentiation (CD) molecules | |

C. Antibody Fc Libraries

Examples of techniques that could be employed in conjunction with embodiments for creation of diverse antibody Fc domains and/or antibodies comprising such domains may employ techniques similar to those for expression of immunoglobulin heavy chain libraries described in U.S. Pat. No. 5,824,520. Previously employed Fc libraries are discussed in PCT Publn. WO 2008/137475, which is specifically incorporated herein by reference.

II. Antibody-Binding Polypeptides

A variety of antibody-binding domains (e.g., FcR polypeptides) are known in the art and may be used in the methods and compositions of the invention. For example, in some aspects, an FcR may have specificity for a particular type or subtype of Ig, such as IgA, IgM, IgE, or IgG (e.g., IgG1, IgG2a, IgG2b, IgG3, or IgG4). Thus, in some embodiments the antibody-binding domain may be defined as an IgG binding domain. The FcR polypeptide may comprise a eukaryotic, prokaryotic, or synthetic FcR domain. For instance, an antibody Fc-binding domain may be defined as a mammalian, bacterial, or synthetic binding domain. Some Fc-binding domains for use in the invention include but are not limited to a binding domain from one of the polypeptides of Table 3. For example, an Fc-binding polypeptide may be encoded by an FCGR2A, FCGR2B, FCGR2C, FCGR3A, FCGR3B, FCGR1A, Fcgr1, FCGR2, FCGR2, Fcgr2, Fcgr2, FCGR3, FCGR3, Fcgr3, FCGR3, Fcgr3, FCGRT, mrp4, spa, or spg gene. Preferably, an FcR polypeptide for use according to the invention may be an Fc binding region from human FcγRIA, FcγRIIA, FcγRIIB, FcγRIIc, FcγRIIIA, FcγRIIIb, FcαRI, or C1q. A variety of Fc receptors to which Fc domains bind are well known in the art and some examples of receptors are listed below in Table 3.

TABLE 3

Selected FcR Polypeptides

| Protein name | Gene name | Description | Organisms | Length (aa) | Reference |
|---|---|---|---|---|---|
| Fc-gamma RII-a (CD32) | FCGR2A | Low affinity immunoglobulin gamma Fc region receptor II-a precursor | *Homo sapiens* (Human) | 317 | (Stuart et al., 1987) |
| Fc-gamma RII-a | FCGR2A | Low affinity immunoglobulin gamma Fc region receptor II-a precursor | *Pan troglodytes* (Chimpanzee) | 316 | |
| Fc-gamma RII-b | FCGR2B | Low affinity immunoglobulin gamma Fc region receptor II-b precursor | *Homo sapiens* (Human) | 310 | (Stuart et al., 1989) |
| Fc-gamma RII-c | FCGR2C | Low affinity immunoglobulin gamma Fc region receptor II-c precursor | *Homo sapiens* (Human) | 323 | (Stuart et al., 1989) |
| Fc-gamma RIIIa | FCGR3A | Low affinity immunoglobulin gamma Fc region receptor III-A precursor | *Homo sapiens* (Human) | 254 | (Ravetch and Perussia, 1989) |
| Fc-gamma RIIIb | FCGR3B | Low affinity immunoglobulin gamma Fc region receptor III-B precursor | *Homo sapiens* (Human) | 233 | (Ravetch and Perussia, 1989) |
| Fc-gamma RI (CD64) | FCGR1A | High affinity immunoglobulin gamma Fc receptor I precursor | *Homo sapiens* (Human) | 374 | (Allen and Seed, 1988) |
| Fc-gamma RI | Fcgr1 | High affinity immunoglobulin gamma Fc receptor I precursor | *Mus musculus* (Mouse) | 404 | (Sears et al., 1990) |
| Fc-gamma RII | FCGR2 | Low affinity immunoglobulin gamma Fc region receptor II precursor | *Bos taurus* (Bovine) | 296 | (Zhang et al., 1994) |
| Fc-gamma RII | FCGR2 | Low affinity immunoglobulin gamma Fc region receptor II precursor | *Cavia porcellus* (Guinea pig) | 341 | (Tominaga et al., 1990) |
| Fc-gamma RII | Fcgr2 | Low affinity immunoglobulin gamma Fc region receptor II precursor | *Mus musculus* (Mouse) | 330 | (Ravetch et al., 1986) |
| Fc-gamma RII | Fcgr2 | Low affinity immunoglobulin gamma Fc region receptor II precursor | *Rattus norvegicus* (Rat) | 285 | (Bocek and Pecht, 1993) |
| Fc-gamma RIII | FCGR3 | Low affinity immunoglobulin gamma Fc region receptor III precursor | *Bos taurus* (Bovine) | 250 | (Collins et al., 1997) |
| Fc-gamma RIII | FCGR3 | Low affinity immunoglobulin gamma Fc region receptor III precursor | *Macaca fascicularis* (Crab eating macaque) (Cynomolgus monkey) | 254 | |
| Fc-gamma RIII | Fcgr3 | Low affinity immunoglobulin gamma Fc region receptor III precursor | *Mus musculus* (Mouse) | 261 | (Ravetch et al., 1986) |
| Fc-gamma RIII | FCGR3 | Low affinity immunoglobulin gamma Fc region receptor III precursor | *Sus scrofa* (Pig) | 257 | (Halloran et al., 1994) |
| Fc-gamma RIII | Fcgr3 | Low affinity immunoglobulin gamma Fc region receptor III precursor | *Rattus norvegicus* (Rat) | 267 | (Zeger et al., 1990) |
| FcRn | FCGRT | IgG receptor transporter FcRn large subunit p51 precursor | *Homo sapiens* (Human) | 365 | |
| FcRn | FCGRT | IgG receptor transporter FcRn large subunit p51 precursor | *Macaca fascicularis* (Crab eating macaque) (Cynomolgus monkey) | 365 | |
| FcRn | Fcgrt | IgG receptor transporter FcRn large subunit p51 precursor | *Mus musculus* (Mouse) | 365 | (Ahouse et al., 1993) |
| FcRn | Fcgrt | IgG receptor transporter FcRn large subunit p51 precursor | *Rattus norvegicus* (Rat) | 366 | (Simister and Mostov, 1989) |
| MRP protein | mrp4 | Fibrinogen- and Ig-binding protein precursor | *Streptococcus pyogenes* | 388 | (Stenberg et al., 1992) |
| Protein B | | cAMP factor | *Streptococcus agalactiae* | 226 | (Ruhlmann et al., 1988) |
| protein A | spa | Immunoglobulin G-binding protein A precursor | *Staphylococcus aureus* (strain NCTC 8325) | 516 | (Uhlen et al., 1984) |
| protein A | spa | Immunoglobulin G-binding protein A precursor | *Staphylococcus aureus* | 508 | (Shuttleworth et al., 1987) |

TABLE 3-continued

Selected FcR Polypeptides

| Protein name | Gene name | Description | Organisms | Length (aa) | Reference |
|---|---|---|---|---|---|
| protein A | spa | Immunoglobulin G-binding protein A precursor | *Staphylococcus aureus* (strain Mu50/ATCC 700699) | 450 | (Kuroda et al., 2001) |
| protein A | spa | Immunoglobulin G-binding protein A precursor | *Staphylococcus aureus* (strain N315) | 450 | (Kuroda et al., 2001) |
| protein G | spg | Immunoglobulin G-binding protein G precursor | *Streptococcus* sp. group G | 448 | (Fahnestock et al., 1986) |
| protein G | spg | Immunoglobulin G-binding protein G precursor | *Streptococcus* sp. group G | 593 | (Olsson et al., 1987) |
| protein H | | Immunoglobulin G-binding protein H precursor | *Streptococcus pyogenes* serotype M1 | 376 | (Gomi et al., 1990) |
| Protein sbi | sbi | Immunoglobulin G-binding protein sbi precursor | *Staphylococcus aureus* (strain NCTC 8325-4) | 436 | (Zhang et al., 1998) |
| Allergen Asp fl 1 | | Allergen Asp fl 1 causes an allergic reaction in human. Binds to IgE and IgG | *Aspergillus flavus* | 32 | |
| Allergen Asp fl 2 | | Allergen Asp fl 2 causes an allergic reaction in human. Binds to IgE and IgG | *Aspergillus flavus* | 20 | |
| Allergen Asp fl 3 | | Allergen Asp fl 3 causes an allergic reaction in human. Binds to IgE and IgG | *Aspergillus flavus* | 32 | |
| Fc-epsilon RI | | IgE receptor displayed on Mast cells, Eosinophils and Basophils | Homo sapiens (Human) | | |
| Fc-alpha RI (CD86) | | IgA (IgA1, IgA2) receptor displayed on Macrophages | Homo sapiens (Human) | | |
| C1q | C1QA NP_057075.1, C1QB NP_000482.3, C1QC NP_758957.1 | C1q is multimeric complex that binds to antibody Fc composed of 6 A chains, 6 B chains and 6 C chains | Homo sapiens (Human) | | |

III. Methods for Screening Antibody FC Domains

In certain aspects there are methods for identifying antibody Fc domains with a specific affinity for a target ligand (e.g., an antibody-binding polypeptide, such as an Fc receptor). Such methods are described herein, as well as in PCT Publn. WO 2008/137475, which is hereby specifically incorporated by reference in its entirety.

The polypeptides screened may comprise a large library of diverse candidate Fc domains, or, alternatively, may comprise particular classes of Fc domains (e.g., engineered point mutations or amino acid insertions) selected with an eye towards structural attributes that are believed to make them more likely to bind the target ligand. In one embodiment, the candidate polypeptide may be an intact antibody, or a fragment or portion thereof comprising an Fc domain.

To identify a candidate Fc domain capable of binding a target ligand, one may carry out the steps of: providing a population of Gram-negative bacterial cells that each expresses a distinct antibody Fc domain; admixing the bacteria and at least a first labeled or immobilized target ligand (FcR polypeptide) capable of contacting the antibody Fc domain; and identifying at least a first bacterium expressing a molecule capable of binding the target ligand.

In some aspects of the aforementioned method, the binding between antibody Fc domain and a labeled FcR polypeptide will prevent diffusion out of a bacterial cell. In this way, molecules of the labeled ligand can be retained in the periplasm of the bacterium comprising a permeabilized outer membrane. Alternatively, the periplasm can be removed, whereby the Fc domain will cause retention of the bound candidate molecule since Fc domains are shown to associate with the inner membrane. The labeling may then be used to isolate the cell expressing a binding polypeptide capable of binding the FcR polypeptide, and the gene encoding the Fc domain polypeptide may be isolated. The molecule capable of binding the target ligand may then be produced in large quantities using in vivo or ex vivo expression methods, and then used for any desired application, for example, for diagnostic or therapeutic applications. Furthermore, it will be understood that isolated antibody Fc domains identified may be used to construct an antibody fragment or full-length antibody comprising an antigen binding domain.

In further embodiments, methods of screening may comprise at least two rounds of selection wherein the sub-population of bacterial cells obtained in the first round of selection is subjected to at least a second round of selection based on the binding of the candidate antibody Fc domain to an FcR. Furthermore in some aspects the sub-population of bacterial cells obtained in the first round of selection may be grown under permissive conditions prior to a second selection (to expand the total number of cells). Thus, in some aspects, methods may comprise 2, 3, 4, 5, 6, 7, 8, 9, 10 or more rounds of selection. Furthermore, in some aspects, a sub-population of bacterial cells obtained from each round of selection will be grown under permissive conditions before a subsequent round of selection. Cells isolated following one or more such rounds of selection may be subjected to additional rounds of mutagenesis. In some cases, selection will be performed after removing FcR polypeptide that is not bound to the antibody. Furthermore, in some cases the stringency of selection may be modified by adjusting the pH, salt concentration, or temperature of a solution comprising bacteria that display antibodies. Thus, in some aspects, it may be preferred that a bacterial cell of the invention is grown at a sub-physiological temperature, such as at about 25° C.

In still further aspects, a method of producing a bacterial cell according to the invention may be further defined as a method of producing a nucleic acid sequence encoding an Fc domain that binds to at least a first FcR. Thus, a bacterial cell produced by the methods herein may be used to clone a nucleic acid sequence encoding the Fc domain having a specific affinity for an FcR polypeptide. Methods for isolating and amplifying such a nucleic acid from a cell for example by PCR are well known in the art and further described below. Thus, a nucleic acid sequence produced by the foregoing methods is included as part of the instant invention. Furthermore, such a sequence may be expressed in a cell to produce an Fc domain having a specific affinity for an FcR. Thus, in some aspects, the invention provides a method for producing an Fc domain having a specific affinity for an FcR. Furthermore, the invention includes antibody Fc domains produced by the methods of the invention. It will be understood however that the antibody Fc domains produced by such a screen may be combined with antibody variable regions that have an affinity for a particular target ligand and these antibodies are also included as part of the invention.

B. Periplasmic Expression of Antibody Fc Domains

In some embodiments, a polypeptide comprising an antibody Fc domain may be expressed in the periplasmic space of Gram-negative bacteria. Furthermore, in some aspects an antibody Fc domain may be anchored to the periplasmic face of the inner membrane. Methods and compositions for the anchoring of polypeptides to the inner membrane of Gram-negative bacteria have previously been described (U.S. Pat. Nos. 7,094,571, 7,419,783, 7,611,866 and U.S. Patent Publn. No. 2003/0219870; Harvey et al., 2004; Harvey et al., 2006). For example, an Fc domain may be directly fused to a membrane spanning or membrane bound polypeptide or may interact (e.g., via protein-protein interactions) with a membrane spanning or membrane bound polypeptide. Such a technique may be termed "Anchored Periplasmic Expression" or "APEx." In some cases, a Gram-negative bacterial cell may be defined as an *E. coli* cell. Furthermore, in some aspects a Gram-negative bacterial cell may be defined as a genetically engineered bacterial cell, such as a Jude-1 strain of *E. coli*.

A fusion protein may comprise an N-terminal or C-terminal fusion with an Fc domain and in some case may comprise additional linker amino acids between the membrane anchoring polypeptide and the Fc domain. In certain specific cases, a membrane anchoring polypeptide may be the first six amino acids encoded by the *E. coli* NlpA gene, one or more transmembrane α-helices from an *E. coli* inner membrane protein, a gene III protein of filamentous phage or a fragment thereof, or an inner membrane lipoprotein or fragment thereof. Thus, as an example, a membrane anchoring polypeptide may be an inner membrane lipoprotein or fragment thereof such as from AraH, MglC, MalF, MalG, MalC, MalD, RbsC, RbsC, ArtM, ArtQ, GlnP, ProW, HisM, HisQ, LivH, LivM, LivA, LivE, DppB, DppC, OppB, AmiC, AmiD, BtuC, ThuD, FecC, FecD, FecR, FepD, NikB, NikC, CysT, CysW, UgpA, UgpE, PstA, PstC, PotB, PotC, PotH, Pod, ModB, NosY, PhnM, LacY, SecY, TolC, DsbB, DsbD, TouB, TatC, CheY, TraB, ExbD, ExbB, or Aas.

In still further cases, a population of Gram-negative bacteria according to the invention may be defined as comprising at least about $1 \times 10^3$, $1 \times 10^4$, $1 \times 10^5$, $1 \times 10^6$, $1 \times 10^7$, $1 \times 10^8$, $1 \times 10^9$ or more distinct antibodies Fc domains. In some specific cases, a population of Gram-negative bacterial cells may be produced by a method comprising the steps of: (a) preparing a plurality of nucleic acid sequences encoding a plurality of distinct antibody Fc domains; and (b) transforming a population of Gram-negative bacteria with said nucleic acids wherein the Gram-negative bacteria comprise a plurality of antibody Fc domains expressed in the periplasm.

C. Permeabilization of the Outer Membrane

Methods for disrupting, permeabilizing, or removing the outer membrane of bacteria are well known in the art, for example, see U.S. Pat. No. 7,094,571. For instance, prior to contacting the bacterial cells with an FcR polypeptide, the outer membrane of the bacterial cell may be treated with hyperosmotic conditions, physical stress, lysozyme, EDTA, a digestive enzyme, a chemical that disrupts the outer membrane, by infecting the bacterium with a phage, or a combination of the foregoing methods. Thus, in some cases, the outer membrane may be disrupted by lysozyme and EDTA treatment. Furthermore, in certain embodiments, the bacterial outer membrane may be removed entirely.

Methods may be employed for increasing the permeability of the outer membrane to one or more labeled ligands. This can allow screening access of labeled ligands otherwise unable to cross the outer membrane. However, certain classes of molecules, for example, hydrophobic antibiotics larger than the 650 Da exclusion limit, can diffuse through the bacterial outer membrane itself, independent of membrane porins (Farmer et al., 1999). The process may actually permeabilize the membrane on so doing (Jouenne and Junter, 1990). Also, certain long chain phosphate polymers (100 Pi) appear to bypass the normal molecular sieving activity of the outer membrane altogether (Rao and Torriani, 1988).

While conditions have been identified that lead to the permeation of ligands into the periplasm without loss of viability or release of the expressed proteins from the cells, the invention may be carried out without maintenance of the outer membrane. For Fc domains expressed or anchored in the periplasmic space, the need for maintenance of the outer membrane (as a barrier to prevent the leakage of the binding protein from the cell) to detect bound labeled ligand is removed. As a result, cells expressing binding proteins anchored to the outer (periplasmic) face of the cytoplasmic membrane can be labeled simply by incubating with a solution of labeled ligand in cells that either have a partially permeabilized membrane or a nearly completely removed outer membrane.

Treatments, such as hyperosmotic shock, can improve labeling significantly. It is known that many agents, including calcium ions (Bukau et al., 1985) and even Tris buffer (Irvin et al., 1981), alter the permeability of the outer-membrane. Further, phage infection stimulates the labeling process. Both the filamentous phage inner membrane protein pIII and the large multimeric outer membrane protein pIV can alter membrane permeability (Boeke et al., 1982) with mutants in pIV known to improve access to maltodextrins normally excluded (Marciano et al., 1999). Using the techniques of the invention, comprising a judicious combination of strain, salt, and phage, a high degree of permeability may be achieved (Daugherty et al., 1999). Cells comprising anchored or periplasm-associated polypeptides bound to labeled ligands can then be easily isolated from cells that express binding proteins without affinity for the labeled ligand using flow cytometry or other related techniques. However, in some cases, it will be desired to use less disruptive techniques in order to maintain the viability of cells. EDTA and lysozyme treatments may also be useful in this regard.

D. Labeled Target Ligands

As indicated above, it will typically be desired to provide an FcR polypeptide that has been labeled with one or more detectable agent(s). This can be carried out, for example, by linking the ligand to at least one detectable agent to form a conjugate. For example, it is conventional to link or covalently bind or complex at least one detectable molecule or moiety. A "label" or "detectable label" is a compound and/or element that can be detected due to specific functional properties, and/or chemical characteristics, the use of which allows the ligand to which it is attached to be detected, and/or further quantified if desired. Examples of labels that could be used include, but are not limited to, enzymes, radiolabels, haptens, fluorescent labels, phosphorescent molecules, chemiluminescent molecules, chromophores, luminescent molecules, photoaffinity molecules, colored particles, or ligands, such as biotin.

In one embodiment of the invention, a visually-detectable marker is used such that automated screening of cells for the label can be carried out. Examples of agents that may be detected by visualization with an appropriate instrument are known in the art, as are methods for their attachment to a desired ligand (see, e.g., U.S. Pat. Nos. 5,021,236; 4,938,948; and 4,472,509, each incorporated herein by reference). Such agents can include paramagnetic ions; radioactive isotopes; fluorochromes; NMR-detectable substances; and substances for X-ray imaging. In particular, fluorescent labels are beneficial in that they allow use of flow cytometry for isolation of cells expressing a desired binding protein or antibody.

Another type of FcR conjugate is where the ligand is linked to a secondary binding molecule and/or to an enzyme (an enzyme tag) that will generate a colored product upon contact with a chromogenic substrate. Examples of such enzymes include urease, alkaline phosphatase, (horseradish) hydrogen peroxidase, or glucose oxidase. In such instances, it will be desired that cells selected remain viable. Preferred secondary binding ligands are biotin and/or avidin and streptavidin compounds. The use of such labels is well known to those of skill in the art and are described, for example, in U.S. Pat. Nos. 3,817,837; 3,850,752; 3,939,350; 3,996,345; 4,277,437; 4,275,149; and 4,366,241, each incorporated herein by reference.

Molecules containing azido groups may be used to form covalent bonds to proteins through reactive nitrene intermediates that are generated by low intensity ultraviolet light (Potter and Haley, 1983). In particular, 2- and 8-azido analogues of purine nucleotides have been used as site-directed photoprobes to identify nucleotide-binding proteins in crude cell extracts (Owens and Haley, 1987; Atherton et al., 1985). The 2- and 8-azido nucleotides have also been used to map nucleotide-binding domains of purified proteins (Khatoon et al., 1989; King et al., 1989; Dholakia et al., 1989) and may be used as ligand binding agents.

Labeling can be carried out by any of the techniques well known to those of skill in the art. For instance, FcR polypeptides can be labeled by contacting the ligand with the desired label and a chemical oxidizing agent, such as sodium hypochlorite, or an enzymatic oxidizing agent, such as lactoperoxidase. Similarly, a ligand exchange process could be used. Alternatively, direct labeling techniques may be used, e.g., by incubating the label, a reducing agent such as $SNCl_2$, a buffer solution such as sodium-potassium phthalate solution, and the ligand. Intermediary functional groups on the ligand could also be used, for example, to bind labels to a ligand in the presence of diethylenetriaminepentaacetic acid (DTPA) or ethylene diaminetetracetic acid (EDTA).

Other methods are also known in the art for the attachment or conjugation of a ligand to its conjugate moiety. Some attachment methods involve the use of an organic chelating agent, such as diethylenetriaminepentaacetic acid anhydride (DTPA); ethylenetriaminetetraacetic acid; N-chloro-p-toluenesulfonamide; and/or tetrachloro-3α-6α-diphenylglycouril-3 attached to the ligand (U.S. Pat. Nos. 4,472,509 and 4,938,948, each incorporated herein by reference). FcR polypeptides also may be reacted with an enzyme in the presence of a coupling agent such as glutaraldehyde or periodate. Conjugates with fluorescein markers can be prepared in the presence of these coupling agents or by reaction with an isothiocyanate. In U.S. Pat. No. 4,938,948, imaging of breast tumors is achieved using monoclonal antibodies and the detectable imaging moieties are bound to the antibody using linkers such as methyl-p-hydroxybenzimidate or N-succinimidyl-3-(4-hydroxyphenyl)propionate. In still further aspects an FcR polypeptide may be fused to a reporter protein, such as an enzyme as described supra or a fluorescence protein.

E. Isolation of Bacterial Cells Bound to Labeled Target Ligand

1. Column- or Bead-Based Immobilization

The skilled artisan will understand that methods for selecting cells based upon their interaction (binding) with an FcR are well-known in the art. For example, an FcR may be immobilized on a column or bead (e.g., a magnetic bead) and the bacterial cell binding to the FcR separated by repeated washing of the bead (e.g., magnetic separation) or column. Furthermore, in some aspects a target ligand may be labeled, such as with a fluorophore, a radioisotope, or an enzyme. Thus, bacterial cells may, in some cases, be selected by detecting a label on a bound FcR. Furthermore, in some aspects, bacterial cells may be selected based on binding or lack of binding to two or more FcR polypeptides. For instance, bacteria may be selected that display antibodies that bind to two FcR polypeptides, wherein each FcR is used to select the bacteria sequentially. Conversely, in certain aspects, bacteria may be selected that display antibody Fc domains that bind to one FcR (such as an FcR comprising a first label) but not to a second FcR (e.g., comprising a second label). The foregoing method may be used, for example, to identify antibody Fc domains that bind to a specific FcR but not a second specific FcR.

2. Flow Cytometry

In one embodiment of the invention, fluorescence activated cell sorting (FACS) screening or other automated flow cytometric techniques may be used for the efficient isolation of a bacterial cell comprising a labeled ligand bound to an Fc domain. Instruments for carrying out flow cytometry are known to those of skill in the art and are commercially available to the public. Examples of such instruments include FACS Star Plus, FACScan and FACSort instruments from Becton Dickinson (Foster City, Calif.), Epics C from Coulter Epics Division (Hialeah, Fla.), and MOFLO™ from Cytomation (Colorado Springs, Colo.).

Flow cytometric techniques in general involve the separation of cells or other particles in a liquid sample. Typically, the purpose of flow cytometry is to analyze the separated particles for one or more characteristics thereof, for example, presence of a labeled ligand or other molecule. The basic steps of flow cytometry involve the direction of a fluid sample through an apparatus such that a liquid stream passes through a sensing region. The particles should pass one at a time by the sensor and are categorized based on size, refraction, light scattering, opacity, roughness, shape, fluorescence, etc.

Not only is cell analysis performed by flow cytometry, but so too is sorting of cells. In U.S. Pat. No. 3,826,364, an apparatus is disclosed which physically separates particles, such as functionally different cell types. In this machine, a laser provides illumination that is focused on the stream of particles by a suitable lens or lens system so that there is highly localized scatter from the particles therein. In addition, high intensity source illumination is directed onto the stream of particles for the excitation of fluorescent particles in the stream. Certain particles in the stream may be selectively charged and then separated by deflecting them into designated receptacles. A classic form of this separation is via fluorescent-tagged antibodies, which are used to mark one or more cell types for separation.

Other examples of methods for flow cytometry include, but are not limited to, those described in U.S. Pat. Nos. 4,284,412; 4,989,977; 4,498,766; 5,478,722; 4,857,451; 4,774,189; 4,767,206; 4,714,682; 5,160,974; and 4,661,913, each of which are specifically incorporated herein by reference.

For the present invention, an important aspect of flow cytometry is that multiple rounds of screening can be carried out sequentially. Cells may be isolated from an initial round of sorting and immediately reintroduced into the flow cytometer and screened again to improve the stringency of the screen. Another advantage known to those of skill in the art is that nonviable cells can be recovered using flow cytometry. Since flow cytometry is essentially a particle sorting technology, the ability of a cell to grow or propagate is not necessary. Techniques for the recovery of nucleic acids from such non-viable cells are well known in the art and may include, for example, use of template-dependent amplification techniques including PCR.

F. Cloning of Fc Domain Coding Sequences

After a bacterial cell is identified that produces molecules of the desired specificity, affinity, and/or activity, the corresponding coding sequence may be cloned. In this manner, DNA encoding the molecule can be isolated and sequenced using conventional procedures (e.g., by using oligonucleotide probes that are capable of binding specifically to genes encoding the antibody or binding protein). It will be understood by those of skill in the art that nucleic acids may be cloned from viable or inviable cells. In the case of inviable cells, for example, it may be desired to use amplification of the cloned DNA, for example, using PCR. This may also be carried out using viable cells either with or without further growth of cells.

Once isolated, the antibody Fc domain DNA may be placed into expression vectors, which can then be transfected into host cells, such as bacteria. The DNA also may be modified, for example, by the addition of sequence for human heavy and light chain variable domains, or by covalently joining to the immunoglobulin coding sequence all or part of the coding sequence for a non-immunoglobulin polypeptide. In that manner, "chimeric" or "hybrid" binding proteins are prepared to have the desired binding specificity. For instance, an identified antibody Fc domain may be fused to a therapeutic polypeptide or a toxin and used to target cells (in vitro or in vivo) that express a particular FcR.

Chimeric or hybrid Fc domains also may be prepared in vitro using known methods in synthetic protein chemistry, including those involving crosslinking agents. For example, targeted-toxins may be constructed using a disulfide exchange reaction or by forming a thioether bond. Examples of suitable reagents for this purpose include iminothiolate and methyl-4-mercaptobutyrimidate.

IV. Nucleic Acid-Based Expression Systems

Nucleic acid-based expression systems may find use, in certain embodiments of the invention, for the expression of recombinant proteins. For example, one embodiment of the invention involves transformation of Gram-negative bacteria with the coding sequences for an antibody Fc domain, or preferably a plurality of distinct Fc domains.

A. Methods of Nucleic Acid Delivery

Certain aspects of the invention may comprise delivery of nucleic acids to target cells (e.g., Gram-negative bacteria). For example, bacterial host cells may be transformed with nucleic acids encoding candidate Fc domains potentially capable binding an FcR. In particular embodiments of the invention, it may be desired to target the expression to the periplasm of the bacteria. Transformation of eukaryotic host cells may similarly find use in the expression of various candidate molecules identified as capable of binding a target ligand.

Suitable methods for nucleic acid delivery for transformation of a cell are believed to include virtually any method by which a nucleic acid (e.g., DNA) can be introduced into a cell, or even an organelle thereof. Such methods include, but are not limited to, direct delivery of DNA, such as by injection (U.S. Pat. Nos. 5,994,624; 5,981,274; 5,945,100; 5,780,448; 5,736,524; 5,702,932; 5,656,610; 5,589,466; and 5,580,859, each incorporated herein by reference), including microinjection (Harland and Weintraub, 1985; U.S. Pat. No. 5,789,215, incorporated herein by reference); by electroporation (U.S. Pat. No. 5,384,253, incorporated herein by reference); by calcium phosphate precipitation (Graham and Van Der Eb, 1973; Chen and Okayama, 1987; Rippe et al., 1990); by using DEAE-dextran followed by polyethylene glycol (Gopal, 1985); by direct sonic loading (Fechheimer et al., 1987); by liposome mediated transfection (Nicolau and Sene, 1982; Fraley et al., 1979; Nicolau et al., 1987; Wong et al., 1980; Kaneda et al., 1989; Kato et al., 1991); by microprojectile bombardment (PCT Publn. Nos. WO 94/09699 and 95/06128; U.S. Pat. Nos. 5,610,042; 5,322,783; 5,563,055; 5,550,318; 5,538,877; and 5,538,880, and each incorporated herein by reference); or by agitation with silicon carbide fibers (Kaeppler et al., 1990; U.S. Pat. Nos. 5,302,523 and 5,464,765, each incorporated herein by reference); by desiccation/inhibition-mediated DNA uptake (Potrykus et al., 1985). Through the application of techniques such as these, cells may be stably or transiently transformed.

B. Vectors

Vectors may find use with the current invention, for example, in the transformation of a cell with a nucleic acid sequence encoding a candidate Fc domain. In one embodiment of the invention, an entire heterogeneous "library" of nucleic acid sequences encoding polypeptides may be introduced into a population of cells, thereby allowing screening of the entire library. The term "vector" is used to refer to a carrier nucleic acid molecule into which a nucleic acid sequence can be inserted for introduction into a cell where it can be replicated. A nucleic acid sequence can be "exogenous" or "heterologous," which means that it is foreign to the cell into which the vector is being introduced or that the sequence is homologous to a sequence in the cell but in a position within the host cell nucleic acid in which the sequence is ordinarily not found. Vectors include plasmids, cosmids, and viruses (e.g., bacteriophage). One of skill in the art may construct a vector through standard recombinant techniques, which are described in Maniatis et al., 1988 and Ausubel et al., 1994, both of which are incorporated herein by reference.

The term "expression vector" refers to a vector containing a nucleic acid sequence coding for at least part of a gene product capable of being transcribed. In some cases, RNA molecules are then translated into a protein, polypeptide, or peptide. Expression vectors can contain a variety of "control sequences," which refer to nucleic acid sequences necessary for the transcription and possibly translation of an operably linked coding sequence in a particular host organism. In addition to control sequences that govern transcription and translation, vectors and expression vectors may contain nucleic acid sequences that serve other functions as well.

1. Promoters and Enhancers

A "promoter" is a control sequence that is a region of a nucleic acid sequence at which initiation and rate of transcription are controlled. It may contain genetic elements to which regulatory proteins and molecules may bind, such as RNA polymerase and other transcription factors. The phrases "operatively positioned," "operatively linked," "under control," and "under transcriptional control" mean that a promoter is in a correct functional location and/or orientation in relation to a nucleic acid sequence to control transcriptional initiation and/or expression of that sequence. A promoter may or may not be used in conjunction with an "enhancer," which refers to a cis-acting regulatory sequence involved in the transcriptional activation of a nucleic acid sequence. Those of skill in the art of molecular biology generally are familiar with the use of promoters, enhancers, and cell type combinations for protein expression, for example, see Sambrook et al. (1989), incorporated herein by reference.

2. Initiation Signals

A specific initiation signal also may be required for efficient translation of coding sequences. These signals include the ATG initiation codon or adjacent sequences. Exogenous translational control signals, including the ATG initiation codon, may need to be provided. One of ordinary skill in the art would readily be capable of determining this and providing the necessary signals. It is well known that the initiation codon must be "in-frame" with the reading frame of the desired coding sequence to ensure translation of the entire insert. The exogenous translational control signals and initiation codons can be either natural or synthetic. The efficiency of expression may be enhanced by the inclusion of appropriate transcription enhancer elements.

3. Multiple Cloning Sites

Vectors can include a multiple cloning site (MCS), which is a nucleic acid region that contains multiple restriction enzyme sites, any of which can be used in conjunction with standard recombinant technology to digest the vector (see Carbonelli et al., 1999, Levenson et al., 1998, and Cocea, 1997, incorporated herein by reference). "Restriction enzyme digestion" refers to catalytic cleavage of a nucleic acid molecule with an enzyme that functions only at specific locations in a nucleic acid molecule. Many of these restriction enzymes are commercially available. Frequently, a vector is linearized or fragmented using a restriction enzyme that cuts within the MCS to enable exogenous sequences to be ligated to the vector. "Ligation" refers to the process of forming phosphodiester bonds between two nucleic acid fragments, which may or may not be contiguous with each other. Techniques involving restriction enzymes and ligation reactions are well known to those of skill in the art of recombinant technology.

4. Termination Signals

The vectors or constructs prepared in accordance with the present invention will generally comprise at least one termination signal. A "termination signal" or "terminator" is comprised of the DNA sequences involved in specific termination of an RNA transcript by an RNA polymerase. Thus, in certain embodiments, a termination signal that ends the production of an RNA transcript is contemplated. A terminator may be necessary in vivo to achieve desirable message levels. Terminators contemplated for use in the invention include any known terminator of transcription known to one of ordinary skill in the art, including, but not limited to, rho dependent or rho independent terminators. In certain embodiments, the termination signal may be a lack of transcribable or translatable sequence, such as due to a sequence truncation.

5. Origins of Replication

In order to propagate a vector in a host cell, it may contain one or more origins of replication sites (often termed "ori"), which is a specific nucleic acid sequence at which replication is initiated.

6. Selectable and Screenable Markers

In certain embodiments of the invention, cells containing a nucleic acid construct of the present invention may be identified in vitro or in vivo by including a marker in the expression vector. Such markers would confer an identifiable change to the cell permitting easy identification of cells containing the expression vector. Generally, a selectable marker is one that confers a property that allows for selection. A positive selectable marker is one in which the presence of the marker allows for its selection, while a negative selectable marker is one in which its presence prevents its selection. An example of a positive selectable marker is a drug resistance marker.

Usually the inclusion of a drug selection marker aids in the cloning and identification of transformants, for example, genes that confer resistance to neomycin, puromycin, hygromycin, DHFR, GPT, zeocin and histidinol are useful selectable markers. In addition to markers conferring a phenotype that allows for the discrimination of transformants based on the implementation of conditions, other types of markers including screenable markers, such as GFP, whose basis is colorimetric analysis, are also contemplated. Alternatively, screenable enzymes such as chloramphenicol acetyltransferase (CAT) may be utilized. One of skill in the art would also know how to employ immunologic markers, possibly in conjunction with FACS analysis. The marker used is not believed to be important, so long as it is capable of being expressed simultaneously with the nucleic acid encoding a gene product. Further examples of selectable and screenable markers are well known to one of skill in the art.

C. Host Cells

In the context of expressing a heterologous nucleic acid sequence, "host cell" refers to a prokaryotic cell, and it includes any transformable organism that is capable of replicating a vector and/or expressing a heterologous gene encoded by a vector. A host cell can, and has been, used as a recipient for vectors. A host cell may be "transfected" or "transformed," which refers to a process by which exogenous nucleic acid is transferred or introduced into the host cell. A transformed cell includes the primary subject cell and its progeny.

In particular embodiments of the invention, a host cell is a Gram-negative bacterial cell. These bacteria are suited for use with the invention in that they possess a periplasmic space between the inner and outer membrane and, particularly, the aforementioned inner membrane between the periplasm and cytoplasm, which is also known as the cytoplasmic membrane. As such, any other cell with such a periplasmic space could be used in accordance with the invention. Examples of Gram-negative bacteria that may find use with the invention may include, but are not limited to, *E. coli, Pseudomonas aeruginosa, Vibrio cholera, Salmonella typhimurium, Shigella flexneri, Haemophilus influenza, Bordotella pertussi, Erwinia amylovora, Rhizobium* sp.

An appropriate host can be determined by one of skill in the art based on the vector backbone and the desired result. A plasmid or cosmid, for example, can be introduced into a prokaryote host cell for replication of many vectors. Bacterial cells used as host cells for vector replication and/or expression include DH5α, JM109, and KC8, as well as a number of commercially available bacterial hosts such as SURE® Competent Cells and SOLOPACK™ Gold Cells (Stratagene®, La Jolla). Alternatively, bacterial cells such as *E. coli* LE392 could be used as host cells for bacteriophage.

Examples of mammalian host cells include Chinese hamster ovary cells (CHO-K1; ATCC CCL61), rat pituitary cells (GH1; ATCC CCL82), HeLa S3 cells (ATCC CCL2.2), rat hepatoma cells (H-4-II-E; ATCCCRL 1548), SV40-transformed monkey kidney cells (COS-1; ATCC CRL 1650), and murine embryonic cells (NIH-3T3; ATCC CRL 1658). The foregoing being illustrative but not limitative of the many possible host organisms known in the art.

Mammalian host cells expressing the polypeptide are cultured under conditions typically employed to culture the parental cell line. Generally, cells are cultured in a standard medium containing physiological salts and nutrients, such as standard RPMI, MEM, IMEM, or DMEM, typically supplemented with 5%-10% serum, such as fetal bovine serum. Culture conditions are also standard, e.g., cultures are incubated at 37° C. in stationary or roller cultures until desired levels of the proteins are achieved.

Many host cells from various cell types and organisms are available and would be known to one of skill in the art. Similarly, a viral vector may be used in conjunction with a prokaryotic host cell, particularly one that is permissive for replication or expression of the vector. Some vectors may employ control sequences that allow it to be replicated and/or expressed in both prokaryotic and eukaryotic cells. One of skill in the art would further understand the conditions under which to incubate all of the above described host cells to maintain them and to permit replication of a vector. Also understood and known are techniques and conditions that would allow large-scale production of vectors, as well as production of the nucleic acids encoded by vectors and their cognate polypeptides, proteins, or peptides.

D. Expression Systems

Numerous expression systems exist that comprise at least a part or all of the compositions discussed above. Such systems could be used, for example, for the production of a polypeptide product identified in accordance with the invention as capable of binding a particular ligand. Prokaryote-based systems can be employed for use with the present invention to produce nucleic acid sequences, or their cognate polypeptides, proteins, and peptides. Many such systems are commercially and widely available. Other examples of expression systems comprise of vectors containing a strong prokaryotic promoter such as T7, Tac, Trc, BAD, lambda pL, Tetracycline or Lac promoters, the pET Expression System, and an *E. coli* expression system.

In certain aspects of the invention, nucleic acid sequences encoding a polypeptide are disclosed. Depending on which expression system is used, nucleic acid sequences can be selected based on conventional methods. For example, if the polypeptide is derived from a human polypeptide and contains multiple codons that are rarely utilized in *E. coli*, then that may interfere with expression in *E. coli*. Therefore, the respective genes or variants thereof may be codon optimized for *E. coli* expression. Various vectors may be also used to express the protein of interest. Exemplary vectors include, but are not limited, plasmid vectors, viral vectors, transposon, or liposome-based vectors.

V. Protein Purification

Protein purification techniques are well known to those of skill in the art. These techniques involve, at one level, the homogenization and crude fractionation of the cells, tissue, or organ into polypeptide and non-polypeptide fractions. The protein or polypeptide of interest may be further purified using chromatographic and electrophoretic techniques to achieve partial or complete purification (or purification to homogeneity) unless otherwise specified. Analytical methods particularly suited to the preparation of a pure peptide are ion-exchange chromatography, size-exclusion chromatography, reverse phase chromatography, hydroxyapatite chromatography, polyacrylamide gel electrophoresis, affinity chromatography, immunoaffinity chromatography, and isoelectric focusing. A particularly efficient method of purifying peptides is fast-performance liquid chromatography (FPLC) or even high-performance liquid chromatography (HPLC). As is generally known in the art, it is believed that the order of conducting the various purification steps may be changed, or that certain steps may be omitted, and still result in a suitable method for the preparation of a substantially purified protein or peptide.

A purified protein or peptide is intended to refer to a composition, isolatable from other components, wherein the protein or peptide is purified to any degree relative to its naturally-obtainable state. An isolated or purified protein or peptide, therefore, also refers to a protein or peptide free from the environment in which it may naturally occur. Generally, "purified" will refer to a protein or peptide composition that has been subjected to fractionation to remove various other components, and which composition substantially retains its expressed biological activity. Where the term "substantially purified" is used, this designation will refer to a composition in which the protein or peptide forms the major component of the composition, such as constituting about 50%, about 60%, about 70%, about 80%, about 90%, about 95%, or more of the proteins in the composition.

Various methods for quantifying the degree of purification of the protein or peptide are known to those of skill in the art in light of the present disclosure. These include, for example, determining the specific activity of an active fraction, or assessing the amount of polypeptides within a fraction by SDS/PAGE analysis. A preferred method for assessing the purity of a fraction is to calculate the specific activity of the fraction, to compare it to the specific activity of the initial extract, and to thus calculate the degree of purity therein, assessed by a "fold purification number." The actual units used to represent the amount of activity will, of course, be dependent upon the particular assay technique chosen to follow the purification, and whether or not the expressed protein or peptide exhibits a detectable activity.

There is no general requirement that the protein or peptide will always be provided in its most purified state. Indeed, it is contemplated that less substantially purified products may have utility in certain embodiments. Partial purification may be accomplished by using fewer purification steps in combination, or by utilizing different forms of the same general purification scheme. For example, it is appreciated that a cation-exchange column chromatography performed utilizing an HPLC apparatus will generally result in a greater "fold" purification than the same technique utilizing a low pressure chromatography system. Methods exhibiting a lower degree of relative purification may have advantages in total recovery of protein product, or in maintaining the activity of an expressed protein.

Affinity chromatography is a chromatographic procedure that relies on the specific affinity between a substance to be isolated and a molecule to which it can specifically bind. This is a receptor-ligand type of interaction. The column material is synthesized by covalently coupling one of the binding partners to an insoluble matrix. The column material is then able to specifically adsorb the substance from the solution. Elution occurs by changing the conditions to those in which binding will not occur (e.g., altered pH, ionic strength, temperature, etc.). The matrix should be a substance that does not adsorb molecules to any significant extent and that has a broad range of chemical, physical, and thermal stability. The ligand should be coupled in such a way as to not affect its binding properties. The ligand should also provide relatively tight binding. It should be possible to elute the substance without destroying the sample or the ligand.

Size-exclusion chromatography (SEC) is a chromatographic method in which molecules in solution are separated based on their size, or in more technical terms, their hydrodynamic volume. It is usually applied to large molecules or macromolecular complexes, such as proteins and industrial polymers. Typically, when an aqueous solution is used to transport the sample through the column, the technique is known as gel filtration chromatography, versus the name gel permeation chromatography, which is used when an organic solvent is used as a mobile phase. The underlying principle of SEC is that particles of different sizes will elute (filter) through a stationary phase at different rates. This results in the separation of a solution of particles based on size. Provided that all the particles are loaded simultaneously or near simultaneously, particles of the same size should elute together.

High-performance liquid chromatography (or high-pressure liquid chromatography, HPLC) is a form of column chromatography used frequently in biochemistry and analytical chemistry to separate, identify, and quantify compounds. HPLC utilizes a column that holds chromatographic packing material (stationary phase), a pump that moves the mobile phase(s) through the column, and a detector that shows the retention times of the molecules. Retention time varies depending on the interactions between the stationary phase, the molecules being analyzed, and the solvent(s) used.

VI. Pharmaceutical Compositions

Where clinical application of a pharmaceutical composition containing a polypeptide or antibody is undertaken, it will generally be beneficial to prepare a pharmaceutical or therapeutic composition appropriate for the intended application. Generally, pharmaceutical compositions may comprise an effective amount of one or more polypeptide or additional agents dissolved or dispersed in a pharmaceutically acceptable carrier. In certain embodiments, pharmaceutical compositions may comprise, for example, at least about 0.1% of a polypeptide or antibody. In other embodiments, a polypeptide or antibody may comprise between about 2% to about 75% of the weight of the unit, or between about 25% to about 60%, for example, and any range derivable therein. The amount of active compound(s) in each therapeutically useful composition may be prepared in such a way that a suitable dosage will be obtained in any given unit dose of the compound. Factors, such as solubility, bioavailability, biological half-life, route of administration, product shelf life, as well as other pharmacological considerations, will be contemplated by one skilled in the art of preparing such pharmaceutical formulations, and as such, a variety of dosages and treatment regimens may be desirable.

The phrases "pharmaceutical or pharmacologically acceptable" refers to molecular entities and compositions that do not produce an adverse, allergic, or other untoward reaction when administered to an animal, such as a human, as appropriate. The preparation of a pharmaceutical composition comprising an antibody or additional active ingredient will be known to those of skill in the art in light of the present disclosure, as exemplified by Remington's Pharmaceutical Sciences, 18th Ed., 1990, incorporated herein by reference. Moreover, for animal (e.g., human) administration, it will be understood that preparations should meet sterility, pyrogenicity, general safety, and purity standards as required by FDA Office of Biological Standards.

Further in accordance with certain aspects of the present invention, the composition suitable for administration may be provided in a pharmaceutically acceptable carrier with or without an inert diluent. The carrier should be assimilable and includes liquid, semi-solid, i.e., pastes, or solid carriers. Examples of carriers or diluents include fats, oils, water, saline solutions, lipids, liposomes, resins, binders, fillers, and the like, or combinations thereof. As used herein, "pharmaceutically acceptable carrier" includes any and all aqueous solvents (e.g., water, alcoholic/aqueous solutions, ethanol, saline solutions, parenteral vehicles, such as sodium chloride, Ringer's dextrose, etc.), non-aqueous solvents (e.g., propylene glycol, polyethylene glycol, vegetable oil, and injectable organic esters, such as ethyloleate), dispersion media, coatings (e.g., lecithin), surfactants, antioxidants, preservatives (e.g., antibacterial or antifungal agents, antioxidants, chelating agents, inert gases, parabens (e.g., methylparabens, propylparabens), chlorobutanol, phenol, sorbic acid, thimerosal), isotonic agents (e.g., sugars, sodium chloride), absorption delaying agents (e.g., aluminum monostearate, gelatin), salts, drugs, drug stabilizers (e.g., buffers, amino acids, such as glycine and lysine, carbohydrates, such as dextrose, mannose, galactose, fructose, lactose, sucrose, maltose, sorbitol, mannitol, etc), gels, binders, excipients, disintegration agents, lubricants, sweetening agents, flavoring agents, dyes, fluid and nutrient replenishers, such like materials and combinations thereof, as would be known to one of ordinary skill in the art. Except insofar as any conventional media, agent, diluent, or carrier is detrimental to the recipient or to the therapeutic effectiveness of the composition contained therein, its use in administrable composition for use in practicing the methods is appropriate. The pH and exact concentration of the various components in a pharmaceutical composition are adjusted according to well-known parameters. In accordance with certain aspects of the present invention, the composition is combined with the carrier in any convenient and practical manner, i.e., by solution, suspension, emulsification, admixture, encapsulation, absorption, grinding, and the like. Such procedures are routine for those skilled in the art.

Certain embodiments of the present invention may comprise different types of carriers depending on whether it is to be administered in solid, liquid, or aerosol form, and whether it needs to be sterile for the route of administration, such as injection. The compositions can be formulated for administration intravenously, intradermally, transdermally, intrathecally, intraarterially, intraperitoneally, intranasally, intravaginally, intrarectally, intramuscularly, subcutaneously, mucosally, orally, topically, locally, by inhalation (e.g., aerosol inhalation), by injection, by infusion, by continuous infusion, by localized perfusion bathing target cells directly, via a catheter, via a lavage, in lipid compositions (e.g., liposomes), or by other methods or any combination of the forgoing as would be known to one of ordinary skill in the art (see, for example, Remington's Pharmaceutical Sciences, 18th Ed., 1990, incorporated herein by reference). Typically, such compositions can be prepared as either liquid solutions or suspensions; solid forms suitable for use to prepare solutions or suspensions upon the addition of a liquid prior to injection can also be prepared; and, the preparations can also be emulsified.

The polypeptides may be formulated into a composition in a free base, neutral, or salt form. Pharmaceutically acceptable salts include the acid addition salts, e.g., those formed with the free amino groups of a proteinaceous composition, or which are formed with inorganic acids, such as, for example, hydrochloric or phosphoric acids, or such organic acids as acetic, oxalic, tartaric, or mandelic acid. Salts formed with the free carboxyl groups can also be derived from inorganic bases, such as, for example, sodium, potassium, ammonium, calcium, or ferric hydroxides; or such organic bases as isopropylamine, trimethylamine, histidine, or procaine.

In further embodiments, the present invention may concern the use of a pharmaceutical lipid vehicle composition that includes polypeptides, one or more lipids, and an aqueous solvent. As used herein, the term "lipid" will be defined to include any of a broad range of substances that is characteristically insoluble in water and extractable with an organic solvent. This broad class of compounds is well known to those of skill in the art, and as the term "lipid" is used herein, it is not limited to any particular structure. Examples include compounds that contain long-chain aliphatic hydrocarbons and their derivatives. A lipid may be naturally occurring or synthetic (i.e., designed or produced by man). However, a lipid is usually a biological substance. Biological lipids are well known in the art, and include for example, neutral fats, phospholipids, phosphoglycerides, steroids, terpenes, lysolipids, glycosphingolipids, glycolipids, sulphatides, lipids with ether- and ester-linked fatty acids, polymerizable lipids, and combinations thereof. Of course, compounds other than those specifically described herein that are understood by one of skill in the art as lipids are also encompassed by the compositions and methods.

One of ordinary skill in the art would be familiar with the range of techniques that can be employed for dispersing a composition in a lipid vehicle. For example, the polypeptide or a fusion protein thereof may be dispersed in a solution containing a lipid, dissolved with a lipid, emulsified with a lipid, mixed with a lipid, combined with a lipid, covalently bonded to a lipid, contained as a suspension in a lipid, contained or complexed with a micelle or liposome, or otherwise associated with a lipid or lipid structure by any means known to those of ordinary skill in the art. The dispersion may or may not result in the formation of liposomes.

The term "unit dose" or "dosage" refers to physically discrete units suitable for use in a subject, each unit containing a predetermined quantity of the therapeutic composition calculated to produce the desired responses discussed above in association with its administration, i.e., the appropriate route and treatment regimen. The quantity to be administered, both according to number of treatments and unit dose, depends on the effect desired. The actual dosage amount of a composition of the present embodiments administered to a patient or subject can be determined by physical and physiological factors, such as body weight, the age, health, and sex of the subject, the type of disease being treated, the extent of disease penetration, previous or concurrent therapeutic interventions, idiopathy of the patient, the route of administration, and the potency, stability, and toxicity of the particular therapeutic substance. In other non-limiting examples, a dose may also comprise from about 1 microgram/kg/body weight, about 5 microgram/kg/body weight, about 10 microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, about 5 milligram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1000 milligram/kg/body weight or more per administration, and any range derivable therein. In non-limiting examples of a derivable range from the numbers listed herein, a range of about 5 milligram/kg/body weight to about 100 milligram/kg/body weight, about 5 microgram/kg/body weight to about 500 milligram/kg/body weight, etc., can be administered, based on the numbers described above. The practitioner responsible for administration will, in any event, determine the concentration of active ingredient(s) in a composition and appropriate dose(s) for the individual subject.

It is not intended that the present invention be limited by the particular nature of the therapeutic preparation. For example, such compositions can be provided in formulations together with physiologically tolerable liquid, gel, or solid carriers, diluents, and excipients. These therapeutic preparations can be administered to mammals for veterinary use, such as with domestic animals, and clinical use in humans in a manner similar to other therapeutic agents. In general, the dosage required for therapeutic efficacy will vary according to the type of use and mode of administration, as well as the particularized requirements of individual subjects. The actual dosage amount of a composition administered to an animal patient can be determined by physical and physiological factors, such as body weight, severity of condition, the type of disease being treated, previous or concurrent therapeutic interventions, idiopathy of the patient, and on the route of administration. Depending upon the dosage and the route of administration, the number of administrations of a preferred dosage and/or an effective amount may vary according to the response of the subject. The practitioner responsible for administration will, in any event, determine the concentration of active ingredient(s) in a composition and appropriate dose(s) for the individual subject.

VII. Methods of Treating

Certain aspects of the present invention provide a polypeptide for treating diseases, such as tumors. Particularly, the polypeptide may have human polypeptide sequences and thus may prevent allergic reactions in human patients, allow repeated dosing, and increase the therapeutic efficacy.

"Treatment" and "treating" refer to administration or application of a therapeutic agent to a subject or performance of a procedure or modality on a subject for the purpose of obtaining a therapeutic benefit of a disease or health-related condition. For example, a treatment may include administration of a pharmaceutically effective amount of an antibody that targets CDC to cancer cells without triggering cancer cell proliferation.

"Subject" and "patient" refer to either a human or non-human, such as primates, mammals, and vertebrates. In particular embodiments, the subject is a human.

The term "therapeutic benefit" or "therapeutically effective" as used throughout this application refers to anything that promotes or enhances the well-being of the subject with respect to the medical treatment of this condition. This includes, but is not limited to, a reduction in the frequency or severity of the signs or symptoms of a disease. For example, treatment of cancer may involve, for example, a reduction in the size of a tumor, a reduction in the invasiveness of a tumor, reduction in the growth rate of the cancer, or prevention of metastasis. Treatment of cancer may also refer to prolonging survival of a subject with cancer.

In some aspects, the disease may be, e.g., a cancer, an infection, or an immune disease. The immune disease may be an autoimmune disease such as, e.g., lupus, rheumatoid arthritis, psoriasis, etc.

Tumors for which the present treatment methods are useful include any malignant cell type, such as those found in a solid tumor or a hematological tumor. Exemplary solid tumors can include, but are not limited to, a tumor of an organ selected from the group consisting of pancreas, colon, cecum, stomach, brain, head, neck, ovary, kidney, larynx, sarcoma, lung, bladder, melanoma, prostate, and breast. Exemplary hematological tumors include tumors of the bone marrow, T or B cell malignancies, leukemias, lymphomas, blastomas, myelomas, and the like. Further examples of cancers that may be treated using the methods provided herein include, but are not limited to, carcinoma, lymphoma, blastoma, sarcoma, leukemia, squamous cell cancer, lung cancer (including small-cell lung cancer, non-small cell lung cancer, adenocarcinoma of the lung, and squamous carcinoma of the lung), cancer of the peritoneum, hepatocellular cancer, gastric or stomach cancer (including gastrointestinal cancer and gastrointestinal stromal cancer), pancreatic cancer, glioblastoma, cervical cancer, ovarian cancer, liver cancer, bladder cancer, breast cancer, colon cancer, colorectal cancer, endometrial or uterine carcinoma, salivary gland carcinoma, kidney or renal cancer, prostate cancer, vulval cancer, thyroid cancer, various types of head and neck cancer, melanoma, superficial spreading melanoma, lentigo malignant melanoma, acral lentiginous melanomas, nodular melanomas, as well as B-cell lymphoma (including low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; and Waldenstrom's macroglobulinemia), chronic lymphocytic leukemia (CLL), acute lymphoblastic leukemia (ALL), Hairy cell leukemia, multiple myeloma, acute myeloid leukemia (AML) and chronic myeloblastic leukemia.

The cancer may specifically be of the following histological type, though it is not limited to these: neoplasm, malignant; carcinoma; carcinoma, undifferentiated; giant and spindle cell carcinoma; small cell carcinoma; papillary carcinoma; squamous cell carcinoma; lymphoepithelial carcinoma; basal cell carcinoma; pilomatrix carcinoma; transitional cell carcinoma; papillary transitional cell carcinoma; adenocarcinoma; gastrinoma, malignant; cholangiocarcinoma; hepatocellular carcinoma; combined hepatocellular carcinoma and cholangiocarcinoma; trabecular adenocarcinoma; adenoid cystic carcinoma; adenocarcinoma in adenomatous polyp; adenocarcinoma, familial polyposis coli; solid carcinoma; carcinoid tumor, malignant; branchiolo-alveolar adenocarcinoma; papillary adenocarcinoma; chromophobe carcinoma; acidophil carcinoma; oxyphilic adenocarcinoma; basophil carcinoma; clear cell adenocarcinoma; granular cell carcinoma; follicular adenocarcinoma; papillary and follicular adenocarcinoma; nonencapsulating sclerosing carcinoma; adrenal cortical carcinoma; endometroid carcinoma; skin appendage carcinoma; apocrine adenocarcinoma; sebaceous adenocarcinoma; ceruminous adenocarcinoma; mucoepidermoid carcinoma; cystadenocarcinoma; papillary cystadenocarcinoma; papillary serous cystadenocarcinoma; mucinous cystadenocarcinoma; mucinous adenocarcinoma; signet ring cell carcinoma; infiltrating duct carcinoma; medullary carcinoma; lobular carcinoma; inflammatory carcinoma; paget's disease, mammary; acinar cell carcinoma; adenosquamous carcinoma; adenocarcinoma w/squamous metaplasia; thymoma, malignant; ovarian stromal tumor, malignant; thecoma, malignant; granulosa cell tumor, malignant; androblastoma, malignant; sertoli cell carcinoma; leydig cell tumor, malignant; lipid cell tumor, malignant; paraganglioma, malignant; extramammary paraganglioma, malignant; pheochromocytoma; glomangiosarcoma; malignant melanoma; amelanotic melanoma; superficial spreading melanoma; malignant melanoma in giant pigmented nevus; epithelioid cell melanoma; blue nevus, malignant; sarcoma; fibrosarcoma; fibrous histiocytoma, malignant; myxosarcoma; liposarcoma; leiomyosarcoma; rhabdomyosarcoma; embryonal rhabdomyosarcoma; alveolar rhabdomyosarcoma; stromal sarcoma; mixed tumor, malignant; mullerian mixed tumor; nephroblastoma; hepatoblastoma; carcinosarcoma; mesenchymoma, malignant; brenner tumor, malignant; phyllodes tumor, malignant; synovial sarcoma; mesothelioma, malignant; dysgerminoma; embryonal carcinoma; teratoma, malignant; struma ovarii, malignant; choriocarcinoma; mesonephroma, malignant; hemangiosarcoma; hemangioendothelioma, malignant; kaposi's sarcoma; hemangiopericytoma, malignant; lymphangiosarcoma; osteosarcoma; juxtacortical osteosarcoma; chondrosarcoma; chondroblastoma, malignant; mesenchymal chondrosarcoma; giant cell tumor of bone; ewing's sarcoma; odontogenic tumor, malignant; ameloblastic odontosarcoma; ameloblastoma, malignant; ameloblastic fibrosarcoma; pinealoma, malignant; chordoma; glioma, malignant; ependymoma; astrocytoma; protoplasmic astrocytoma; fibrillary astrocytoma; astroblastoma; glioblastoma; oligodendroglioma; oligodendroblastoma; primitive neuroectodermal; cerebellar sarcoma; ganglioneuroblastoma; neuroblastoma; retinoblastoma; olfactory neurogenic tumor; meningioma, malignant; neurofibrosarcoma; neurilemmoma, malignant; granular cell tumor, malignant; malignant lymphoma; hodgkin's disease; hodgkin's; paragranuloma; malignant lymphoma, small lymphocytic; malignant lymphoma, large cell, diffuse; malignant lymphoma, follicular; mycosis fungoides; other specified non-hodgkin's lymphomas; malignant histiocytosis; multiple myeloma; mast cell sarcoma; immunoproliferative small intestinal disease; leukemia; lymphoid leukemia; plasma cell leukemia; erythroleukemia; lymphosarcoma cell leukemia; myeloid leukemia; basophilic leukemia; eosinophilic leukemia; monocytic leukemia; mast cell leukemia; megakaryoblastic leukemia; myeloid sarcoma; and hairy cell leukemia.

The polypeptide may be used herein as an antitumor agent in a variety of modalities for triggering complement activation in tumor tissue or for triggering complement activation where it is considered desirable. In a particular embodiment, the invention contemplates methods of using a polypeptide as an antitumor agent, and therefore comprises contacting a population of tumor cells with a therapeutically effective amount of a polypeptide for a time period sufficient to inhibit tumor cell growth.

In one embodiment, the contacting in vivo is accomplished by administering, by intravenous intraperitoneal, or intratumoral injection, a therapeutically effective amount of a physiologically tolerable composition comprising a polypeptide of this invention to a patient. The polypeptide can be administered parenterally by injection or by gradual infusion over time. The polypeptide can be administered intravenously, intraperitoneally, orally, intramuscularly, subcutaneously, intracavity, transdermally, dermally, can be delivered by peristaltic means, or can be injected directly into the tissue containing the tumor cells.

Therapeutic compositions comprising polypeptides are conventionally administered intravenously, such as by injection of a unit dose, for example. The term "unit dose" when used in reference to a therapeutic composition refers to physically discrete units suitable as unitary dosage for the subject, each unit containing a predetermined quantity of active material calculated to produce the desired therapeutic effect in association with the required diluent, i.e., carrier, or vehicle.

The compositions are administered in a manner compatible with the dosage formulation, and in a therapeutically effective amount. The quantity to be administered depends on the subject to be treated, capacity of the subject's system to utilize the active ingredient, and degree of therapeutic effect desired. Precise amounts of active ingredient required to be administered depend on the judgment of the practitioner and are peculiar to each individual. However, suitable dosage ranges for systemic application are disclosed herein and depend on the route of administration. Suitable regimes for initial and booster administration are also contemplated and are typified by an initial administration followed by repeated doses at one or more hour intervals by a subsequent injection or other administration. Exemplary multiple administrations are described herein and are particularly preferred to maintain continuously high serum and tissue levels of polypeptide. Alternatively, continuous intravenous infusion sufficient to maintain concentrations in the blood in the ranges specified for in vivo therapies are contemplated.

It is contemplated that a polypeptide of the invention can be administered systemically or locally to treat disease, such as to inhibit tumor cell growth or to kill cancer cells in cancer patients with locally advanced or metastatic cancers. They can be administered intravenously, intrathecally, and/or intraperitoneally. They can be administered alone or in combination with anti-proliferative drugs. In one embodiment, they are administered to reduce the cancer load in the patient prior to surgery or other procedures. Alternatively, they can be administered after surgery to ensure that any remaining cancer (e.g., cancer that the surgery failed to eliminate) does not survive.

A therapeutically effective amount of a polypeptide is a predetermined amount calculated to achieve the desired effect, i.e., to trigger CDC in the tumor tissue, and thereby mediate a tumor-ablating pro-inflammatory response. Thus, the dosage ranges for the administration of polypeptide of the invention are those large enough to produce the desired effect in which the symptoms of tumor cell division and cell cycling are reduced. The dosage should not be so large as to cause adverse side effects, such as hyperviscosity syndromes, pulmonary edema, congestive heart failure, neurological effects, and the like. Generally, the dosage will vary with age of, condition of, sex of, and extent of the disease in the patient and can be determined by one of skill in the art. The dosage can be adjusted by the individual physician in the event of any complication.

VIII. Combination Therapy

In certain embodiments, the compositions and methods of the present embodiments involve administration of a polypeptide or antibody in combination with a second or additional therapy. Such therapy can be applied in the treatment of any disease that is responsive to CDC. For example, the disease may be cancer.

The methods and compositions, including combination therapies, enhance the therapeutic or protective effect, and/or increase the therapeutic effect of another anti-cancer or anti-hyperproliferative therapy. Therapeutic and prophylactic methods and compositions can be provided in a combined amount effective to achieve the desired effect, such as the killing of a cancer cell and/or the inhibition of cellular hyperproliferation. This process may involve administering a polypeptide or antibody and a second therapy. The second therapy may or may not have a direct cytotoxic effect. For example, the second therapy may be an agent that upregulates the immune system without having a direct cytotoxic effect. A tissue, tumor, or cell can be exposed to one or more compositions or pharmacological formulation(s) comprising one or more of the agents (e.g., a polypeptide or an anti-cancer agent), or by exposing the tissue, tumor, and/or cell with two or more distinct compositions or formulations, wherein one composition provides 1) a polypeptide or antibody, 2) an anti-cancer agent, or 3) both a polypeptide or antibody and an anti-cancer agent. Also, it is contemplated that such a combination therapy can be used in conjunction with chemotherapy, radiotherapy, surgical therapy, or immunotherapy.

The terms "contacted" and "exposed," when applied to a cell, are used herein to describe the process by which a therapeutic polypeptide or antibody and a chemotherapeutic or radiotherapeutic agent are delivered to a target cell or are placed in direct juxtaposition with the target cell. To achieve cell killing, for example, both agents are delivered to a cell in a combined amount effective to kill the cell or prevent it from dividing.

A polypeptide or antibody may be administered before, during, after, or in various combinations relative to an anti-cancer treatment. The administrations may be in intervals ranging from concurrently to minutes to days to weeks. In embodiments where the polypeptide or antibody is provided to a patient separately from an anti-cancer agent, one would generally ensure that a significant period of time did not expire between the time of each delivery, such that the two compounds would still be able to exert an advantageously combined effect on the patient. In such instances, it is contemplated that one may provide a patient with the polypeptide and the anti-cancer therapy within about 12 to 24 or 72 h of each other and, more particularly, within about 6-12 h of each other. In some situations it may be desirable to extend the time period for treatment significantly where several days (2, 3, 4, 5, 6, or 7) to several weeks (1, 2, 3, 4, 5, 6, 7, or 8) lapse between respective administrations.

In certain embodiments, a course of treatment will last 1-90 days or more (this such range includes intervening days). It is contemplated that one agent may be given on any day of day 1 to day 90 (this such range includes intervening days) or any combination thereof, and another agent is given on any day of day 1 to day 90 (this such range includes intervening days) or any combination thereof. Within a single day (24-hour period), the patient may be given one or multiple administrations of the agent(s). Moreover, after a course of treatment, it is contemplated that there is a period of time at which no anti-cancer treatment is administered. This time period may last 1-7 days, and/or 1-5 weeks, and/or 1-12 months or more (this such range includes intervening days), depending on the condition of the patient, such as their prognosis, strength, health, etc. It is expected that the treatment cycles would be repeated as necessary.

Various combinations may be employed. For the example below a polypeptide or antibody is "A" and an anti-cancer therapy is "B":

| | | | | | |
|---|---|---|---|---|---|
| A/B/A | B/A/B | B/B/A | A/A/B | A/B/B | B/A/A |
| A/B/B/B | B/A/B/B | B/B/B/A | B/B/A/B | A/A/B/B | A/B/A/B |
| A/B/B/A | B/B/A/A | B/A/B/A | B/A/A/B | A/A/A/B | B/A/A/A |
| A/B/A/A | A/A/B/A | | | | |

Administration of any polypeptide or therapy of the present embodiments to a patient will follow general protocols for the administration of such compounds, taking into account the toxicity, if any, of the agents. Therefore, in some embodiments there is a step of monitoring toxicity that is attributable to combination therapy. In some embodiments involving treating a cancer in a subject, the second therapy may be, e.g., a chemotherapy, a radiotherapy, an immunotherapy, a gene therapy, or a surgery.

A. Chemotherapy

A wide variety of chemotherapeutic agents may be used in accordance with the present embodiments. The term "chemotherapy" refers to the use of drugs to treat cancer. A "chemotherapeutic agent" is used to connote a compound or composition that is administered in the treatment of cancer. These agents or drugs are categorized by their mode of activity within a cell, for example, whether and at what stage they affect the cell cycle. Alternatively, an agent may be characterized based on its ability to directly cross-link DNA, to intercalate into DNA, or to induce chromosomal and mitotic aberrations by affecting nucleic acid synthesis.

Examples of chemotherapeutic agents include alkylating agents, such as thiotepa and cyclosphosphamide; alkyl sulfonates, such as busulfan, improsulfan, and piposulfan; aziridines, such as benzodopa, carboquone, meturedopa, and uredopa; ethylenimines and methylamelamines, including altretamine, triethylenemelamine, trietylenephosphoramide, triethiylenethiophosphoramide, and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards, such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, and uracil mustard; nitrosureas, such as carmustine, chlorozotocin, fotemustine, lomustine, nimustine, and ranimnustine; antibiotics, such as the enediyne antibiotics (e.g., calicheamicin, especially calicheamicin gammaII and calicheamicin omegaI1); dynemicin, including dynemicin A; bisphosphonates, such as clodronate; an esperamicin; as well as neocarzinostatin chromophore and related chromoprotein enediyne antiobiotic chromophores, aclacinomysins, actinomycin, authrarnycin, azaserine, bleomycins, cactinomycin, carabicin, carminomycin, carzinophilin, chromomycinis, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins, such as mitomycin C, mycophenolic acid, nogalarnycin, olivomycins, peplomycin, potfiromycin, puromycin, quelamycin, rodorubicin, streptonigrin, streptozocin, tubercidin, ubenimex, zinostatin, and zorubicin; anti-metabolites, such as methotrexate and 5-fluorouracil (5-FU); folic acid analogues, such as denopterin, pteropterin, and trimetrexate; purine analogs, such as fludarabine, 6-mercaptopurine, thiamiprine, and thioguanine; pyrimidine analogs, such as ancitabine, azacitidine, 6-azauridine, carmofur, cytarabine, dideoxyuridine, doxifluridine, enocitabine, and floxuridine; androgens, such as calusterone, dromostanolone propionate, epitiostanol, mepitiostane, and testolactone; anti-adrenals, such as mitotane and trilostane; folic acid replenisher, such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids, such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSKpolysaccharide complex; razoxane; rhizoxin; sizofiran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; taxoids, e.g., paclitaxel and docetaxel gemcitabine; 6-thioguanine; mercaptopurine; platinum coordination complexes, such as cisplatin, oxaliplatin, and carboplatin; vinblastine; platinum; etoposide (VP-16); ifosfamide; mitoxantrone; vincristine; vinorelbine; novantrone; teniposide: edatrexate; daunomycin; aminopterin; xeloda; ibandronate; irinotecan (e.g., CPT-11); topoisomerase inhibitor RFS 2000; difluorometlhylornithine (DMFO); retinoids, such as retinoic acid; capecitabine; carboplatin, procarbazine, plicomycin, gemcitabien, navelbine, farnesyl-protein tansferase inhibitors, transplatinum, and pharmaceutically acceptable salts, acids, or derivatives of any of the above.

B. Radiotherapy

Other factors that cause DNA damage and have been used extensively include what are commonly known as γ-rays, X-rays, and/or the directed delivery of radioisotopes to tumor cells. Other forms of DNA damaging factors are also contemplated, such as microwaves, proton beam irradiation (U.S. Pat. Nos. 5,760,395 and 4,870,287), and UV-irradiation. It is most likely that all of these factors affect a broad range of damage on DNA, on the precursors of DNA, on the replication and repair of DNA, and on the assembly and maintenance of chromosomes. Dosage ranges for X-rays range from daily doses of 50 to 200 roentgens for prolonged periods of time (3 to 4 wk), to single doses of 2000 to 6000 roentgens. Dosage ranges for radioisotopes vary widely, and depend on the half-life of the isotope, the strength and type of radiation emitted, and the uptake by the neoplastic cells.

C. Immunotherapy

The skilled artisan will understand that immunotherapies may be used in combination or in conjunction with methods of the embodiments. In the context of cancer treatment, immunotherapeutics, generally, rely on the use of immune effector cells and molecules to target and suppress immune cells. Blinatumomab (Blincyto®) is such an example. Checkpoint inhibitors, such as, for example, ipilumimab, are another such example. The immune effector may be, for example, an antibody specific for some marker on the surface of a tumor cell. The antibody alone may serve as an effector of therapy or it may recruit other cells to actually affect cell killing. The antibody also may be conjugated to a drug or toxin (chemotherapeutic, radionuclide, ricin A chain, cholera toxin, pertussis toxin, etc.) and serve merely as a targeting agent. Alternatively, the effector may be a lymphocyte carrying a surface molecule that interacts, either directly or indirectly, with a tumor cell target. Various effector cells include cytotoxic T cells and NK cells.

In one aspect of immunotherapy, the tumor cell must bear some marker that is amenable to targeting, i.e., is not present on the majority of other cells. Many tumor markers exist and any of these may be suitable for targeting in the context of the present embodiments. Common tumor markers include CD20, carcinoembryonic antigen, tyrosinase (p97), gp68, TAG-72, HMFG, Sialyl Lewis Antigen, MucA, MucB, PLAP, laminin receptor, erb B, and p155. An alternative aspect of immunotherapy is to combine anticancer effects with immune stimulatory effects. Immune stimulating molecules also exist including: cytokines, such as IL-2, IL-4, IL-12, GM-CSF, gamma-IFN, chemokines, such as MIP-1, MCP-1, IL-8, and growth factors, such as FLT3 ligand.

Examples of immunotherapies currently under investigation or in use are immune adjuvants, e.g., *Mycobacterium bovis, Plasmodium falciparum*, dinitrochlorobenzene, and aromatic compounds (U.S. Pat. Nos. 5,801,005 and 5,739, 169; Hui and Hashimoto, 1998; Christodoulides et al., 1998); cytokine therapy, e.g., interferons α, β, and γ, IL-1, GM-CSF, and TNF (Bukowski et al., 1998; Davidson et al., 1998; Hellstrand et al., 1998); gene therapy, e.g., TNF, IL-1, IL-2, and p53 (Qin et al., 1998; Austin-Ward and Villaseca, 1998; U.S. Pat. Nos. 5,830,880 and 5,846,945); and monoclonal antibodies, e.g., anti-CD20, anti-ganglioside GM2, and anti-p185 (Hollander, 2012; Hanibuchi et al., 1998; U.S. Pat. No. 5,824,311). It is contemplated that one or more anti-cancer therapies may be employed with the antibody therapies described herein.

D. Surgery

Approximately 60% of persons with cancer will undergo surgery of some type, which includes preventative, diagnostic or staging, curative, and palliative surgery. Curative surgery includes resection in which all or part of cancerous tissue is physically removed, excised, and/or destroyed and may be used in conjunction with other therapies, such as the treatment of the present embodiments, chemotherapy, radiotherapy, hormonal therapy, gene therapy, immunotherapy, and/or alternative therapies. Tumor resection refers to physical removal of at least part of a tumor. In addition to tumor resection, treatment by surgery includes laser surgery, cryosurgery, electrosurgery, and microscopically-controlled surgery (Mohs' surgery).

Upon excision of part or all of cancerous cells, tissue, or tumor, a cavity may be formed in the body. Treatment may be accomplished by perfusion, direct injection, or local application of the area with an additional anti-cancer therapy. Such treatment may be repeated, for example, every 1, 2, 3, 4, 5, 6, or 7 days, or every 1, 2, 3, 4, and 5 weeks or every 1, 2, 3, 4, 5, 6, 7, 8, 9, 10, 11, or 12 months. These treatments may be of varying dosages as well.

E. Other Agents

It is contemplated that other agents may be used in combination with certain aspects of the present embodiments to improve the therapeutic efficacy of treatment. These additional agents include agents that affect the upregulation of cell surface receptors and GAP junctions, cytostatic and differentiation agents, inhibitors of cell adhesion, agents that increase the sensitivity of the hyperproliferative cells to apoptotic inducers, or other biological agents. Increases in intercellular signaling by elevating the number of GAP junctions would increase the anti-hyperproliferative effects on the neighboring hyperproliferative cell population. In other embodiments, cytostatic or differentiation agents can be used in combination with certain aspects of the present embodiments to improve the anti-hyperproliferative efficacy of the treatments. Inhibitors of cell adhesion are contemplated to improve the efficacy of the present embodiments. Examples of cell adhesion inhibitors are focal adhesion kinase (FAKs) inhibitors and Lovastatin. It is further contemplated that other agents that increase the sensitivity of a hyperproliferative cell to apoptosis, such as the antibody c225, could be used in combination with certain aspects of the present embodiments to improve the treatment efficacy.

IX. Kits

Certain aspects of the present invention may provide kits, such as therapeutic kits. For example, a kit may comprise one or more pharmaceutical composition as described herein and optionally instructions for their use. Kits may also comprise one or more devices for accomplishing administration of such compositions. For example, a subject kit may comprise a pharmaceutical composition and catheter for accomplishing direct intravenous injection of the composition into a cancerous tumor. In other embodiments, a subject kit may comprise pre-filled ampoules of a polypeptide, optionally formulated as a pharmaceutical, or lyophilized, for use with a delivery device.

Kits may comprise a container with a label. Suitable containers include, for example, bottles, vials, and test tubes. The containers may be formed from a variety of materials, such as glass or plastic. The container may hold a composition that includes a polypeptide that is effective for therapeutic or non-therapeutic applications, such as described above. The label on the container may indicate that the composition is used for a specific therapy or non-therapeutic application, and may also indicate directions for either in vivo or in vitro use, such as those described above. The kit of the invention will typically comprise the container described above and one or more other containers comprising materials desirable from a commercial and user standpoint, including buffers, diluents, filters, needles, syringes, and package inserts with instructions for use.

X. Examples

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1—Library Construction Strategy for the Isolation of IgG1 Fc Domains that Bind to FcγRIIB E. coli does not encode a protein glysocylation machinery and therefore the Fc domain of IgG expressed in the periplasm of E. coli is aglycosylated, lacking the glycan that is normally appended to N297 of the Fc domain. Aglcysoylated Fc domains display a greater degree of conformational flexibility which results in highly attenuated or no detectable binding to effector FcγRs (FcγRIA, FcγRIIA, FcγRIIB, FcγRIIc, FcγRIIIA, FcγRIIIB) and C1q (Jefferis et al., 2005; Borrok et al., 2012). To isolate aglycosylated Fc domain variants containing mutations that enable binding to FcγRIIB despite the absence of the N297 glycan, three different libraries were constructed. In the first library called S-library, random amino acid substitutions were introduced at Glu231, Leu232, Leu233, Gly234, and Gly235 using spiked oligonucleotides with codons designed to conserve the wild-type amino acid with a probability of around 50% (Lanio et al., 1998). Four primers (SEQ ID NOs:10-13) were designed and used for mutagenesis as described in example 2 below. (Table 7). The second library called SE-library was constructed by error prone with 1% error rate (Fromant et al., 1995) of the S-library above. To introduce random mutations on Fc domain, the error-prone PCR protocol by Fromant was used, but the Fc library genes were used as template. This is a difference from the previously used method. In order to introduce additional random mutation on Fc domain of S-library, the two primers PCH018 (SEQ ID NO: 12) and PCH021 (SEQ ID NO: 13) were used. A third library called E-library, was constructed by error prone PCR with 1% error rate of the wild type Fc template using primers PCH018 (SEQ ID NO: 12) and PCH021 (SEQ ID NO: 13).

Example 2—the Construction of Libraries for Engineering Fc Domain

Figure 1B:
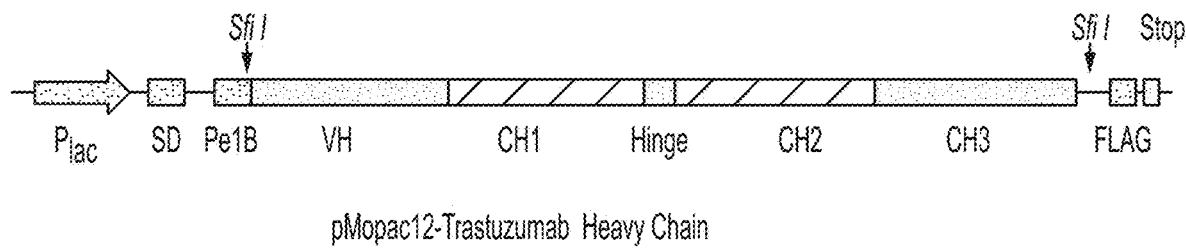
Figure 2:
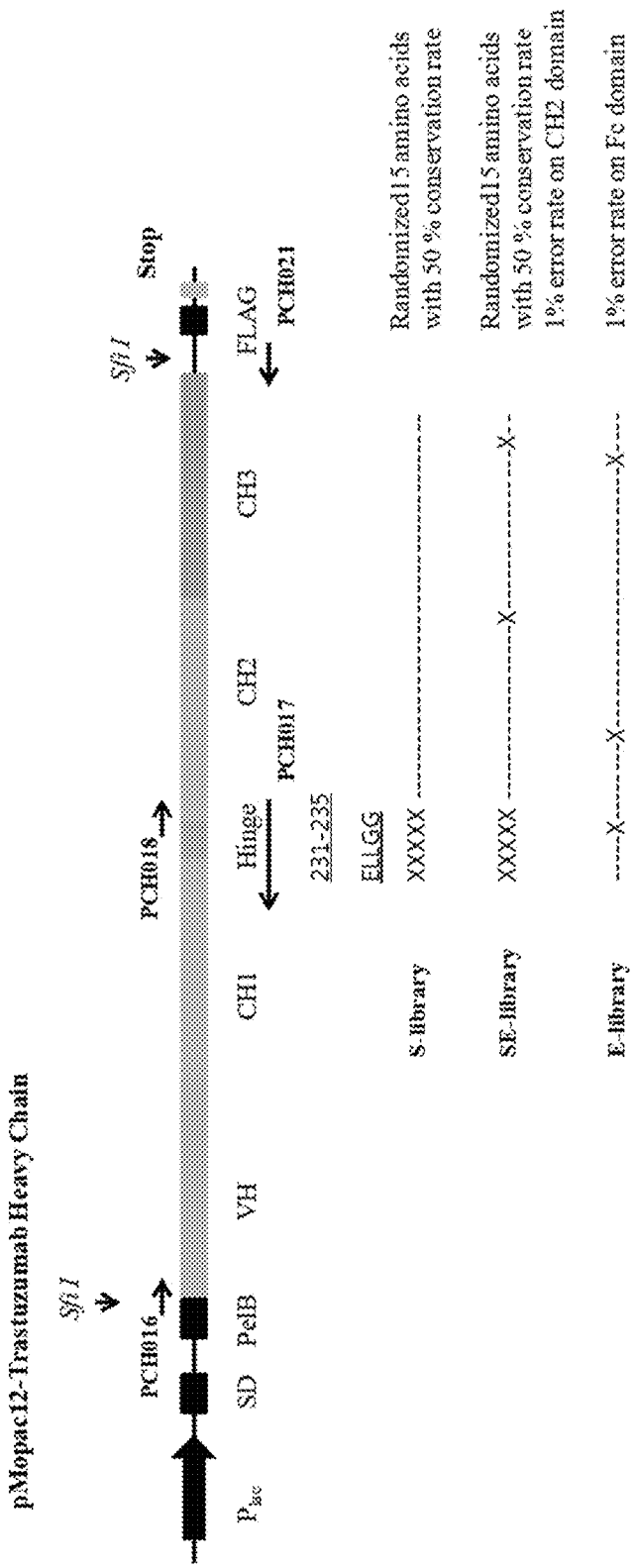
FIG. 2: Brief scheme of the strategies of constructing libraries of mutated Fc polypeptides for FcγRIIB. A fragment of the wild-type IgG1 Fc domain is shown (SEQ ID NO: 29)

All plasmids and primers are described in Tables 10 and 11. All primers were synthesized by Integrated DNA Technologies. IgG polypeptides were expressed and displayed on the inner membrane of E. coli using the vectors: pBAD30-PelB-VL-Ck-NlpA-VL-Ck-His-cMyc and pMopac12-pelB-IgG-VH-CH1-CH2-CH3-FLAG (Jung et al., 2012) (FIG. 1). In order to construct the S-library, the four primers (SEQ ID NOs: 10-13) were used (Table 7 and FIG. 2). One of the specific primers (PCH017; SEQ ID NOs: 11) among the four primers contain degenerate codons using the spiked oligonucleotides to conserve wild-type amino acids sequences with approximately 50% probability. Two fragments of the heavy chain gene of IgG1 were amplified with the four primers and stitched together by overlap extension with PCH016 (SEQ ID NO: 10) and PCH021 (SEQ ID NO: 13) (S-library, Table 7 and FIG. 2). For another sub-library, standard error-prone PCR was employed on Fc domain with Fc library genes from the S-library as a template and using oligonucleotides PCH018 (SEQ ID NO: 12) and PCH021 (SEQ ID NO: 13) (SE-library). Error-prone PCR mutagenesis with 1% targeted error rate was performed using 12 nmole of dATP, 10 nmole of dCTP, 36 nmole of dGTP, 250 nmole of dTTP, 40 pmole of each primers, 0.5 pg of BSA, 327.5 nmole of $MgCl_2$, 50 nmole of $MnCl_2$, 200 ng of template DNA, 5 units of Taq DNA polymerase, and 1×PCR reaction buffer. The Fc library genes were amplified with the following thermocycling program: One cycle of 94° C. for 5 min; 30 cycles of 91° C. for 1 min, 55° C. for 1 min, and 72° C. for 3 min; One cycle of 72° C. for 5 min. As a result, the SE-library contained genes with 5 random amino acids (from the S-library construction) and an additional 1% random mutations in the Fc domain. For the E-library, standard error-prone PCR was employed using the Fc domain of IgG1 gene as the template with PCH018 (SEQ ID NO:12) and PCH021 (SEQ ID NO: 13). The conditions for the error-prone PCR with 1% error rate were the same as described above. The three amplified heavy chain library genes were ligated in-frame into SfiI digested pMopac12-pelB-IgG-VH-CH1-CH2-CH3-FLAG vector. The resulting plasmids were transformed into E. coli JUDE-1 cells containing the plasmid pBAD30-PelB-VL-Ck-NlpA-VL-Ck-His-cMyc. (Jung et al., 2010; Jung et al., 2012). The sizes of sub-libraries were $4\times10^8$ (S-library), $6\times10^8$ (SE-library), and $4\times10^8$ (E-library), respectively.

Example 3—Preparation of Human and Mouse FcγR

Plasmids for mammalian expression of FcγRs were constructed as described previously (Jung et al., 2012 and Kelton et al., 2015). FcγRI-His, FcγRIIa-$_{H131}$-GST, FcγRIIa-$_{R131}$-GST, FcγRIIb-GST, FcγRIIIa-$_{V158}$-GST, and FcγRIIIa-$_{F158}$-GST were produced by transient transfection of HEK293F cells (Invitrogen) using the pMAZ-IgH (U.S. Pat. No. 8,043,621) derived expression vectors described in Table 8. FcγRIIa-$_{H131}$-His, FcγRIIa-$_{R131}$-His, FcγRIIb-His, FcγRIIIa-$_{V158}$-His, and FcγRIIIa-$_{F158}$-His were produced by transient transfection of HEK293F cells (Invitrogen) using the pcDNA3.4 derived expression vectors described in Table 8. The transfected HEK293F cells were cultured for 5 days in a 5% $CO_2$ incubator at 37° C. The supernatant was collected by centrifugation at 4,000×g for 10 min and filtered using a 0.22 m polyethersulfone (PES) membrane filter (PALL). The FcγRs-His proteins were purified with Ni-NTA (GE Healthcare) affinity columns according to the manufacturer's instructions. The FcγRs-GSTs were purified with Glutathione Sepharose (GE Healthcare) affinity columns according to the manufacturer's instructions. To remove lipopolysaccharide (LPS) and non-specifically bound protein, the FcγRs-bound resins were washed with 50 mL of PBS containing 0.1% Triton®X-114 (Sigma-Aldrich) and 50 mL of PBS. The FcγRI-His was eluted with PBS containing 250 mM imidazole, the FcγRs-GST were eluted with PBS containing 10 mM reduced L-glutathione. The buffer of all eluted FcγRs was exchanged to PBS using an Amicon Ultra-4 (Millipore) unit.

Plasmids for mammalian expression of mFcγRs were constructed. The genes for mFcγRI-His (UniProtKB—P08101), FcγRII-His (UniProtKB—P26151), FcγRIII-His (UniProtKB—P08508), and FcγRIV-His (UniProtKB—Q8R2R4) were synthesized by IDT. The mFcγR genes were cloned into pcDNA3.4 and the mFcγR-his tag proteins were produced by transient transfection of HEK293F cells (Invitrogen). The transfected HEK293F cells were cultured for 5 days in a 5% $CO_2$ incubator at 37° C. The supernatant was collected by centrifugation at 4,000×g for 10 min and filtered using a 0.22 m polyethersulfone (PES) membrane filter (PALL). Each mFcγRs-His was purified with Ni-NTA (GE Healthcare) affinity columns according to the manufacturer's instructions. To remove lipopolysaccharide (LPS)

and non-specifically bound protein, the FcγRs-bound resins were washed with 50 mL of PBS containing 0.1% Triton®X-114 (Sigma-Aldrich) and 50 mL of PBS. Each mFcγRs-His was eluted with PBS containing 250 mM imidazole. The buffer of all eluted mFcγRs was exchanged to PBS using an Amicon Ultra-4 (Millipore) unit.

The biotinylated mFcγRII (b-mFcγRII) was prepared under manufacturer's instructions. Briefly, one mg of mFcγRII was incubated with 20-fold excess amount of NHS-sulfo-biotin (Pierce) at 4° C. for 4 hours and then run through a desalting column. The concentration of biotinylated mFcγRII was measured by absorbance at 280 nm.

Example 4—Screening of Fc Libraries for FcγRIIB

E. coli JUDE-1 cells were cultured overnight at 37° C. and 250 rpm in Terrific Broth (TB) with chloramphenicol (40 µg/mL) and kanamycin (50 µg/mL). Following overnight growth, cells were diluted 1:50 in fresh 100 mL TB media with two antibiotics. E. coli JUDE-1 cells were cultured at 37° C. and 250 rpm until the $OD_{600}$ reached a value of approximately 0.4. Then, 1 mM isopropyl-β-D-thiogalactopyranoside (IPTG, Sigma Aldrich) and 2% L-arabinose (Sigma-Aldrich) were added to the E. coli JUDE-1 cells to facilitate the protein expression, and the cells were then further incubated at 25° C. for 20 h. Cultures (8 mL culture volume) were harvested by centrifugation and washed two times in 1 mL of ice-chilled 10 mM Tris-HCl (pH8.0). The washed cells were resuspended in 1 mL of ice-chilled STE solution (0.5 M sucrose, 10 mM Tris-HCl, 10 mM EDTA, pH 8.0) and incubated at 37° C. for 30 min. The cells were centrifuged at 13,000 rpm for 1 min and washed with 1 mL of Solution A (0.5 M sucrose, 20 mM $MgCl_2$, 10 mM MOPS, pH6.8). The washed cells were incubated in 1 mL of Solution A with 1 mg/mL hen egg lysozyme (Sigma-Aldrich) at 37° C. for 15 min. After centrifugation at 13,000 rpm for 1 min, the pelleted spheroplasts were resuspended in 1 mL of cold PBS (Jung et al., 2010; Jung et al., 2012).

In order to determine the optimal concentration of target protein for screening, spheroplasts were incubated with 400 nM FcγRIIB-GST and labeled with Goat anti-GST antibody with conjugated to TRITC (Abcam). TRITC (tetramethylrhodamine) is a dye. Ex: 547 nm, Em: 572 nm. As a control, E. coli spheroplasts expressing the PA domain 4 protein of B. anthracis (Leysath et al., 2009) were incubated with the high affinity, glycosylated anti-PA antibody M18. Spheroplasts that bound the control glycosylated, M18 IgG showed binding signals but aglycosylated IgG and three Fc libraries showed little or no binding signals (FIG. 3; Table 4).

TABLE 4

Figure 3:
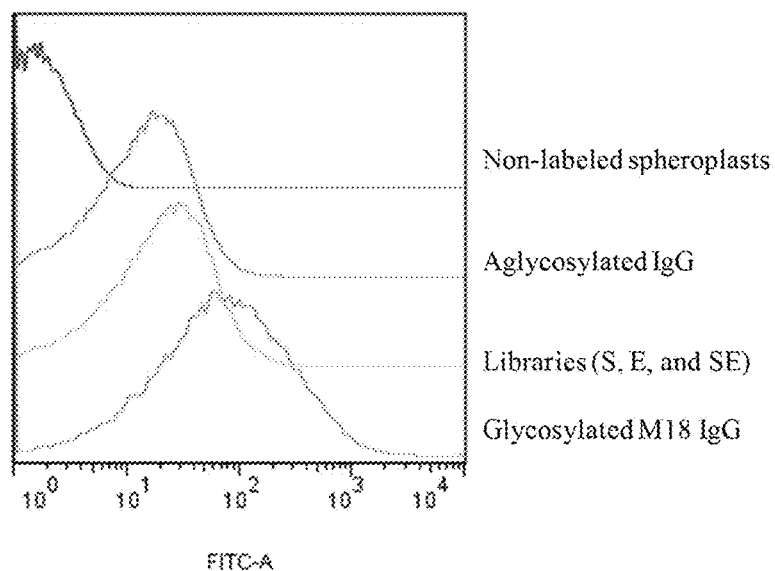
FIG. 3: FACS analysis for confirmation of labeling condition with FcγRIIB. It showed FACS scanning results of each represented spheroplasts when FcγRIIB-GST and anti-GST goat Antibody with TRITC were labeled in PBS.

FACS analysis for confirming of labeling condition with 400 nM FcγRIIB-GST (data correspond to FIG. 3)

| | MFI (Mean Fluorescence intensity) |
|---|---|
| Non-labeled spheroplasts | 1.36 |
| Aglycosylated IgG | 11.1 |
| Libraries | 14.5 |
| Glycosylated M18 IgG | 56.6 |

Figure 4:
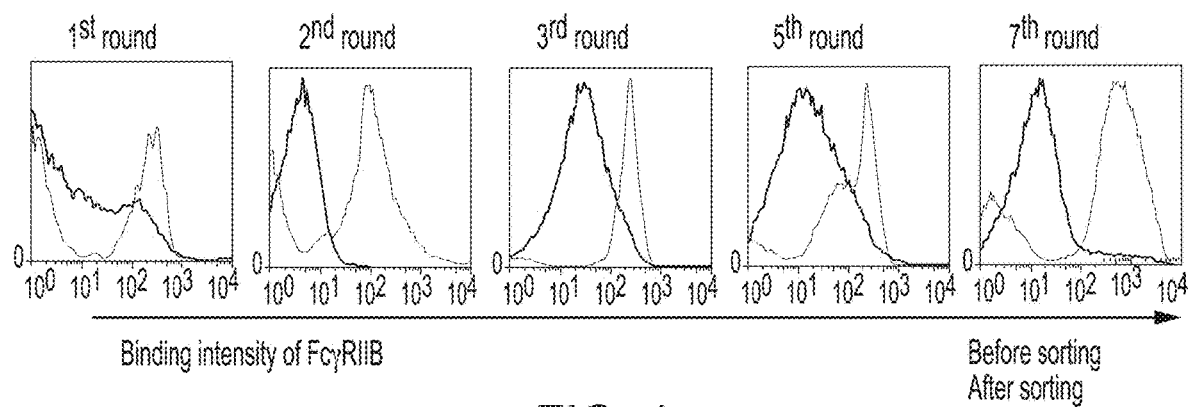
FIG. 4: FACS analysis histograms showing enrichment of E. coli cells expressing antibodies with mutated Fc domains that confer high affinity binding to FcγRIIB. Fluorescent intensity of cells that bind with fluorescently labeled FcγRIIB after each of seven rounds of library sorting and resorting are shown. The right most peak represents the "after sorting" condition in each histogram.

To isolate FcγRIIB-specific aglycosylated IgG1 variants, cells expressing the three sub-libraries described in Example 1 and 2 were labeled with 400 nM FcγRIIB-GST in the presence of 1 µM activating FcγRs as a competitor and screened by on FACSAria™ (BD Biosciences). In each round, the top 1% of the population showing the highest fluorescence was recovered and these sorted spheroplasts were resorted immediately to remove false positives. The heavy chain genes in the sorted spheroplasts were rescued by PCR using two primers (PCH16 and PCH21) after boiling for 5 min and ligated into SfiI-cut pMopac12 vector. The ligated plasmids were transformed in E. coli JUDE-1 cells. Transformants were selected on chloramphenicol- and kanamycin-containing media and the spheroplasts were prepared for the next round of screening using 400 nM FcγRIIB-GST (FIG. 4).

Example 5—FACS Analysis of IgG Variants 30 randomly selected IgG variants from the last round of sorting from libraries screened with FcγRIIB-GST were sequenced. The respective genes were transformed in E. coli JUDE-1, the cells were spheroplasted and analyzed with 400 nM FcγRIIB-GST and goat anti-GST antibodies with TRITC by FACS. As shown in Table 5, all 30 IgG variants showed 6.8-49.8 fold-higher mean fluorescence intensity (MFI) values relative to wild-type aglycosylated IgG for FcγRIIB-GST. For FcγRIIA-GST, 7 IgG variants, B7, B13, B36, B39, B41, B57, and B81, showed lower MFI values than aglycosylated IgG1. 19 IgG variants, B5, B15, B19, B21, B25, B29, B33, B34, B46, B49, B51, B56, B67, B80, B87, B88, B89, B90, and B91, showed similar MFI values with aglycosylated IgG1. Finally, 4 IgG variants, B26, B28, B70, and B78, showed higher MFI values than aglycosylated IgG1. IgG variants, B13, B15, B19, B21, B25, B29, B41, and B90, which have higher binding activities for FcγRIIB-GST and lower or comparable binding activities for FcγRIIA-GST relative to aglycosylated IgG1 were studied further.

TABLE 5

Binding analysis of the isolated twenty two IgG variants with 400 nM FcγRIIB-GST or FcγRIIA (H131 and R131)-GST using FACS.

| Clone # | FcγRIIA-GST (MFI) | Increasing Fold | FcγRIIB-GST (MFI) | Increasing Fold |
|---|---|---|---|---|
| Aglycosylated IgG1 | 40.9 | 1.0 | 14 | 1.0 |
| B5 | 47 | 1.1 | 120.8 | 8.6 |
| B7 | 36 | 0.9 | 171 | 12.2 |
| B13 | 30 | 0.7 | 338.2 | 24.2 |
| B15 | 42 | 1.0 | 499.3 | 35.7 |
| B19 | 49 | 1.2 | 336.5 | 24.0 |
| B21 | 48 | 1.2 | 366.6 | 26.2 |
| B25 | 62 | 1.5 | 407.6 | 29.1 |
| B26 | 183 | 4.5 | 697.6 | 49.8 |
| B28 | 94 | 2.3 | 95.4 | 6.8 |
| B29 | 59 | 1.4 | 408.1 | 29.2 |
| B33 | 52 | 1.3 | 190 | 13.6 |
| B34 | 43 | 1.1 | 161.8 | 11.6 |
| B36 | 32 | 0.8 | 142.1 | 10.2 |
| B39 | 29 | 0.7 | 195.7 | 14.0 |
| B41 | 30 | 0.7 | 256.9 | 18.4 |
| B46 | 50 | 1.2 | 110.5 | 7.9 |
| B49 | 43 | 1.1 | 539.7 | 38.6 |
| B51 | 41 | 1.0 | 124.1 | 8.9 |
| B56 | 59 | 1.4 | 184.6 | 13.2 |
| B57 | 32 | 0.8 | 366.2 | 26.2 |
| B67 | 48 | 1.2 | 121.1 | 8.7 |
| B70 | 99 | 2.4 | 374.6 | 26.8 |
| B78 | 105 | 2.6 | 333.4 | 23.8 |
| B80 | 49 | 1.2 | 412.8 | 29.5 |

TABLE 5-continued

Binding analysis of the isolated twenty two IgG variants with 400 nM FcγRIIB-GST or FcγRIIA (H131 and R131)-GST using FACS.

| Clone # | FcγRIIA-GST (MFI) | Increasing Fold | FcγRIIB-GST (MFI) | Increasing Fold |
| --- | --- | --- | --- | --- |
| B81 | 21 | 0.5 | 149 | 10.6 |
| B87 | 55 | 1.3 | 173.7 | 12.4 |
| B88 | 55 | 1.3 | 223.6 | 16.0 |
| B89 | 54 | 1.3 | 362.2 | 25.9 |
| B90 | 56 | 1.4 | 518.1 | 37.0 |
| B91 | 61 | 1.5 | 555 | 39.6 |

Example 6—Expression and Purification of the Selected Mutant IgG Variants

Figure 5A:
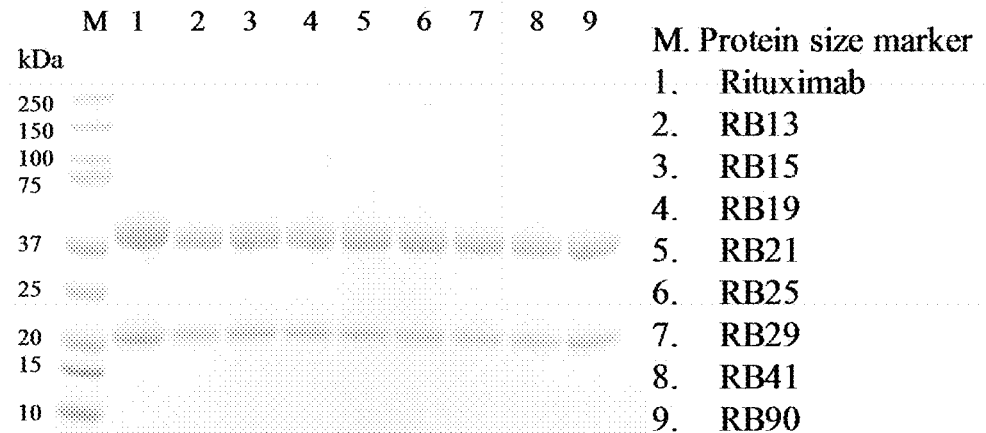
FIGS. 5A-B: SDS-PAGE analysis under reducing (FIG. 5A) or non-reducing (FIG. 5B) conditions, after purifying the glycosylated Rituximab, and the selected eight aglycosylated IgG variants, RB13, RB15, RB19, RB21, RB25, RB29, RB41, and RB90 having anti-CD20 Rituximab Fab domains. M: Protein size marker; 1: Rituximab; 2: RB13; 3: RB15; 4: RB19; 5: RB21; 6: RB25; 7: RB29; 8: RB41; 9: RB90.
Figure 5B:
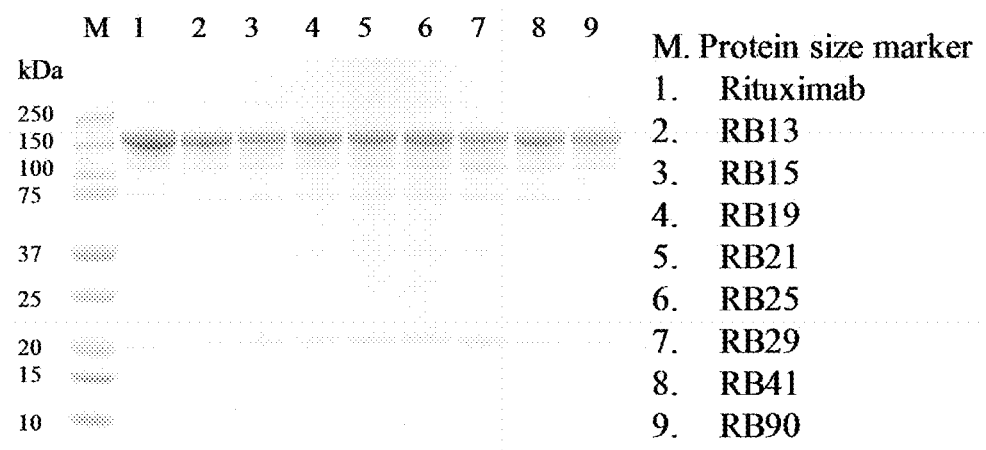
Figure 6:
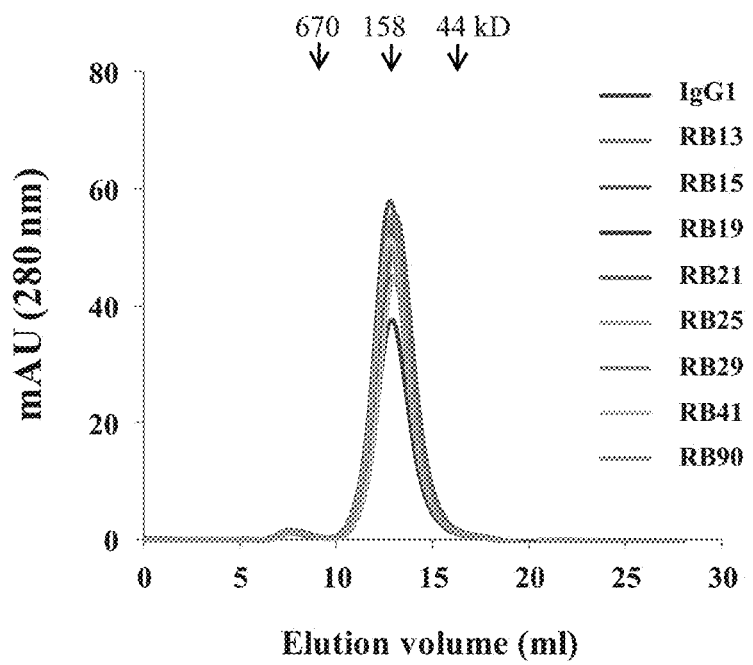
FIG. 6. Size exclusion chromatography (SEC) analysis to confirm that the purified IgG variants were present in monomeric form in solution.

All plasmids and primers are described in Tables 10 and 11. The eight mutant Fc genes, B13, B15, B19, B21, B25, B29, B41, and B90, were amplified from pMopac12-pelB-IgG-VH-CH1-CH2-CH3-FLAG using two specific primers (TH083 (SEQ ID NO: 14) and TH084 (SEQ ID NO: 15)). pcDNA3.4-IgH plasmids were amplified using two specific primers (TH081 (SEQ ID NO: 16) and TH082 (SEQ ID NO: 17)). The eight Fc genes were cloned into pcDNA3.4 using a Gibson Assembly®cloning kit (NEB) according to the manufacturer's instructions (Jung et al., 2012). The Gibson assembled mixtures were transformed into E. coli JUDE-1 cells and their sequences confirmed. Newly constructed Rituximab-Fc variants still have an N-glycosylation site on their CH2 domains and thus become glycosylated when expressed in mammalian cells. In order to express aglycosylated antibodies having the isolated Fc domains from Example 5 above, a T299L mutation, which does not affect the binding ability of the Fc domain with FcγRs but abolishes glycosylation, was introduced using two specific primers (WK68 (SEQ ID NO: 18) and WK69 (SEQ ID NO: 19)) as described previously (Jung et al., 2012). Rituximab-aglycosylated Fc variants received the names RB13, RB15, RB19, RB21, RB25, RB29, RB41, and RB90. The heavy chain genes of eight Rituximab-Fc variants were transiently transfected with an equal mass of light chain plasmid in HEK293F cells (Invitrogen). After incubation in a 5% $CO_2$ incubator at 37° C. for six days, the supernatants were collected by centrifugation at 4,000×g for 10 min and filtered using a 0.22 m PES membrane filter (PALL). The filtered supernatants were passed over Protein A high capacity agarose resin (Thermo Scientific) three times. To remove LPS and non-specifically bound protein, the IgG-bound resins were washed with 50 mL PBS containing 0.1% Triton®X-114 (Sigma-Aldrich) and 50 mL PBS. All IgG variants were eluted with 100 mM glycine buffer (pH 3.0) and immediately neutralized with 1M Tris-HCl buffer (pH 8.0). The buffer of all eluted Rituximab-Fc antibody variants was exchanged to PBS by Amicon® Ultra-4 (Millipore). The purity of reduced or non-reduced proteins for the Rituximab-Fc antibody variants and for authentic (w.t.) Rituximab expressed in HEK293 cells as above were assessed by 4%-20% gradient SDS-PAGE gel (NuSep) under reducing (FIG. 5A) and non-reducing (FIG. 5B) conditions. Similar to Rituximab, the eight IgG variants were properly assembled with over 95% purity. In order to determine whether the eight IgG variants exist as monomers or multimers in solution, purified proteins and HEK 293 cell-expressed Rituximab as a control were analyzed by size exclusion chromatography (Superdex™200 10/300GC, GE Healthcare). Thyroglobulin (670 kDa), bovine gamma globulin (158 kDa), and chicken ovalbumin (44 kDa) were used as protein size markers. The eight IgG variants elution profiles were similar with that of Rituximab and no peak of corresponding to aggregated protein was detected. The elution times of all IgG variants were very close to the 158 kDa protein size marker, consistent with the expected elution time for monomeric IgG (FIG. 6). These results suggest that eight engineered IgG variants do not form multimeric IgGs and that they exist as assembled monomers in solution.

Example 7—Binding Properties of the Selected IgG Variants to Human FcγRs

The binding affinities of the eight IgG variants to human FcγRs (hFcγRs) were evaluated with enzyme-linked immunosorbent assay (ELISA) and surface plasmon resonance (SPR).

Figure 7A:
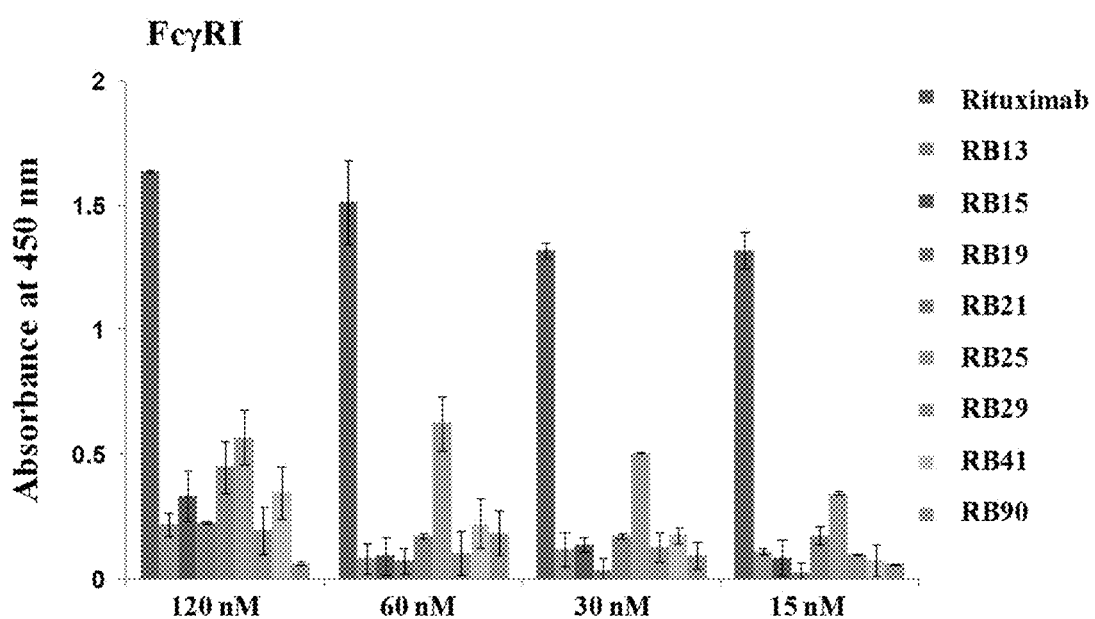
FIGS. 7A-F: ELISA results of glycosylated Rituximab (Glyco IgG1), and the selected IgG variants RB13, RB15, RB19, RB21, RB25, RB29, RB41, and RB90 to FcγRs; monomeric FcγRI (FIG. 7A), dimeric FcγRIIA$_{H131}$ (FIG. 7B), dimeric FcγRIIA$_{R131}$ (FIG. 7C), dimeric FcγRIIB (FIG. 7D) dimeric FcγRIIIA$_{V158}$ (FIG. 7E), and dimeric FcγRIIIA$_{F158}$ (FIG. 7F).
Figure 7B:
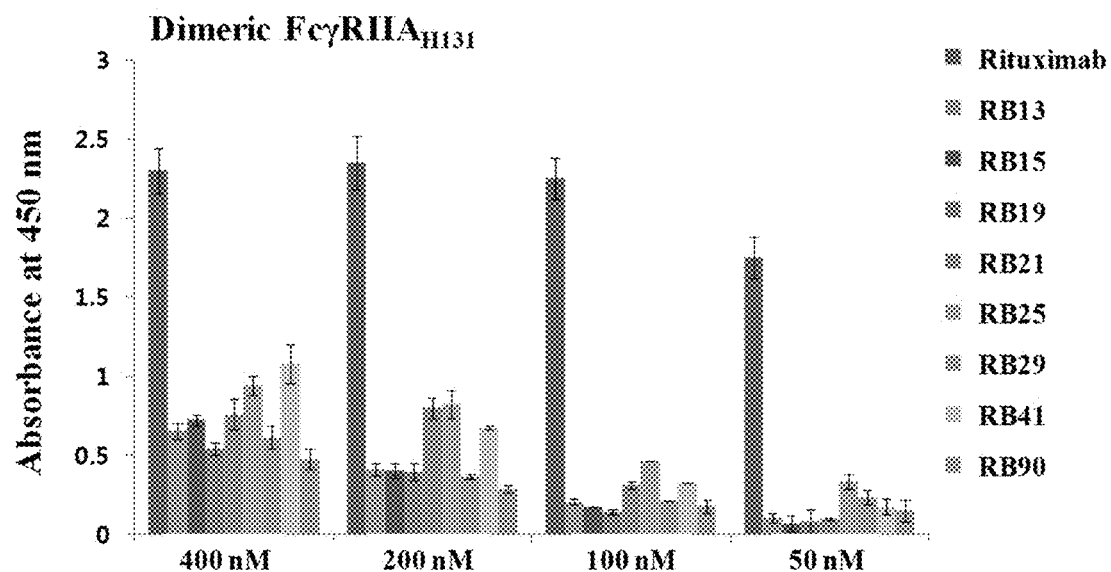
Figure 7C:
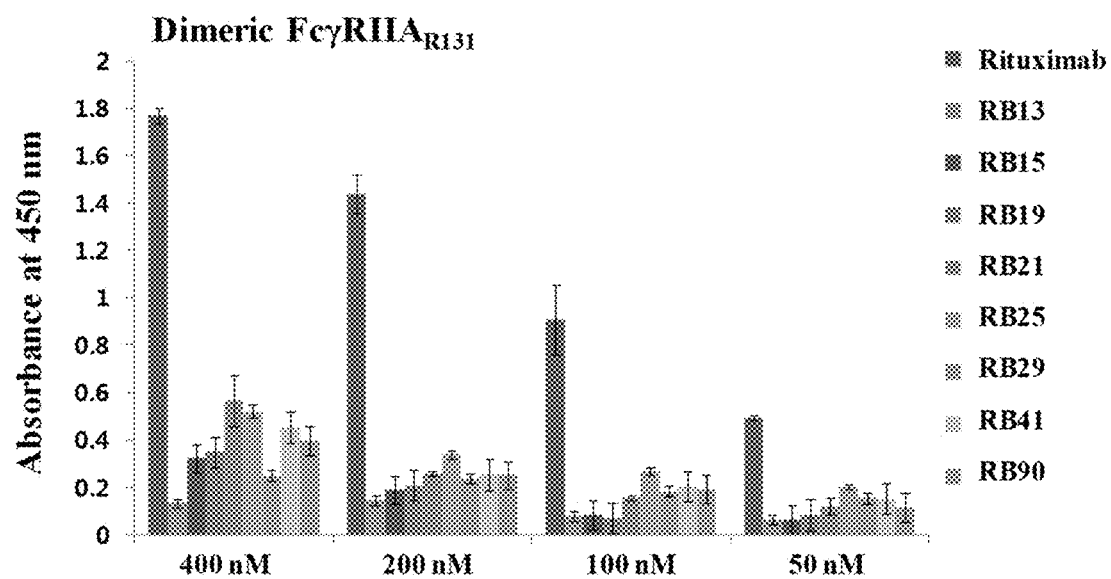
Figure 7D:
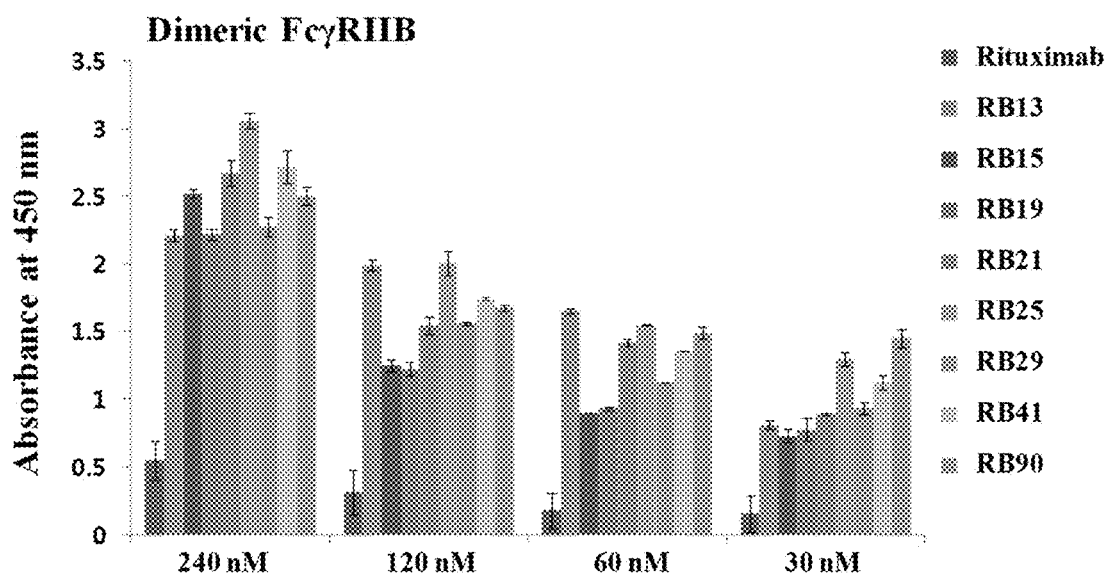
Figure 7E:
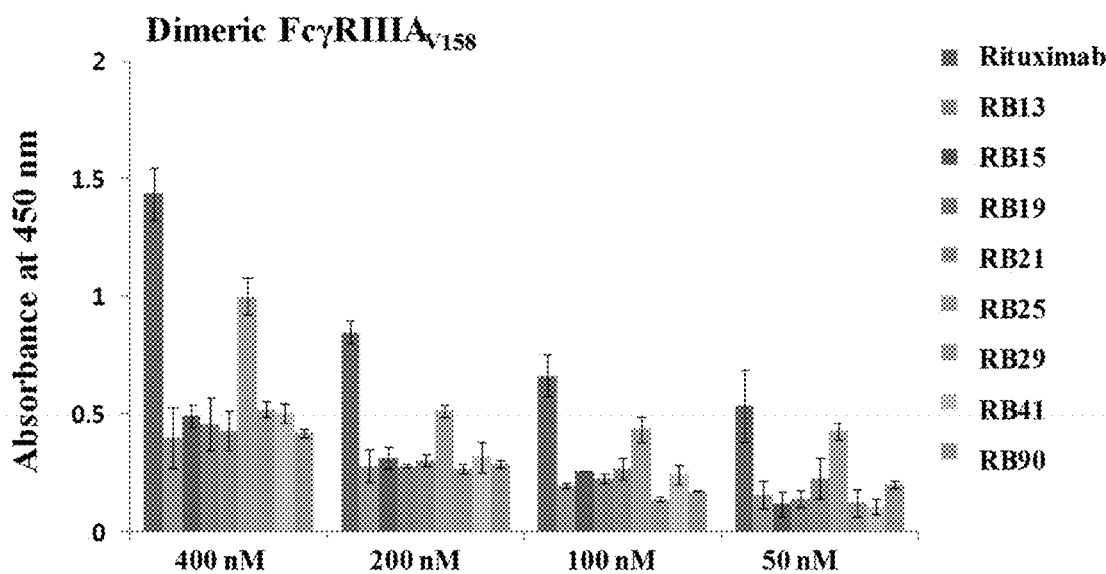
Figure 7F:
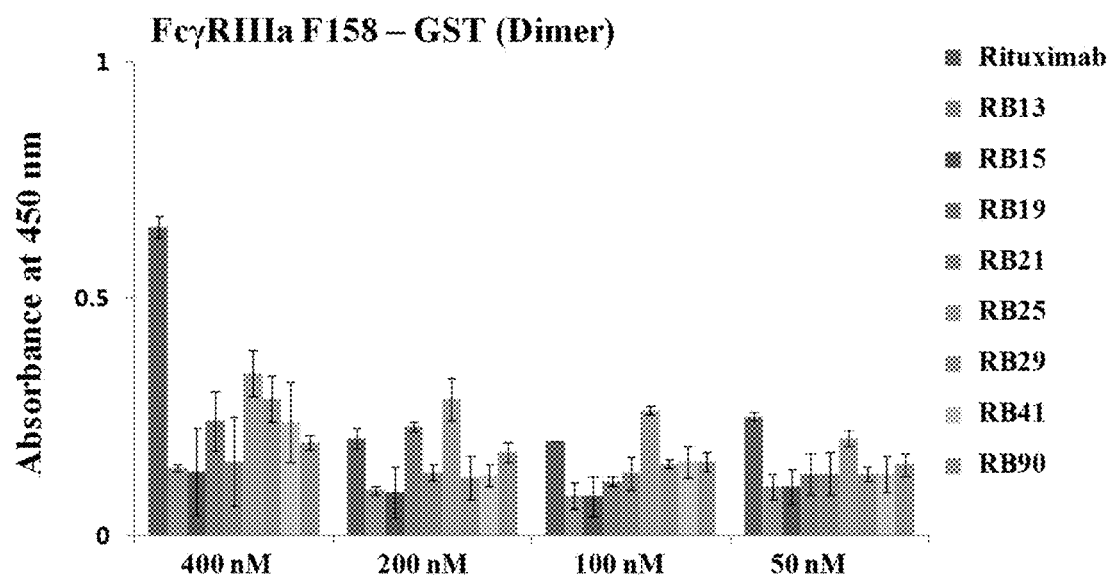

ELISA measurements of eight IgG variants with hFcγRs: 1 μg of each of RB13, RB15, RB19, RB21, RB25, RB29, RB41, RB90, or glycosylated Rituximab were coated onto a 96-well EIA/RIA plate (Qiagen) at 4° C. overnight, and the plates were washed three times with PBS containing 0.05% Tween® 20 (PBST). The plates were blocked for 1 h at room temperature with 3% skim milk in PBS and washed three times with PBST. Serially diluted monomeric FcγRI (120 nM-15 nM), dimeric $FcγRIIA_{R131}$ (400 nM-50 nM), dimeric $FcγRIIA_{H131}$ (400 nM-50 nM), dimeric FcγRIIB (240 nM-30 nM), dimeric $FcγRIIIA_{V158}$ (400 nM-50 nM), or dimeric $FcγRIIIA_{F131}$ (400 nM-50 nM) were then added to the plates. After 1 h of incubation at room temperature, the plates were washed with PBST and then they were incubated with 50 μL of PBS containing 1:5000 goat anti-His or anti-GST HRP (GE Healthcare) for 1 h. After washing with PBST three times, 50 μL TMB substrate was added per well (Thermo Scientific), 50 μL of 1 M $H_2SO_4$ was added to neutralize, and the absorbance at 450 nm was recorded. The high affinity IgG receptor, FcγRI, and the low affinity IgG receptors, FcγRIIA and FcγRIIIA, bind to IgG1 with dissociation constants (KD) in ranges of 0.1-10 nM and 0.1-1 μM, respectively. The native IgG1 showed very high binding activities with 15 nM of FcγRI but the isolated seven IgG variants, which are RB13, RB15, RB19, RB21, RB29, RB41, and RB90, did not show any binding activities with 15 nM of FcγRI and RB25 showed very weak binding activities for FcγRI (FIG. 7A). For dimeric $FcγRIIA_{H131}$, native IgG1 showed saturated binding activities with 200 nM of dimeric $FcγRIIA_{H131}$, but the isolated eight IgG variants did not show any binding activities under same condition (FIG. 7B). Similarly, the isolated eight IgG variants showed no binding with dimeric $FcγRIIA_{R131}$ $FcγRIIIA_{V158}$ and $FcγRIIIA_{F158}$ (FIG. 7C, E-F). However, the eight engineered IgG variants strongly bound to dimeric FcγRIIB with an apparent affinity higher than Rituximab (w.t. human IgG antibody control). B13, B21, and B25 showed particularly high binding to FcγRIIB.

TABLE 6

Binding affinity of Fc engineered IgG variants for human FcγRs measured by ELISA

|  | Monomeric FcγRI | Dimeric Fcγ RIIA$_{R131}$ | Dimeric Fcγ RIIA$_{H131}$ | Dimeric Fcγ RIIB | Dimeric Fcγ RIIIA$_{F158}$ | Dimeric Fcγ RIIIA$_{V158}$ |
|---|---|---|---|---|---|---|
| wtFc | 1.513 | 1.439 | 2.352 | 0.183 | 0.2035 | 0.8475 |
| RB13 | 0.0834 | 0.1478 | 0.4109 | 1.647 | 0.095 | 0.281 |
| RB15 | 0.093 | 0.1913 | 0.4011 | 0.898 | 0.091 | 0.3125 |
| RB19 | 0.0754 | 0.2088 | 0.3941 | 0.931 | 0.2295 | 0.2805 |
| RB21 | 0.1748 | 0.2587 | 0.798 | 1.418 | 0.133 | 0.3045 |
| RB25 | 0.623 | 0.338 | 0.8229 | 1.547 | 0.2865 | 0.5135 |
| RB29 | 0.1052 | 0.2378 | 0.3654 | 1.126 | 0.122 | 0.2695 |
| RB41 | 0.2234 | 0.2525 | 0.6745 | 1.354 | 0.1265 | 0.318 |
| RB90 | 0.184 | 0.2512 | 0.2867 | 1.491 | 0.1755 | 0.288 |

These values are the absorbance values at 450 nm under certain concentrations of FcγRs (60 nM FcγRI, 200 nM dimeric FcγRIIA$_{H131}$, 200 nM dimeric FcγRIIA$_{R131}$, 60 nM dimeric FcγRIIB Dimeric, 200 nM FcγRIIIA$_{F158}$, 200 nM dimeric FcγRIIIA$_{V158}$).

Figure 8A:
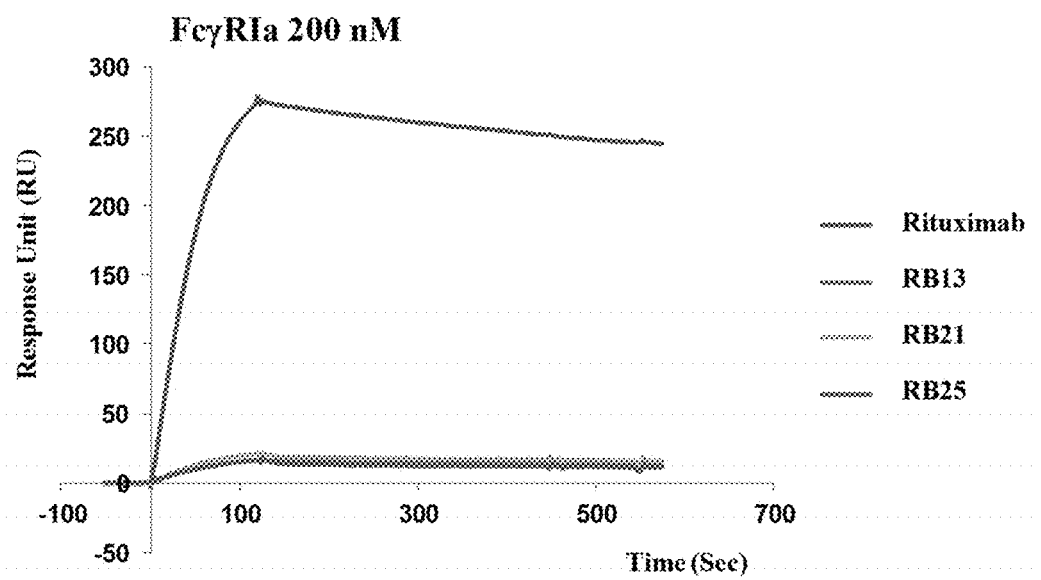
FIGS. 8A-E: The kinetic properties and surface plasmon resonance (SPR) sensorgrams of Rituximab, and the selected IgG variants RB13, RB21, and RB25 for monomeric FcγRI (FIG. 8A), dimeric FcγRIIA$_{H131}$ (FIG. 8B), dimeric FcγRIIA$_{R131}$ (FIG. 8C), dimeric FcγRIIIA$_{V158}$ (FIG. 8D), and dimeric FcγRIIIA$_{F158}$ (FIG. 8E).
Figure 8B:
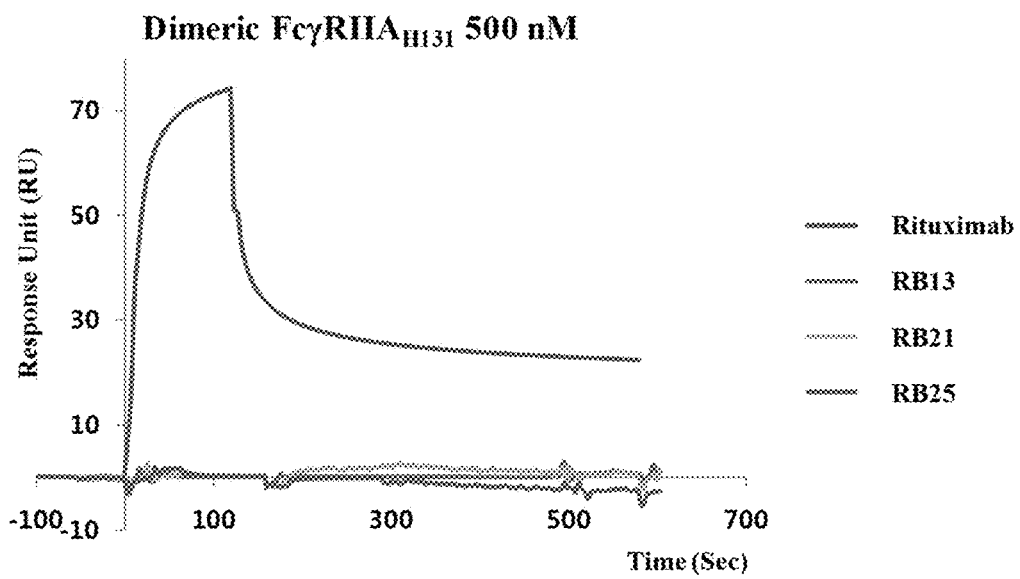
Figure 8C:
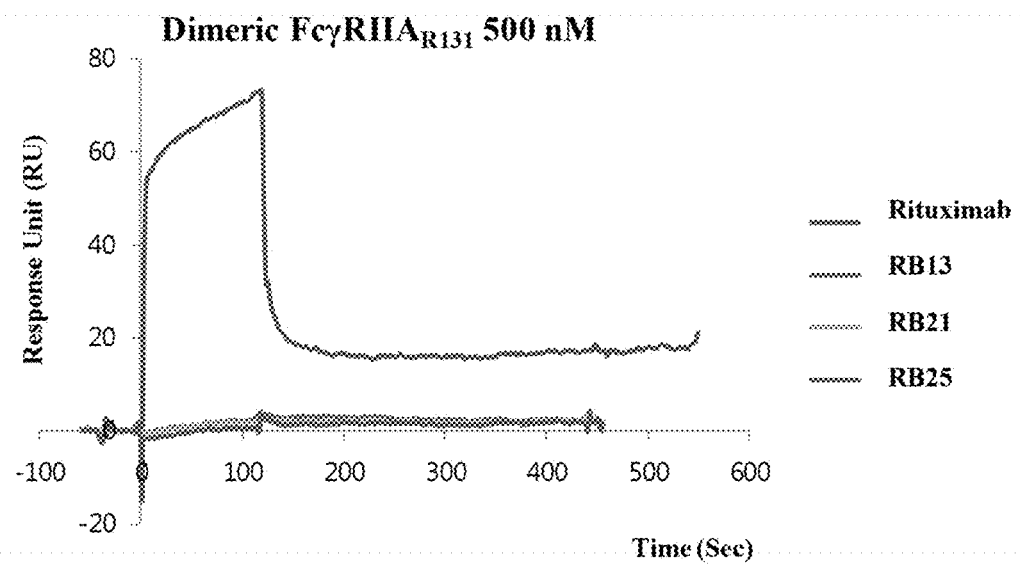
Figure 8D:
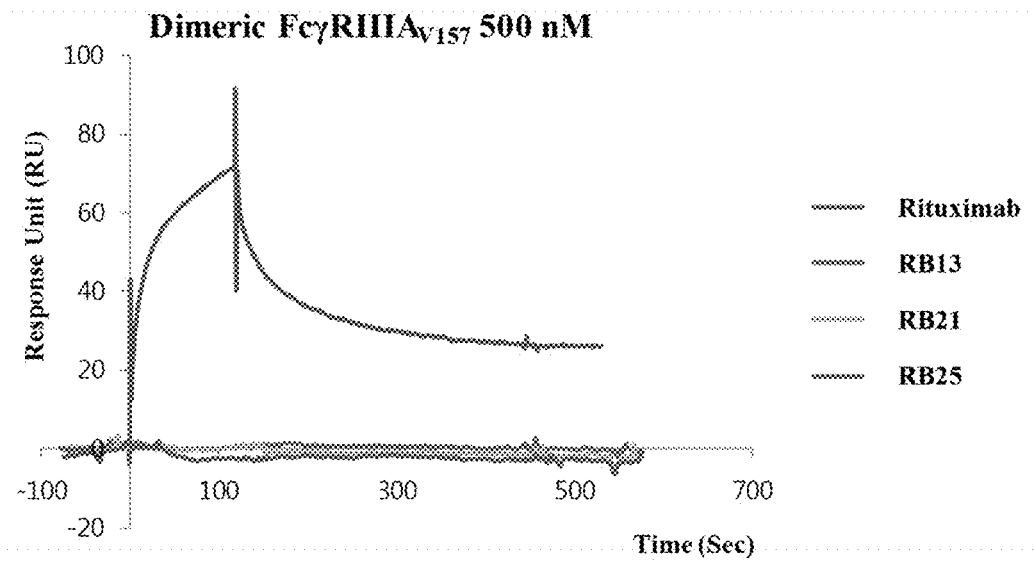
Figure 8E:
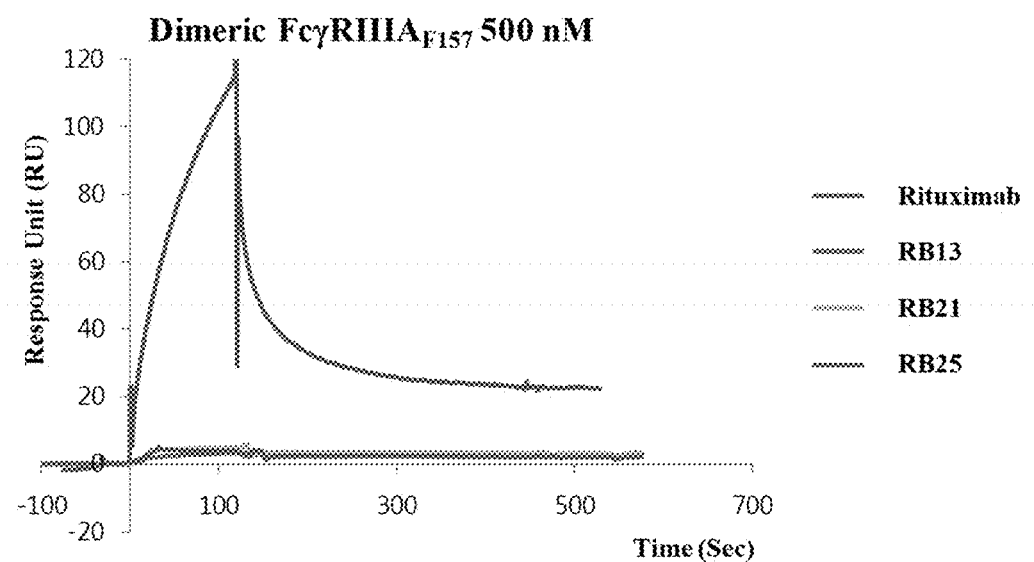
Figure 9A:
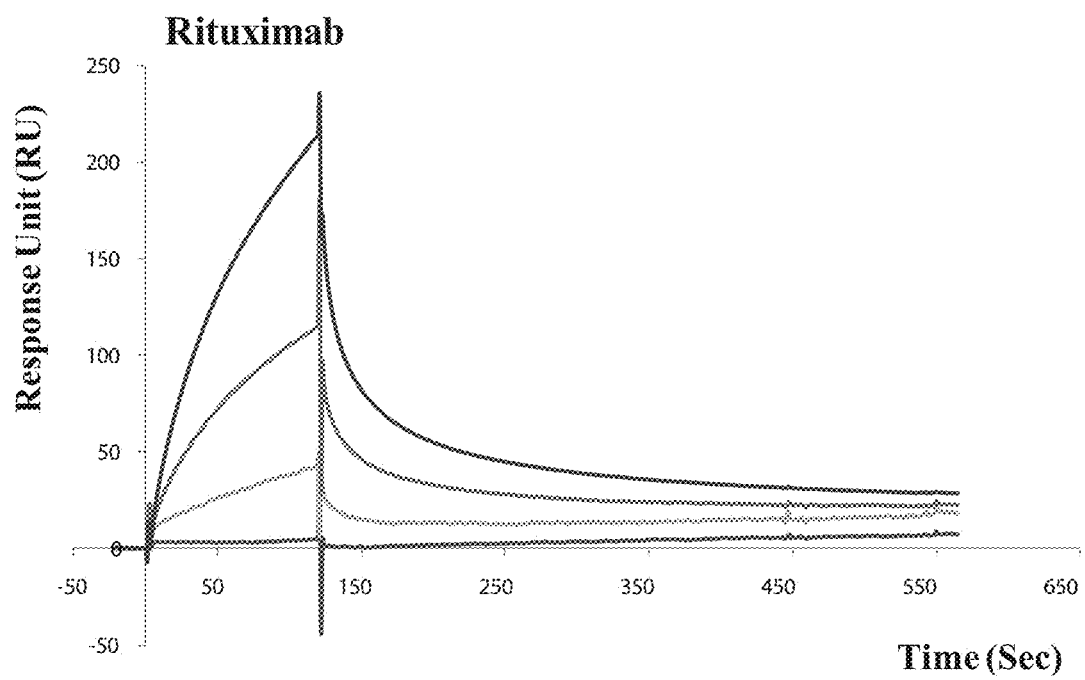
FIGS. 9A-D: The binding kinetic properties and surface plasmon resonance (SPR) sensorgrams of Rituximab (FIG. 9A), RB13 (FIG. 9B), RB21 (FIG. 9C), and RB25 (FIG. 9D) with FcγRIIB. The kinetic values of Rituximab, RB13, RB21, and RB25 for monomeric FcγRIIB are summarized in Table 7.
Figure 9B:
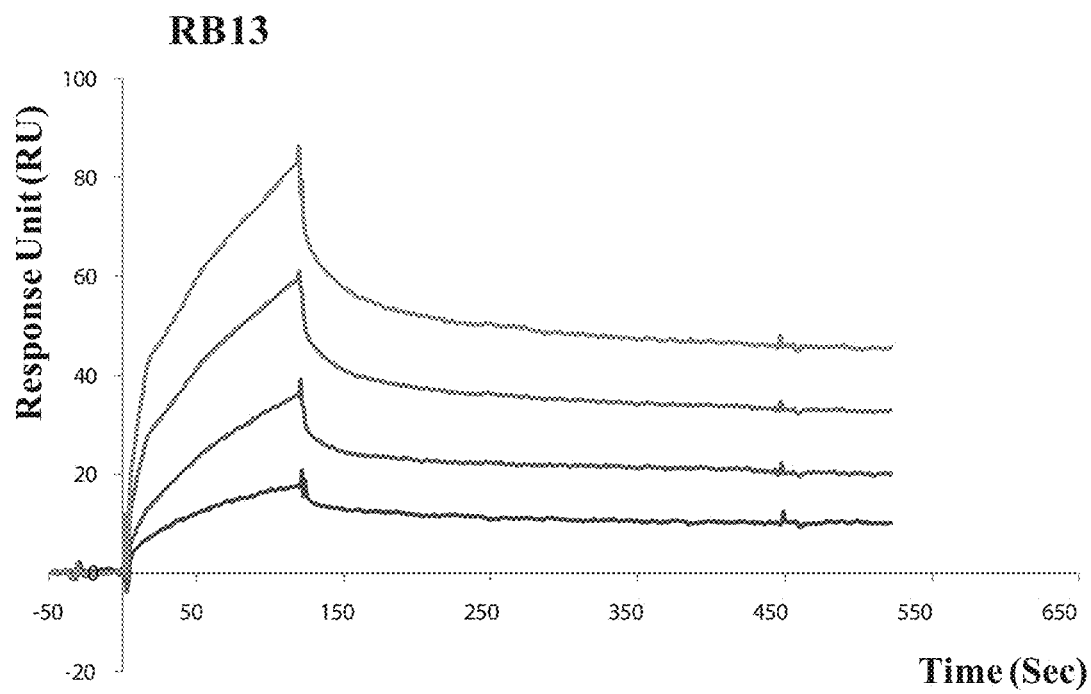
Figure 9C:
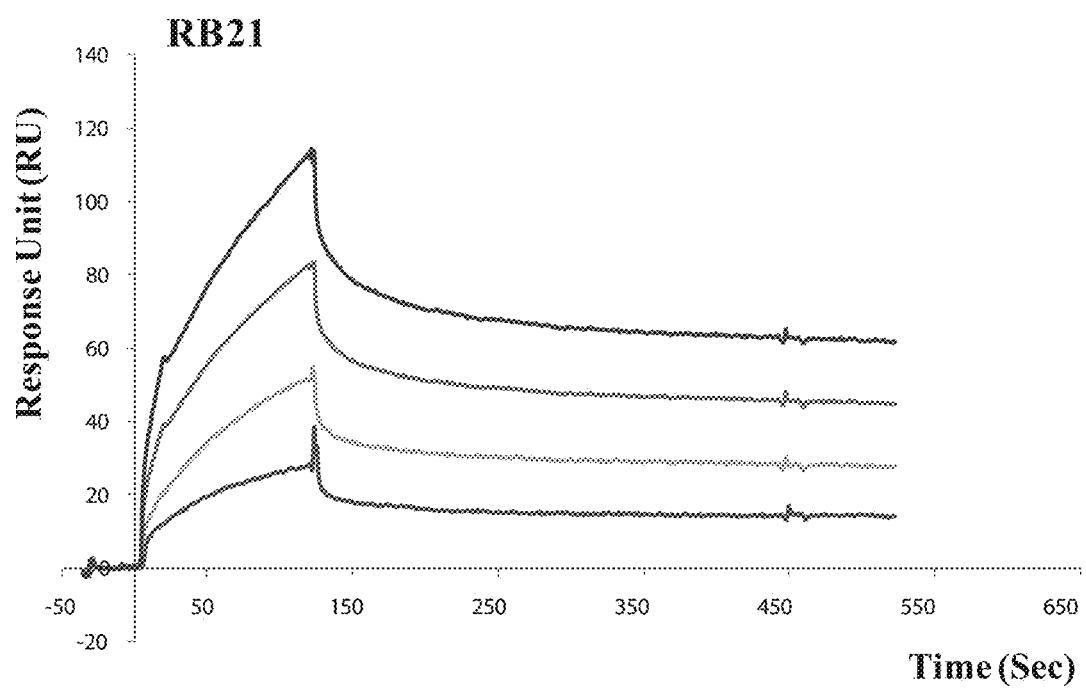
Figure 9D:
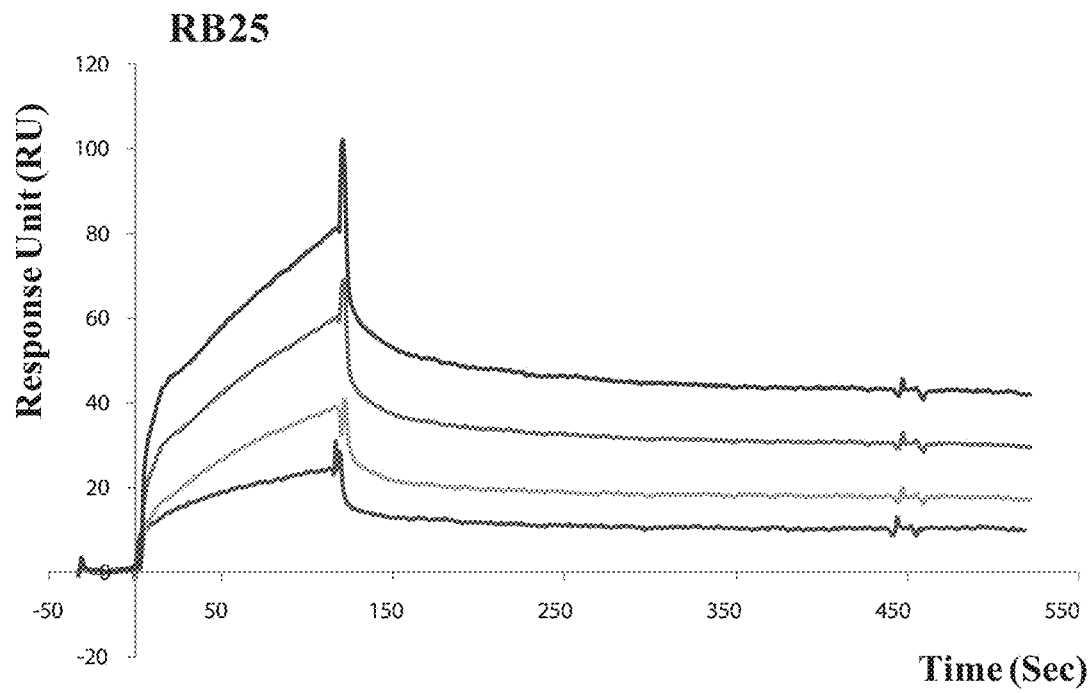

SPR Measurements:

SPR measurements were performed on Biacore® 3000 (GE Healthcare) instrument. Bovine serum albumin (BSA) was immobilized in the reference channels of the CM5 sensor chip to subtract buffer effect and non-specific binding signal. Rituximab, RB13, RB21, and RB25 were immobilized on the CM5 sensor chips by amine coupling at pH 5.0. Because native IgG1 has dissociation constants (KD) in ranges of 0.1-10 nM for FcγRI, and 0.1-10 μM for FcγRIIA and FcγRIIIA, the 200 nM monomeric FcγRI, 500 nM dimeric FcγRIIA$_{R131}$, 500 nM dimeric FcγRIIA$_{H131}$, 500 nM dimeric FcγRIIIA$_{V158}$, and 500 nM dimeric FcγRIIIA$_{F158}$ were injected to determine the binding activities of RB13, RB21 and RB25. Serially diluted dimeric FcγRIIB (75 nM-600 nM) was injected onto the CM5 chip at 30 μL/min for 2 min. The chip was regenerated after each binding event with 10 mM glycine (pH3.0) with a contact time of 1 min. The resulting sensorgrams were fit with a bivalent model for dimeric FcγRIIB using Biaevaluation 3.0 software (FIG. 9; Table 7). Native IgG1 showed 260 RU$_{max}$ for FcγRI but RB13, RB21, and RB25 showed about 6% RU$_{max}$ relative to native IgG1 for FcγRI (FIG. 8A). Similar to the ELISA results in Table 6 above, RB13, RB21, and RB25 showed very weak binding affinity towards to FcγRI. Dimeric FcγRIIA$_{H131}$, dimeric FcγRIIA$_{R131}$, dimeric FcγRIIIA$_{F158}$, and dimeric FcγRIIIA$_{V158}$, RB13, RB21, and RB25 did not show any binding activities (FIGS. 8B-E). The K$_D$ of RB13 with FcγRIIB was equal to 35.9 nM, a decrease in the K$_D$ of 224.9-fold relative to wild-type IgG1 (FIG. 9B; Table 7). The K$_D$ value for RB21 with FcγRIIB was 169 nM, a 47.7-fold higher affinity relative to wild-type IgG1 (FIG. 9C; Table 7). The K$_D$ of RB25 with FcγRIIB is 590 nM, a 13.7-fold higher affinity relative to relative to wild-type IgG1 (FIG. 9D; Table 7).

TABLE 7

Kinetic properties and surface plasmon resonance (SPR) sensorgrams of Rituximab, RB13, RB21, and RB25 with FcγRIIB (data correspond to FIGS. 9 A-D)

|  | k$_{on1}$ (1/Ms) | k$_{off1}$ (1/s) | k$_{on2}$ (1/RU) | k$_{off2}$ (1/s) | k$_{D1}$ | k$_{D2}$ | K$_D$ (nM)$^a$ | Fold$^b$ | chi$^2$ |
|---|---|---|---|---|---|---|---|---|---|
| Wt | $1.78 \times 10^3$ | $1.54 \times 10^{-2}$ | $6.19 \times 10^{-4}$ | $8.14 \times 10^{-5}$ | $8.69 \times 10^{-6}$ | $1.31 \times 10^1$ | $8.07 \times 10^{-6}$ | 1 | 0.776 |
| RB13 | $8.91 \times 10^3$ | $9.50 \times 10^{-4}$ | $6.55 \times 10^{-4}$ | $3.33 \times 10^{-4}$ | $1.07 \times 10^{-7}$ | $5.08 \times 10^{-1}$ | $3.59 \times 10^{-8}$ | 224.9 | 0.116 |
| RB21 | $2.86 \times 10^3$ | $9.60 \times 10^{-4}$ | $1.18 \times 10^{-4}$ | $1.19 \times 10^{-4}$ | $3.36 \times 10^{-7}$ | $1.01 \times 10^{-0}$ | $1.69 \times 10^{-7}$ | 47.7 | 0.103 |
| RB25 | $4.08 \times 10^3$ | $4.47 \times 10^{-3}$ | $1.60 \times 10^{-4}$ | $1.87 \times 10^{-4}$ | $1.10 \times 10^{-6}$ | $1.17 \times 10^{-0}$ | $5.90 \times 10^{-7}$ | 13.7 | 0.146 |

K$_D^a$ = K$_{D1}$/(1 + 1/K$_{D2}$) from a bivalent model fit of SPR data
Fold$^b$ = K$_D$ (Native IgG1)/K$_D$(IgG variant)

Example 8—Further Engineering of B13, B21, and B25 Fc Variants

Figure 10:
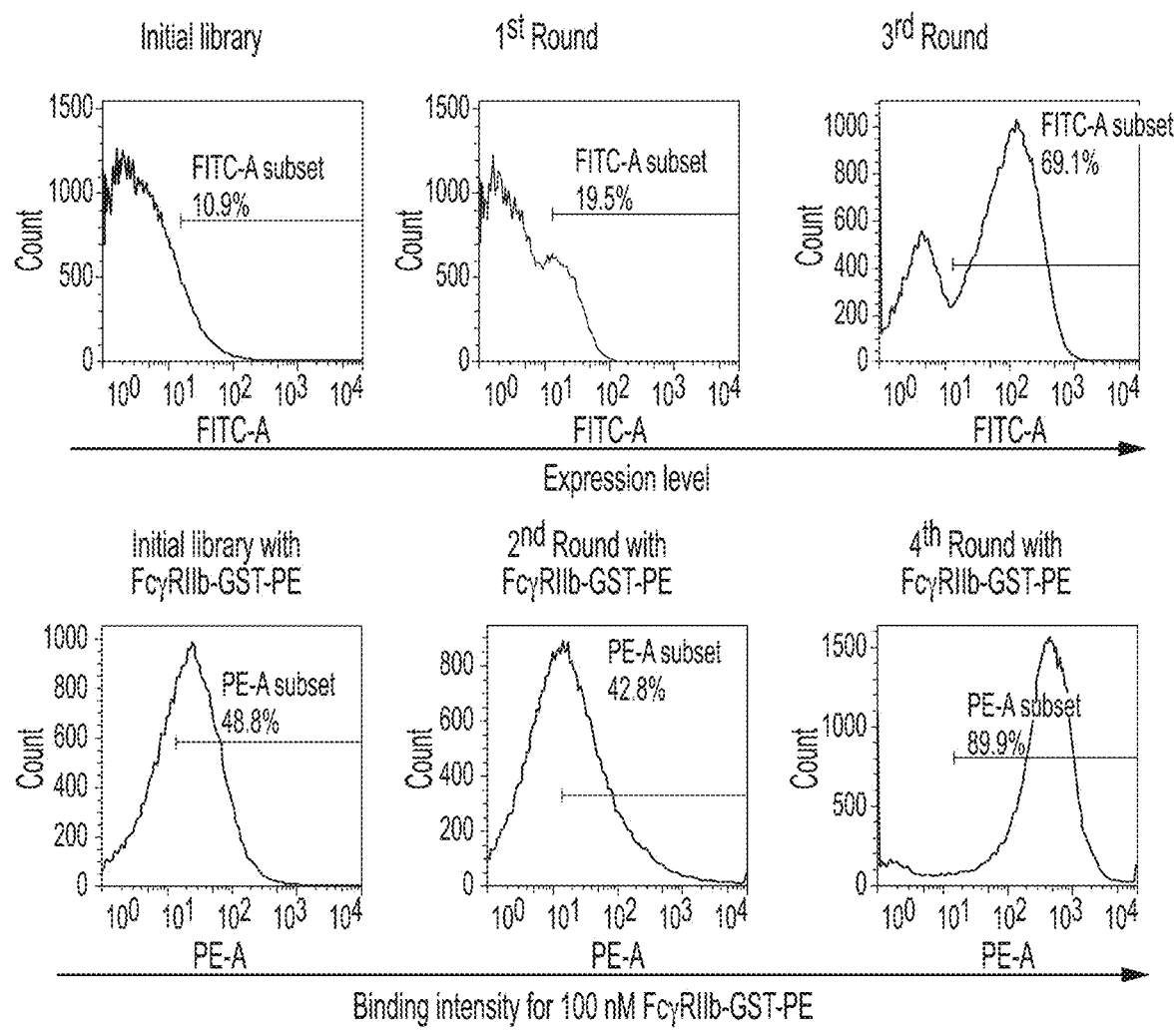
FIG. 10: FACS analysis histograms showing enrichment of E. coli cells expressing antibodies with mutated Fc domains that confer high expression level or affinity binding to hFcγRIIB. In upper panels, the antibodies-expressing spheroplasts are labeled with anti-myc Ab with FITC for detection of antibody expression level. In lower panels, the antibodies-expressing spheroplasts are labeled with 100 nM of human FcγRIIB-GST-PE. Fluorescent intensity of cells that bind with fluorescently labeled anti-myc Ab or FcγRIIB after each of five rounds of library sorting are shown.

In order to enhance the yield and stability of B13, B21, and B25 Fc, the respective genes were subjected to random mutagenesis by error prone PCR under conditions where the mutation rate was 1%, using the same methods as in Example 2. The error prone libraries were pooled and screened in two different ways in order to isolate Fc variants that maintain the same binding characteristics as B13, B21, and B25 Fc but can be expressed at a higher level than these Fc variants: First, the pooled library was labeled and screened with anti-myc Ab-FITC, which can detect the expression level of antibodies, at 1$^{st}$ and 3$^{rd}$ rounds by FACSAria™ (BD Biosciences) to select for enhanced expression level. Second, the library was labeled and screened with 100 nM FcγRIIb-GST-PE in the presence of 1 μM activating FcγRs as a competitor after the 2$^{nd}$ and 4$^{th}$ rounds by FACSAria™ (BD Biosciences). Fluorescence profiles during screening are shown in FIG. 10.

Figure 11A:
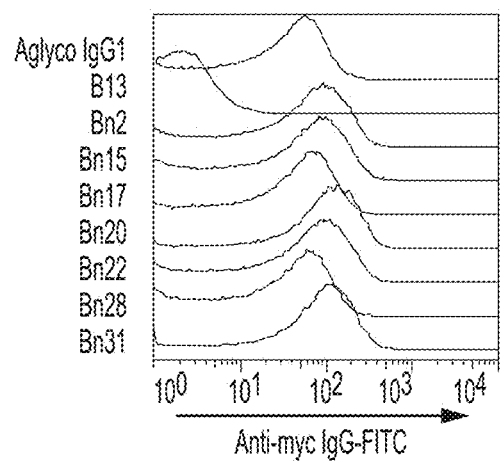
FIGS. 11A-B: FACS analysis histograms of the seven isolated IgG variants for detecting the expression level (FIG. 11A) or hFcγRIIB-binding intensity (FIG. 11B). As controls, wild type aglycosylated IgG and aglycosylated RB13 were assayed with same conditions.
Figure 11B:
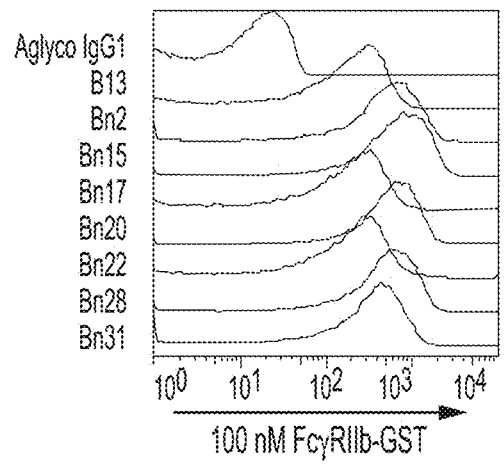

Fifty randomly selected IgG variants from the last (4$^{th}$) round of library sorting were sequenced and found to encode only 7 different Fc variants (represented at multiple copies in the pool of 50 selected clones). Fc-Bn2 has six mutations, K246Q, T260A, L351Q, Q386R, P396F, and V397M. Fc-Bn15 has two mutations, Y296C, and Q386R. Fc-Bn17 has 8 mutations, K246Q, T260A, N315S, I336M, K340R, Q342D, A378T, Q386R. Fc-Bn20 has 5 mutations, T260A, L351Q, Q386R, P396S, and V397M. Fc-Bn22 has four mutations, L351Q, Q386R, P396S, and V397M. Fc-Bn28 has 6 mutations, V264A, Y296C, N297Q, Q311K, R344Q, and Q418R. Fc-Bn31 has two mutations, V264A and N297Q. Fc variant-expressing cells were labeled and analyzed with 100 nM of FcγRIIb-GST-PE (FIG. 11 and Table 9). The seven isolated aglycosylated IgG variants showed 1.0-3.0 fold enhanced expression levels than aglycosylated IgG1 and 5-15 fold enhanced expression levels than aglycosylated B13 Fc variant (Table 11 and FIG. 11A). The seven isolated aglycosylated IgG variants showed 6.6-15.2 fold higher MFI values for 100 nM dimeric FcγRIIb than aglycosylated IgG1 and 1.3-3.0 fold higher MFI values for 100 nM dimeric FcγRIIb than aglycosylated B13 Fc variant (Table 11 and FIG. 11B).

TABLE 11

Binding analysis of the isolated ten IgG variants with anti-myc Ab-FITC or FcγRIIb-GST-PE using FACS (data correspond to FIG. 11A&B)

|  | Expression | | FcγRIIb-GST-PE | |
| --- | --- | --- | --- | --- |
|  | MFI | Increasing Fold | MFI | Increasing Fold |
| Aglyco IgG1 | 39.0 | 1 | 23.5 | 1 |
| B13 | 6.21 | 0.2 | 118 | 5.0 |
| Bn2 | 61.4 | 1.6 | 333 | 14.2 |
| Bn15 | 57.0 | 1.5 | 358 | 15.2 |
| Bn17 | 54.8 | 1.4 | 318 | 13.5 |
| Bn20 | 117 | 3.0 | 289 | 12.3 |
| Bn22 | 62.5 | 1.6 | 154 | 6.6 |
| Bn28 | 37.7 | 1.0 | 176 | 7.5 |
| Bn31 | 98.7 | 2.5 | 228 | 9.7 |

Example 9—Construction, Expression and Purification of the Further Engineered IgG Variants All plasmids and primers are described in Tables 8 and 9. All detailed methods for constructing of IgG variants-expressing vector are described in Example 6. The three mutant Fc genes, Bn2, Bn15, and Bn17, were amplified from pMopac12-pelB-IgG-VH-CH1-mFc-FLAG were amplified from pMopac12-pelB-IgG-VH-CH1-CH2-CH3-FLAG using two specific primers (TH083 (SEQ ID NO: 14) and TH084 (SEQ ID NO: 15)). These IgH genes were cloned into pcDNA3.4 using a Gibson Assembly®cloning kit (NEB) according to the manufacturer's instructions (Jung et al., 2012). The T299L mutation was introduced in all three IgG variants using two specific primers: WK68 (SEQ ID NO: 18) and WK69 (SEQ ID NO: 19), as described previously (Jung et al., 2012). These aglycosylated Fc variants received the names ABn2, ABn15, and ABn17. The heavy chain genes were transiently transfected with an equal mass of light chain plasmid in HEK293F cells (Invitrogen). The buffer of all purified IgG variants was exchanged to PBS by Amicon® Ultra-4 (Millipore). The purity of the purified antibodies was assessed by 4%-20% gradient SDS-PAGE gel (NuSep) under reducing and non-reducing conditions.

Example 10—Binding Properties of the Further Engineered IgG Variants to FcγRs

Affinities of the further engineered IgG variants with human FcγRs were evaluated with enzyme-linked immunosorbent assay (ELISA). Additional methods and results are described below.

Figure 12A:
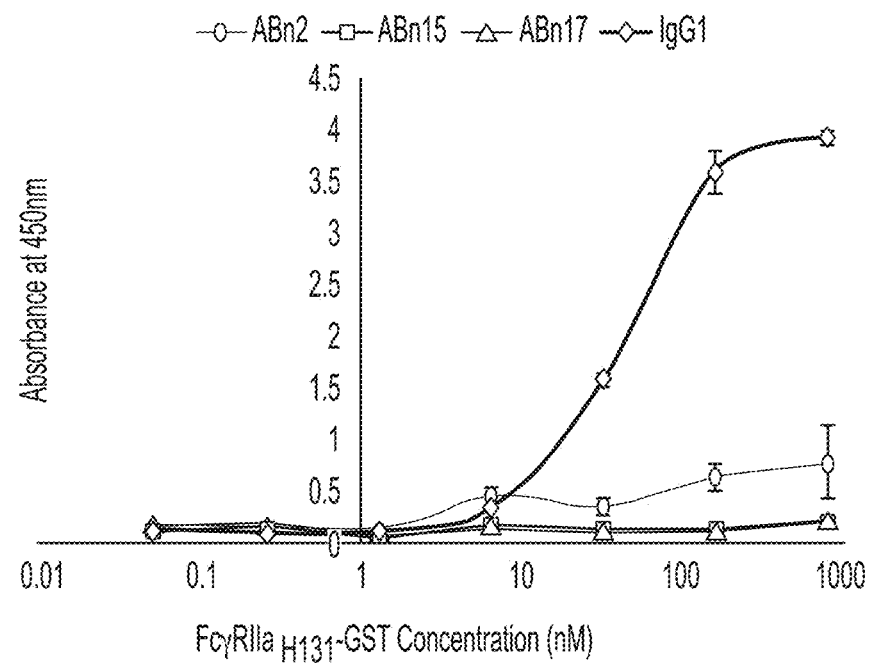
FIGS. 12A-D: ELISA results of glycosylated IgG1 (IgG1), and the three selected IgG variants ABn2, ABn15, and ABn17 to FcγRs; dimeric FcγRIIA$_{H131}$ (FIG. 12A), dimeric FcγRIIA$_{R131}$ (FIG. 12B), monomeric FcγRIIB (FIG. 12C), and dimeric FcγRIIIA$_{V158}$ (FIG. 12D).
Figure 12B:
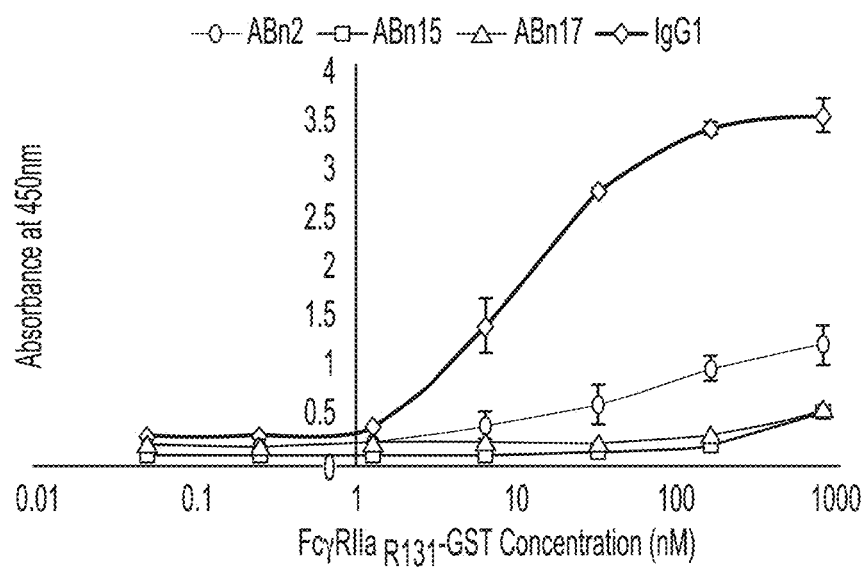
Figure 12C:
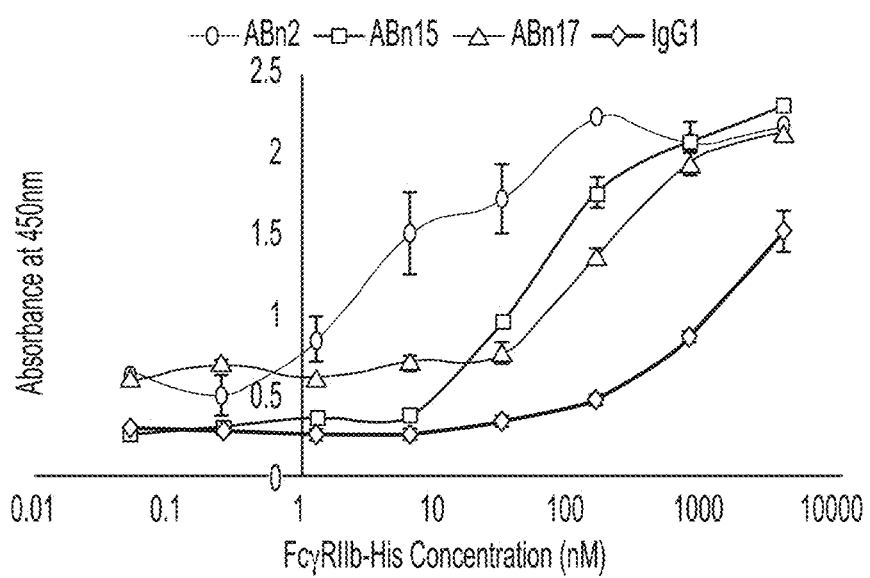
Figure 12D:
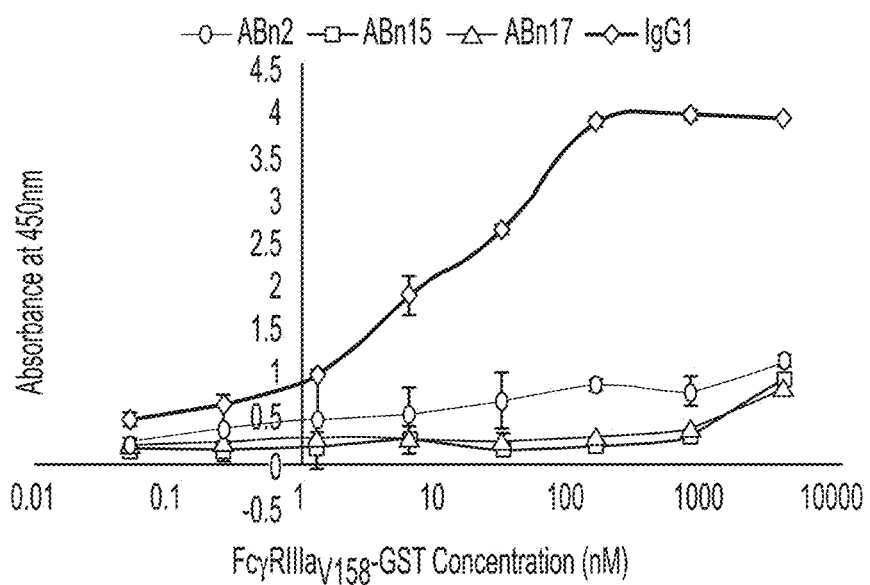

ELISA Measurements of IgG Variants with FcγRs:

The 1 μg of IgG variants, ABn2, ABn15, or ABn17 was coated onto a 96-well EIA/RIA plate (Qiagen) at 4° C. overnight, and the plates were washed three times with PBS containing 0.05% Tween® 20 (PBST). The plates were blocked for 1 h at room temperature with 3% bovine serum albumin (BSA) in PBS and washed three times with PBST. The fifty μl of the serial diluted dimeric FcγRIIa H131, dimeric FcγRIIa R131, dimeric FcγRIIIa V158 or monomeric FcγRIIb (4000 nM-0.05 nM) was added to the plates. After 1 h of incubation at room temperature, the plates were washed with PBST and were incubated with 50 μL of PBS containing 1:5000 goat anti-His HRP (GE Healthcare) for 1 h. After three times of washing with PBST, 50 μL TMB substrate was added per well (Thermo Scientific), 50 μL of 1 M $H_2SO_4$ was added to neutralize, and the absorbance at 450 nm was recorded. All three IgG variants showed the greatly enhanced binding activities than glycosylated wild type IgG1 for FcγRIIb-his. $IC_{50}$ values of ABn2 with FcγRIIb-his is 5±2 nM. $IC_{50}$ values of ABn15 with FcγRIIb-his is 45±8 nM. $IC_{50}$ values of ABn17 with FcγRIIb-his is 150±22 nM. $IC_{50}$ values of IgG1 with FcγRIIb-his is over 2 μM (FIG. 12B). But these IgG variants (ABn2, ABn15, and ABn17) showed a very weak binding signals for dimeric FcγRIIa H/R131 and dimeric FcγRIIIa V158 (FIG. 12A-D).

Example 11—Library Construction Strategy for the Isolation of Murine IgG1 Fc Domains that Bind to Murine FcγRII In order to engineer the Fc domain of murine IgG1 (mIgG1), the human Fc domain in pMopac12-pelB-IgG-VH-CH1-CH2-CH3-FLAG was replaced by Fc domain of mIgG1 (mFc). The mFc gene (UniProtKB—P01869) was synthesized by IDT and cloned into pMopac12 using a Gibson Assembly®cloning kit (NEB) according to the manufacturer's instructions (Jung et al., 2012). To isolate aglycosylated murine Fc (mFc) domain variants containing mutations that enable binding to murine FcγRII (mFcγRII) in the absence of the N297 glycan, the library was constructed based on Fc domain of mIgG1. A murine Fc library was constructed by error prone PCR with 1% error rate of the wild type Fc template using primers PCH50 (SEQ ID NO: 21) and PCH59 (SEQ ID NO: 20). The detailed procedures are described in Example 2.

Example 12—Preparation of Monomeric Murine FcγRs and Biotinylated Murine FcγRII

Plasmids for the mammalian expression of mFcγRs were constructed. The genes of mFcγRI-his tag, FcγRII-his tag, FcγRIII-his tag, and FcγRIV-his tag were synthesized by IDT. The mFcγR genes were cloned into pcDNA3.4 and the mFcγR-his tag proteins were produced by transient transfection of HEK293F cells (Invitrogen). The transfected HEK293F cells were cultured for 5 days in a 5% $CO_2$ incubator at 37° C. The supernatant was collected by centrifugation at 4,000×g for 10 min and filtered using a 0.22 m polyethersulfone (PES) membrane filter (PALL). Each mFcγR-His protein was purified with Ni-NTA (GE Healthcare) affinity columns according to the manufacturer's instructions. To remove lipopolysaccharide (LPS) and non-specifically bound protein, the FcγRs-bound resins were washed with 50 mL of PBS containing 0.1% Triton®X-114 (Sigma-Aldrich) and 50 mL of PBS. Each mFcγRs-His was eluted with PBS containing 250 mM imidazole. The buffer for all eluted mFcγR proteins was exchanged to PBS using an Amicon Ultra-4 (Millipore) unit.

The biotinylated mFcγRII (b-mFcγRII) was prepared under manufacturer's instructions. Briefly, one mg of mFcγRII was incubated with 20-fold excess amount of NHS-sulfo-biotin (Pierce) at 4° C. for 4 hours and purified by the desalting columns. And the concentration of biotinylated mFcγRII was measured by absorbance at 280 nm.

Example 13—Screening of mFc Library with mFcγRII

Spheroplasted *E. coli* JUDE-1 bacteria expressing the murine Fc(mFc) library were prepared with same procedure in Example 4 (Jung et al., 2010; Jung et al., 2012).

Figure 13:
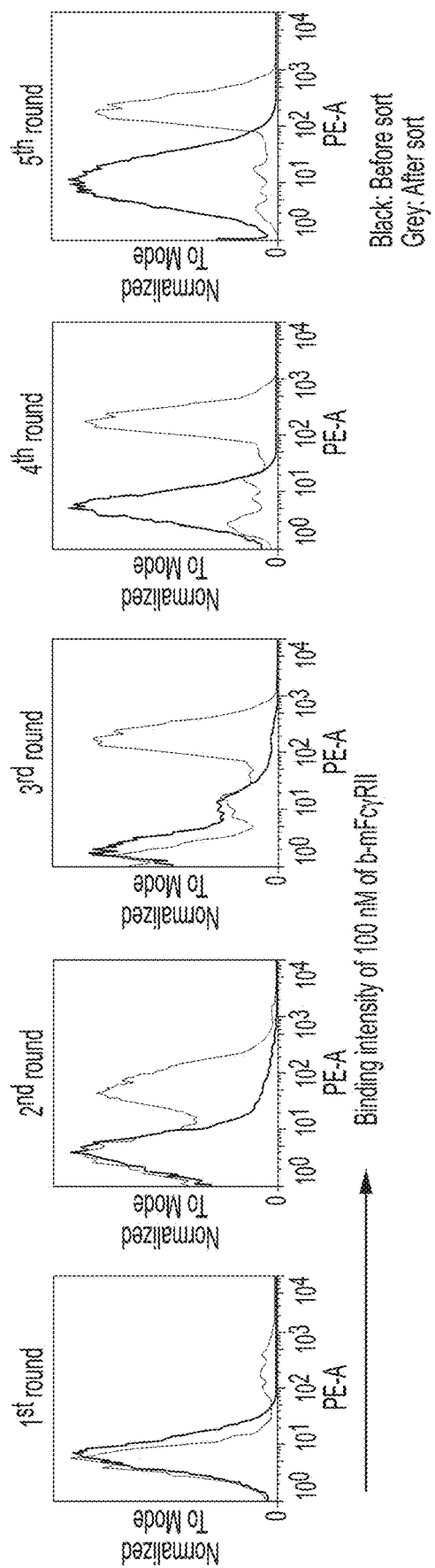
FIG. 13: FACS analysis histograms showing enrichment of E. coli cells expressing murine antibodies with mutated Fc domains that confer high affinity binding to murine FcγRII. The antibodies-expressing spheroplasts are labeled with 100 nM of murine b-FcγRII (b-m FcγRII). Fluorescent intensity of cells that bind with fluorescently labeled b-mFcγRII after each of five rounds of library sorting and resorting are shown. The right most peak represents the "after sorting" condition in each histogram.
Figure 14A:
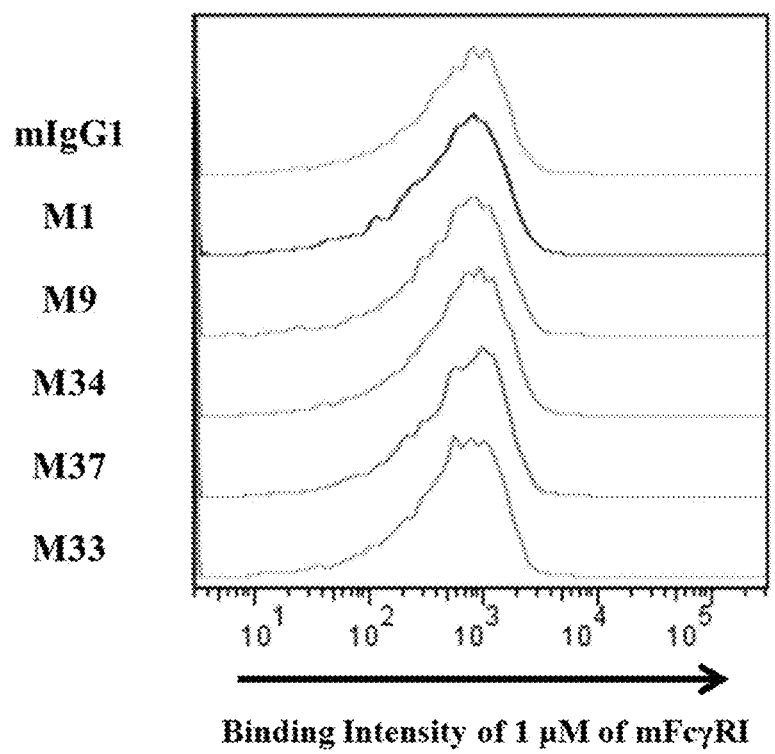
FIGS. 14A-D: FACS analysis histograms of the five isolated IgG variants for detecting the murine FcγRs (mFcγRs)-binding intensity. The selected IgG variants-expressing spheroplasts were labeled with 1 μM of mFcγRI (FIG. 14A), 100 nM of mFcγRII (FIG. 14B), 1 μM of mFcγRIII (FIG. 14C), or 1 μM of mFcγRIV (FIG. 14D). As controls, wild type aglycosylated murne IgG1 was assayed with same conditions.
Figure 14B:
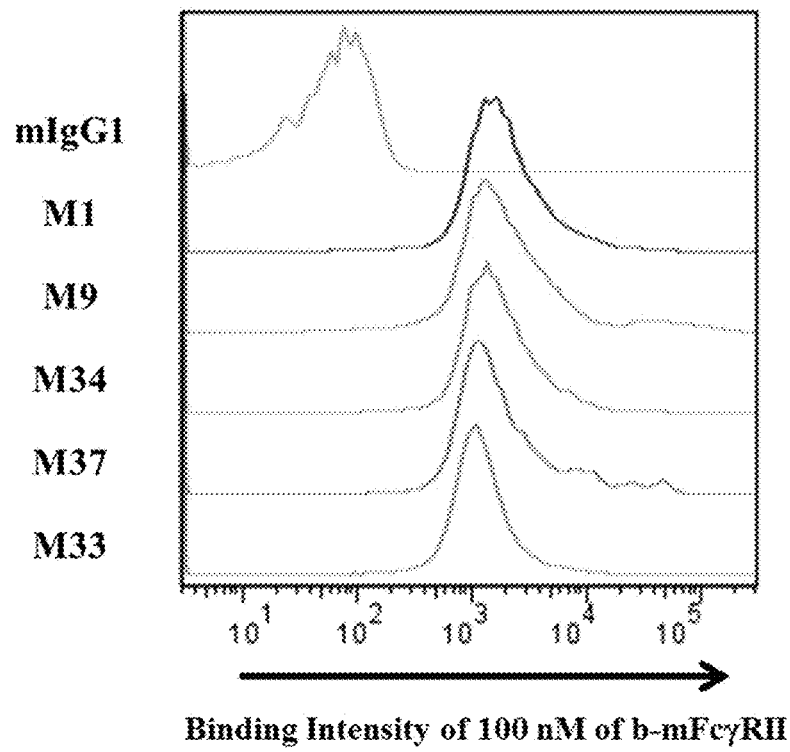
Figure 14C:
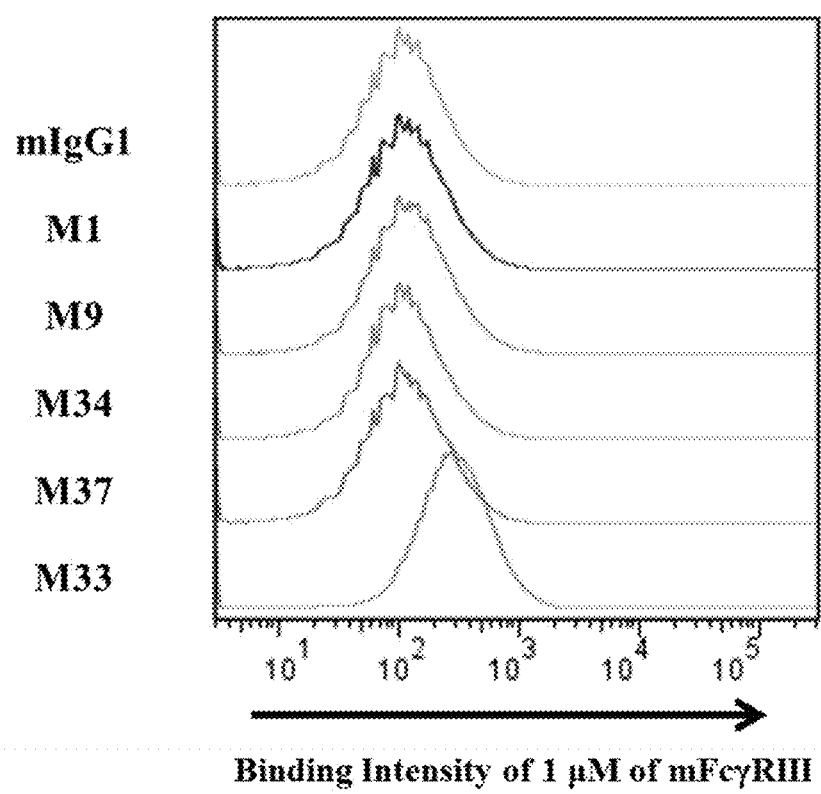
Figure 14D:
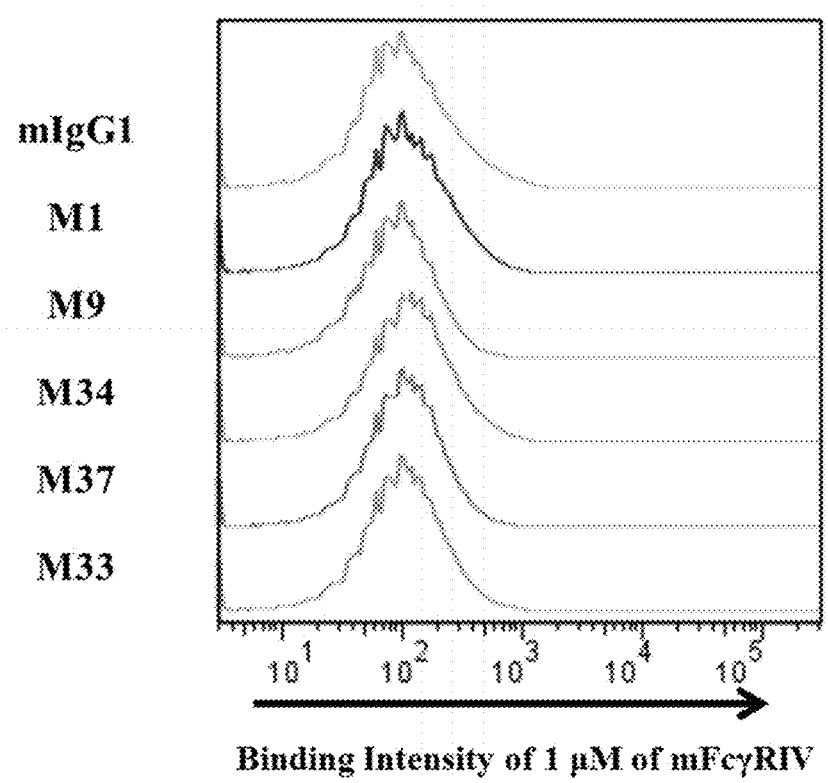

In order to isolate mFcγRII-specific aglycosylated mIgG1 variants, spheroplasted mFc library-expressing *E. coli* JUDE-1 cells were labeled with 100 nM of b-mFcγRII in the presence of 1 μM activating mFcγRs as a competitor and screened by on FACSAria™ (BD Biosciences). b-mFcγRII bound spheroplasted were labeled with Streptavidin-R-Phycoerythrin Conjugate (SA-PE) (Thermofisher). In each round, the top 1% of the population showing the highest fluorescence was recovered and these sorted spheroplasts were resorted immediately to remove false positives. The heavy chain genes in the sorted spheroplasts were rescued by PCR using two primers (PCH50 and PCH59) after boiling for 5 min and ligated into SfiI-cut pMopac12 vector. The ligated plasmids were transformed in *E. coli* JUDE-1 cells. Transformants were selected on chloramphenicol- and kanamycin-containing media. The reconstructed mFc library was screened with 100 nM of b-mFcγRII in the presence of 1 μM activating mFcγR for 5 rounds (FIG. 13).

Twenty randomly selected mIgG1 variants after fifth round of mFc-library screening with mFcγRII were sequenced. The identified different mIgG1 variants were five different Fc variants. The binding properties of these five final candidates were examined with 100 nM of b-mFcγRII or 1 μM of activating mFcγRs. The binding intensity of b-mFcγRII was detected by SA-PE and the binding intensity of other mFcγRs was detected by goat anti-His IgG-PE (Abcam). As shown in Table 12, all 5 mIgG variants showed 24.6-80.8 fold-higher mean fluorescence intensity (MFI) values relative to wild-type aglycosylated mIgG1 for 100 nM of b-FcγRIIB. All 5 mIgG1 variants showed very similar binding intensities for mFcγRI, mFcγRIII, and mFcγRIV with wild-type aglycosylated mIgG1 (Table 12 and FIG. 14A-D).

PCR of VH-CH1 genes and Fc genes using two specific primers (TH081 and PCH96) was performed to amplify whole IgH genes. These IgH genes were cloned into pcDNA3.4 using a Gibson Assembly®cloning kit (NEB) according to the manufacturer's instructions (Jung et al., 2012). The Gibson assembled mixtures were transformed into *E. coli* JUDE-1 cells and their sequences confirmed. Newly constructed Rituximab-mFc variants still have N-glycosylation sites on their CH2 domains. In order to construct their aglycosylated format, a T299L mutation, which does not affect the binding ability of the Fc domain with FcγRs, was introduced using two specific primers (PCH132 (SEQ ID NO: 24) and PCH133 (SEQ ID NO: 25)) as described previously (Jung et al., 2012). Rituximab-aglycosylated Fc variants received the names RAmFc1, RAmFc9, and RAmFc34. The anti-mouse CD40 antibodies also constructed. VH and VL gene of S2C6 was synthesized by IDT (U.S. Pat. No. 7,666,422). The pcDNA3.4-IgH S2C6-wild type mFc and pcDNA3.4-IgL S2C6 were constructed using a Gibson Assembly®cloning kit (NEB). S2C6-mFc variants expressing plasmids, pcDNA3.4-IgH-S2C6-mFc1, pcDNA3.4-IgH-S2C6-mFc9, and pcDNA3.4-IgH-S2C6-mFc34, were constructed using a Gibson Assembly®cloning kit (NEB). The heavy chain genes were transiently transfected with an equal mass of light chain plasmid in HEK293F cells (Invitrogen). After incubation in a 5% $CO_2$ incubator at 37° C. for six days, the supernatants were collected by centrifugation at 4,000×g for 10 min and filtered using a 0.22 m PES membrane filter (PALL). The filtered supernatants were passed over Protein G high capacity agarose resin (Thermo Scientific) three times. To remove LPS and non-specifically bound protein, the IgG-bound resins were washed with 50 mL PBS containing 0.1% Triton®X-114 (Sigma-Aldrich) and 50 mL PBS. All IgG variants were eluted with 100 mM glycine buffer (pH 3.0) and immediately neutralized with 1M Tris-HCl buffer (pH 8.0). The buffer of all eluted Rituximab-mFc variants was exchanged to PBS by Amicon® Ultra-4 (Millipore). The purity of the purified antibodies was assessed by 4%-20% gradient SDS-PAGE gel (NuSep) under reducing and non-reducing conditions.

TABLE 12

Binding analysis of the isolated five mFc variants with 100 nM mFcγRII or 1 μM of activating FcγRs using FACS (data correspond to FIG. 14A-D).

| Clone # | Aglycosyltated mIgG1 | mFc1 | mFc9 | mFc33 | mFc34 | mFc37 |
|---|---|---|---|---|---|---|
| 1 μM mFcγRI | 515 | 549/ | 532/ | 414/ | 527/ | 511/ |
| (MFI/Increasing Fold) | | 1.1 | 1.0 | 0.8 | 1.0 | 1.0 |
| 100 nM mFcγRII | 61.8 | 2477/ | 4995/ | 1520/ | 2420/ | 3617/ |
| (MFI/Increasing Fold) | | 40.1 | 80.8 | 24.6 | 39.2 | 58.5 |
| 1 μM mFcγRIII | 143 | 149/ | 165/ | 350/ | 146/ | 151/ |
| (MFI/Increasing Fold) | | 1.0 | 1.2 | 2.4 | 1.0 | 1.1 |
| 1 μM mFcγRIV | 155 | 145/ | 110/ | 135/ | 154/ | 130/ |
| (MFI/Increasing Fold) | | 0.9 | 0.7 | 0.9 | 1.0 | 0.9 |

Example 14—Construction, Expression and Purification of the Selected Mutant mIgG Variants All plasmids and primers are described in Tables 8 and 9. The three mutant mFc genes, mFc1, mFc9, and mFc34 were amplified from pMopac12-pelB-IgG-VH-CH1-mFc-FLAG using two specific primers (PCH059 and PCH096). The VH-CH1 gene was amplified from pcDNA3.4-IgH-Rituximab (Kelton et al., 2015) using two specific primers (TH081 and PCH109). Amplification of the overlapping Example 15—Binding Properties of the mIgG Variants to mFcγRII Affinities of STPK-Fc variants with human FcγRs were evaluated with enzyme-linked immunosorbent assay (ELISA). Additional methods and results are described below.

Figure 15:
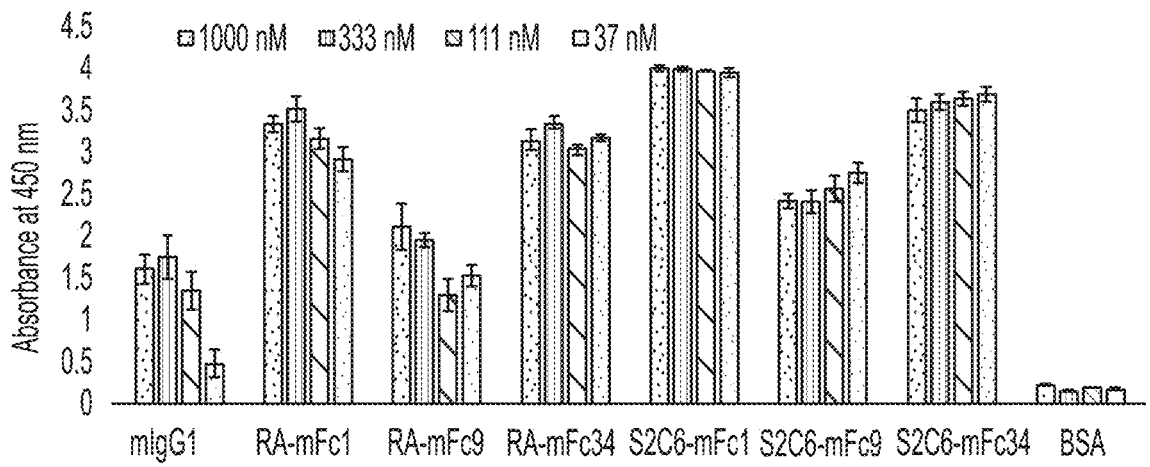
FIG. 15: ELISA results of glycosylated mouse IgG1 (mIgG1), and the three selected IgG variants mFc1, mFc9, and mFc34 to mFcγRII. The three seleted IgG variants with Rituximab-Fab or anti-mouse CD40 Fab (S2C6) were assayed with monomeric mFcγRII.

ELISA Measurements of mIgG Variants with mFcγRII:

The 1 μg of mIgG variants, RAmFc1, RAmFc9, RAmFc34, S2C6-mFc1, S2C6-mFc9, S2C6-mFc34, or mIgG1, was coated onto a 96-well EIA/RIA plate (Qiagen) at 4° C. overnight, and the plates were washed three times with PBS containing 0.05% Tween® 20 (PBST). The plates were blocked for 1 h at room temperature with 3% bovine serum albumin (BSA) in PBS and washed three times with PBST. The fifty μl of the serial diluted monomeric mFcγRII (1000 nM-37 nM) was added to the plates. After 1 h of incubation at room temperature, the plates were washed with PBST and were incubated with 50 μL of PBS containing 1:5000 goat anti-His HRP (GE Healthcare) for 1 h. After three times of washing with PBST, 50 μL TMB substrate was added per well (Thermo Scientific), 50 μL of 1 M $H_2SO_4$ was added to neutralize, and the absorbance at 450 nm was recorded. All three mFc variants showed higher binding activities than glycosylated wild type mIgG1 for mFcγRII-his. mIgG1 showed decreasing binding signals depends on the concentrations of mFcγRII, but mFc1 and mFc34 showed the saturated binding signals under same concentrations of mFcγRII. These high binding activities were observed with two different Fab (Rituximab and S2C6, anti-mCD40 Ab) (FIG. 15).

Example 16—Construction, Expression and Purification of the Streptokinase-Fc Variants All plasmids and primers are described in Tables 8 and 9. The streptokinase C (STPK) gene (Uniprot ID: P00779) and STPK-human wt Fc of IgG1 gene were synthesized by IDT. Linear pcDNA3.4 was amplified using two specific primers (STPK107 (SEQ ID NO: 26) and STPK108 (SEQ ID NO: 27)). STPK-His and STPK-human Fc of IgG1 (hFc) genes were cloned into pcDNA3.4 using a Gibson Assembly®cloning kit (NEB) according to the manufacturer's instructions (Jung et al., 2012). The four mutant Fc genes, B13 T299L Fc, B21 T299L Fc, B25 T299L Fc, and B90 T299L Fc were amplified from pcDNA3.4 plasmids using two specific primers (TH083 (SEQ ID NO: 14) and TH084 (SEQ ID NO: 15)). The linear pcDNA3.4 gene was amplified using two specific primers (PCH061 (SEQ ID NO: 28) and STPK108 (SEQ ID NO: 27)). Human Fc variants genes were cloned into pcDNA3.4 using a Gibson Assembly®cloning kit (NEB) according to the manufacturer's instructions (Jung et al., 2012). The mFc variants were amplified using two specific primers (PCH059 (SEQ ID NO: 20) and PCH50 (SEQ ID NO: 21)) and were cloned into pcDNA3.4-STPK using same methods. Newly constructed STPK or STPK-Fc fused proteins were named, STPK-his, STPK-hFc, STPK-B13, STPK-B21, STPK-B25, STPK-B90, STPK-mFc, STPK-mFc1, and STPK-mFc9. STPK-his or STPK-Fc variants-expressing plasmids were transiently transfected with an equal mass of light chain plasmid in HEK293F cells (Invitrogen). All proteins were purified with same methods of above examples. The purity of the purified antibodies was assessed by 4%-20% gradient SDS-PAGE gel (NuSep) under reducing and non-reducing conditions.

Example 17—Binding Properties of the STPK-Fc Variants to FcγRs

Affinities of STPK-Fc variants with human FcγRs were evaluated with enzyme-linked immunosorbent assay (ELISA) and surface plasmon resonance.

Figure 16A:
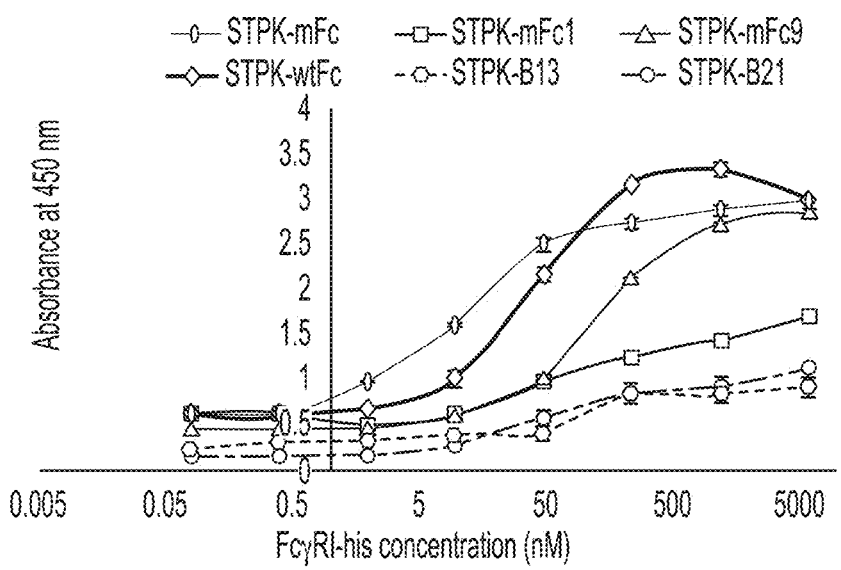
FIGS. 16A-F: ELISA results of streptokinase (STPK)-Fc variants, STPK-B13, STPK-B21, STPK-mFc1, and STPK-mFc9 to human FcγRs; monomeric FcγRI (FIG. 16A), dimeric FcγRIIA$_{H131}$ (FIG. 16B), dimeric FcγRIIA$_{R131}$ (FIG. 16C), dimeric FcγRIIB (FIG. 16D), dimeric FcγRIIIA$_{V158}$ (FIG. 16E), and dimeric FcγRIIIA$_{F158}$ (FIG. 16F).
Figure 16B:
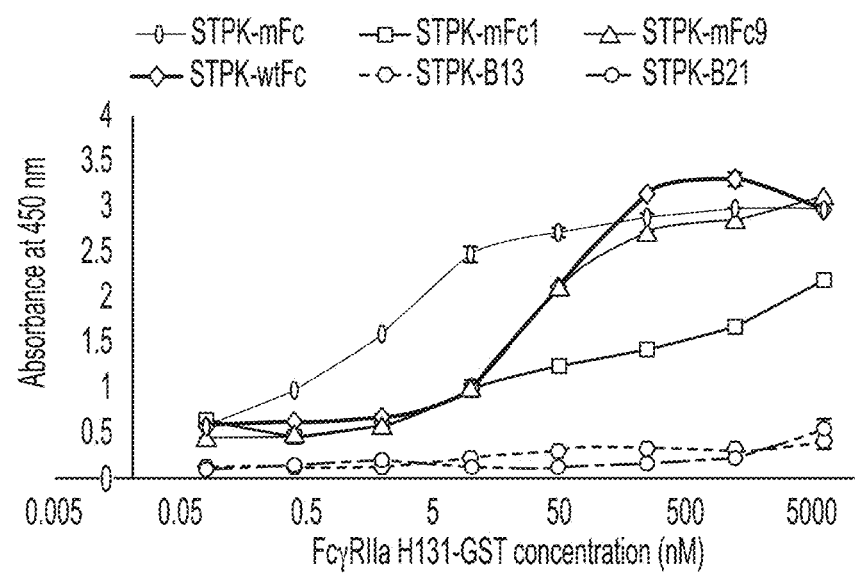
Figure 16C:
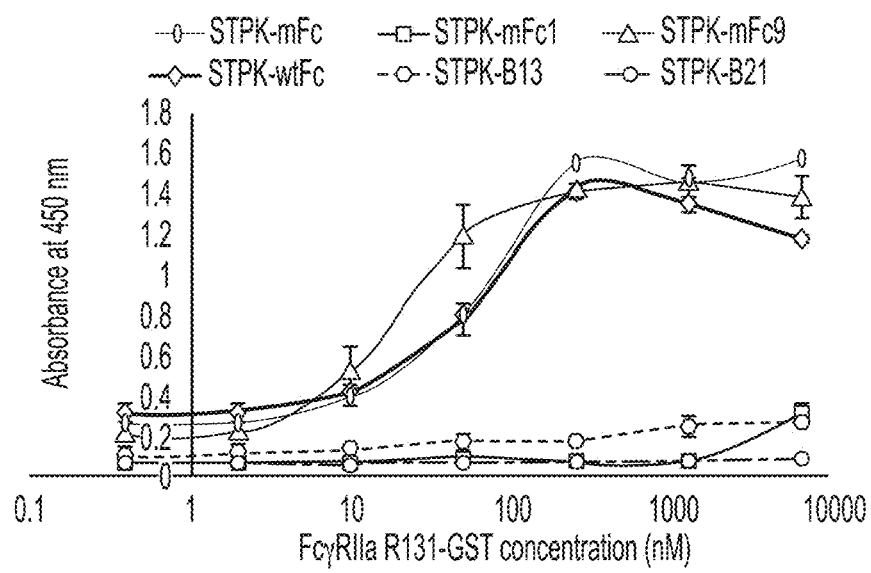
Figure 16D:
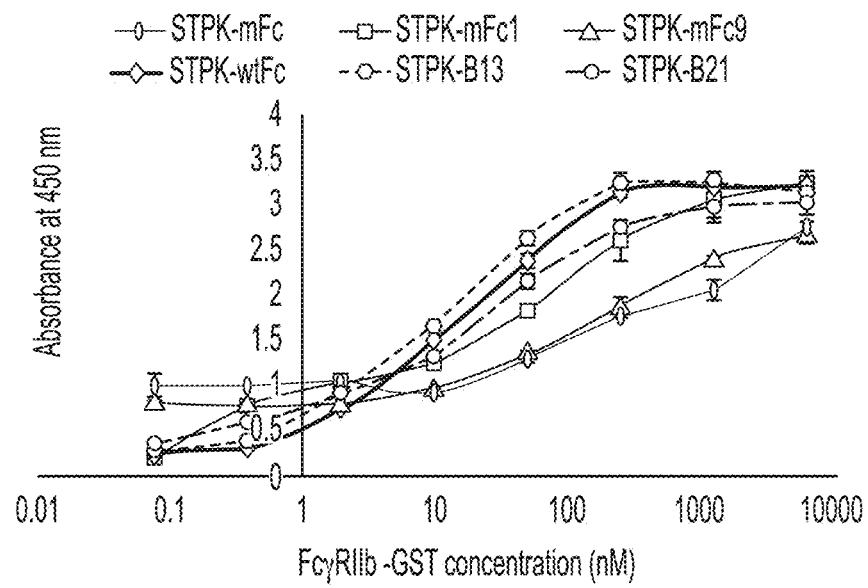
Figure 16E:
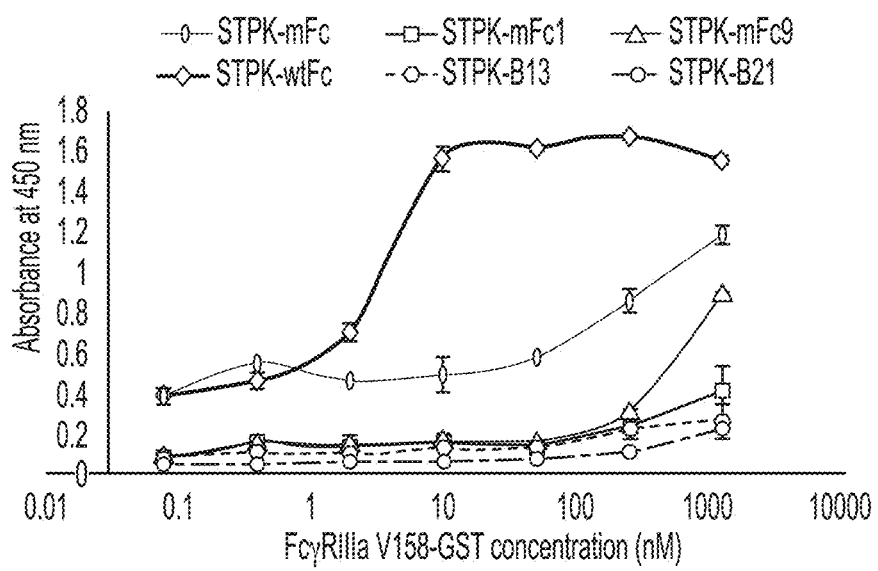
Figure 16F:
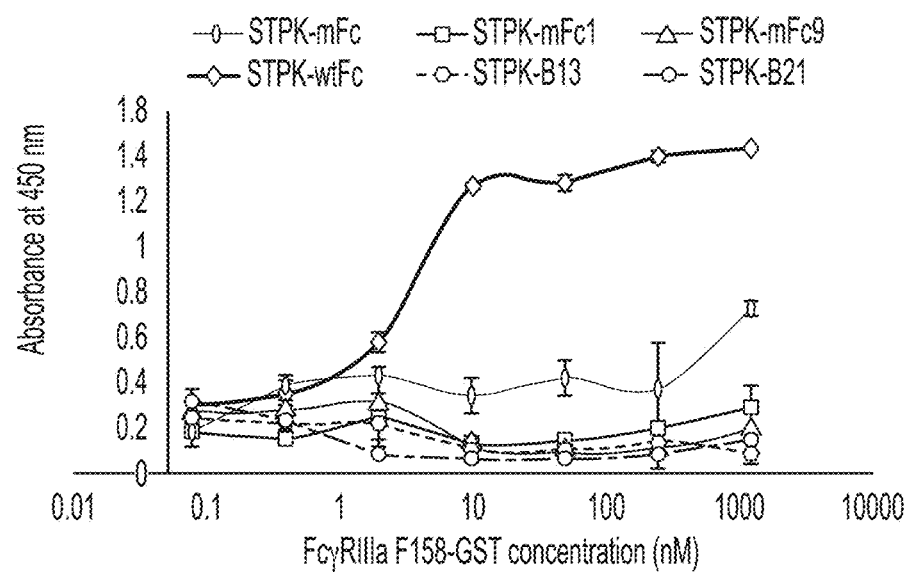
Figure 17A:
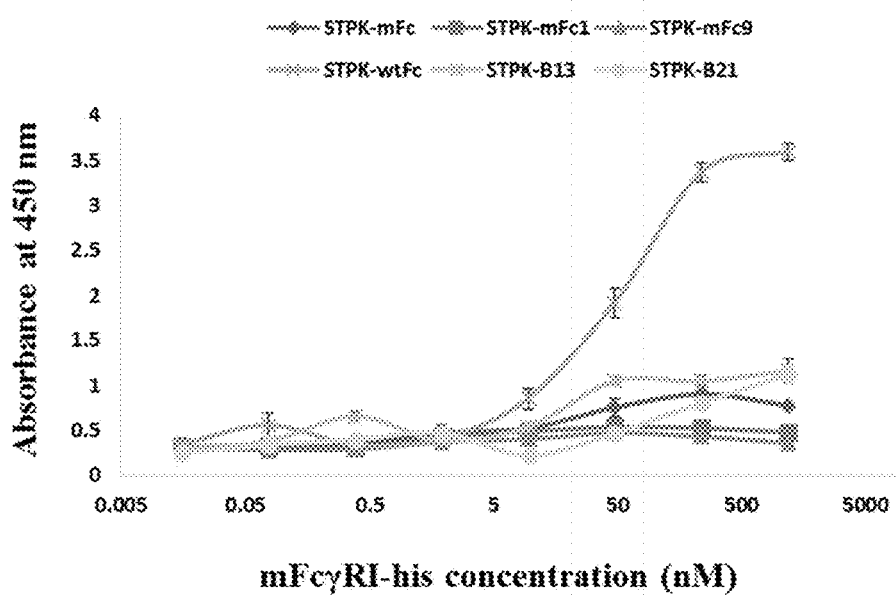
FIGS. 17A-D: ELISA results of streptokinase (STPK)-Fc variants, STPK-B13, STPK-B21, STPK-mFc1, and STPK-mFc9 to murine FcγRs; monomeric FcγRI (FIG. 17A), monomeric FcγRII (FIG. 17B), monomeric FcγRIII (FIG. 17C), and monomeric FcγRIV (FIG. 17D).
Figure 17B:
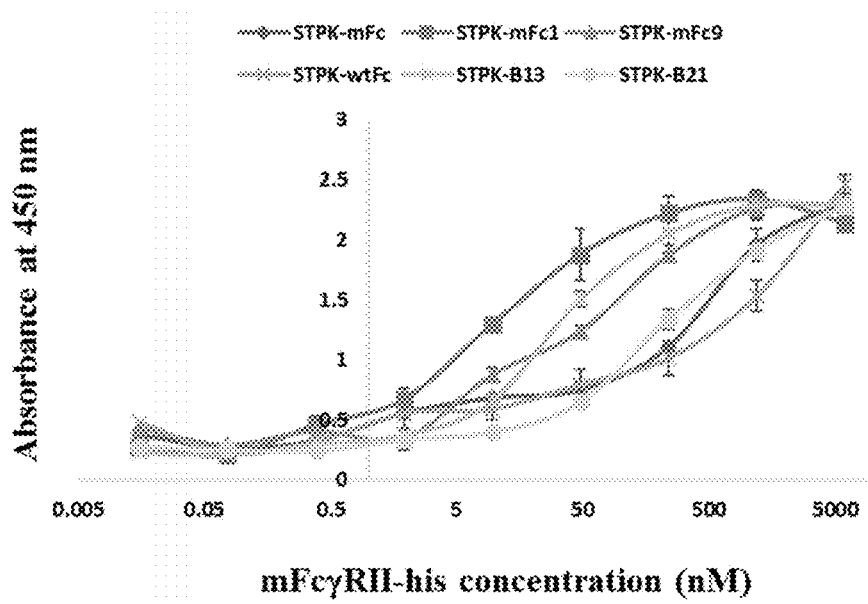
Figure 17C:
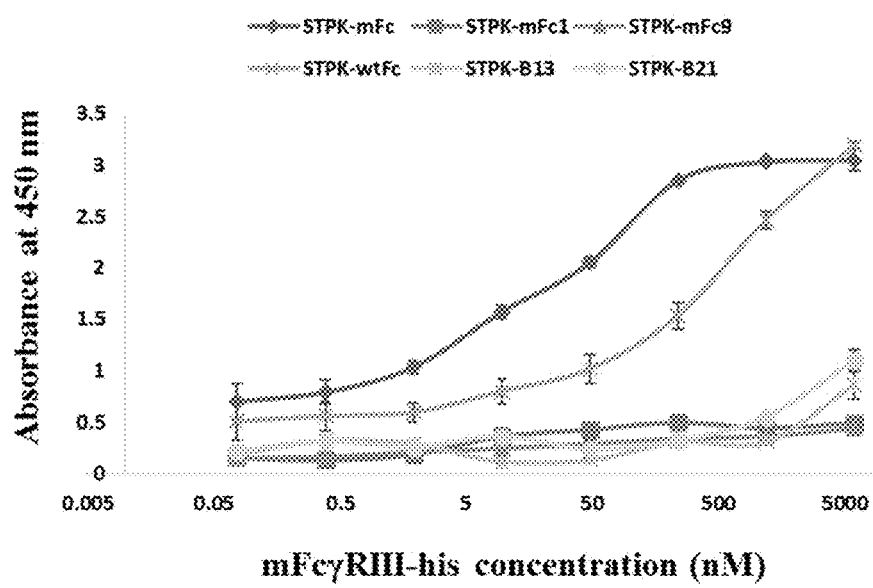
Figure 17D:
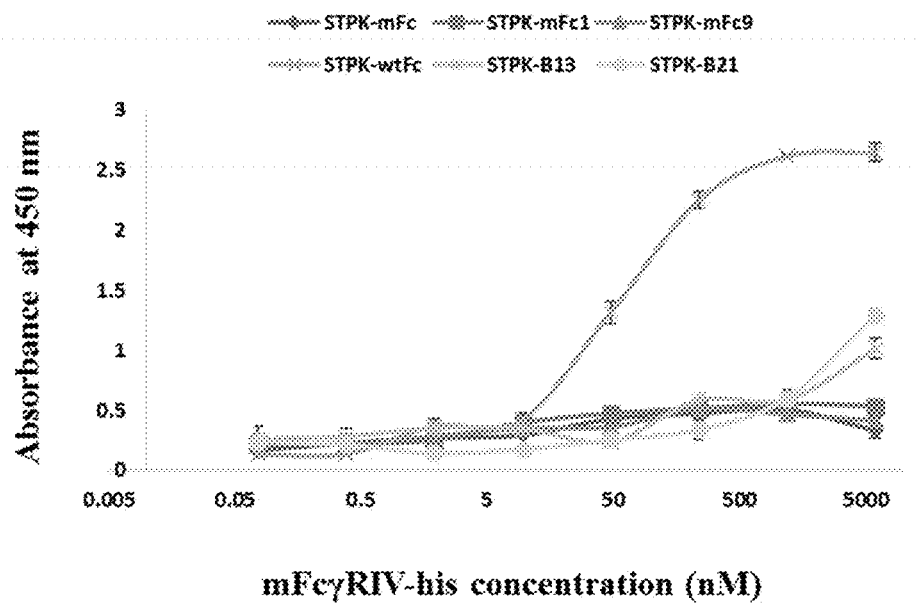

ELISA Measurements of STPK-Fc Variants with FcγRs:
The 1 μg of STPK-hFc, STPK-B13 Fc, STPK-B21 Fc, STPK-mFc, STPK-mFc1, and STPK-mFc9 was coated onto a 96-well EIA/RIA plate (Qiagen) at 4° C. overnight, and the plates were washed three times with PBS containing 0.05% Tween® 20 (PBST). The plates were blocked for 1 h at room temperature with 3% bovine serum albumin (BSA) in PBS and washed three times with PBST. The fifty μl of the serial diluted FcγRs (6000 nM-0.07 nM) was added to the plates. After 1 h of incubation at room temperature, the plates were washed with PBST and were incubated with 50 μL of PBS containing 1:5000 goat anti-His HRP or anti-GST HRP (GE Healthcare) for 1 h. After three times of washing with PBST, 50 μL TMB substrate was added per well (Thermo Scientific), 50 μL of 1 M $H_2SO_4$ was added to neutralize, and the absorbance at 450 nm was recorded. STPK-B13 Fc and STPK-B21 Fc maintained their FcγRIIb-specific binding activities of IgG format. STPK-B13 Fc and STPK-B21 Fc showed very weak binding signals for 6 μM of monomeric FcγRI (FIG. 16A), and showed only negligible binding signals for 6 μM of dimeric FcγRIIa H131 or R131 (FIGS. 16B&C), and 1.2 M of dimeric FcγRIIIa V158 or F158 (FIGS. 15E&F). However, STPK-B13 Fc showed about 7-fold enhanced $IC_{50}$ values as compared to STPK-wt Fc, and STPK-B21 Fc showed about 3.5-fold enhanced $IC_{50}$ values as compared to STPK-wt Fc (FIGS. 16A-F and Table 13). STPK-B13 Fc and STPK-B21 Fc also showed selectively high binding properties for mFcγRII (FIGS. 17A-D and Table 13). The $IC_{50}$ of STPK-B13 Fc for mFcγRII is 40±8 nM. The $IC_{50}$ of STPK-B21 Fc for mFcγRII is 210±31 nM. STPK-B13 Fc and STPK-B21 Fc showed weak binding activities for mFcγRI and mFcγRIII. For mFcγRIV, their $IC_{50}$ values are over 6000 nM (FIG. 17 and Table 13). STPK-mFc1 and STPK-mFc9 showed higher binding activity than STPK-mFc and similar binding affinity with STPK-wt Fc for human dimeric FcγRIIb (FIG. 16D). STPK-mFc1 showed more specific to human FcγRIIb than STPK-mFc9 (Table 13). STPK-mFc1 showed over 15-fold decreased binding activities as compared to STPK-mFc for FcγRI and very weak binding activities for FcγRIIa. However, STPK-mFc9 showed similar $IC_{50}$ values for FcγRIIa and FcγRIIb and also showed 3-fold lower binding activities than STPK-mFc for FcγRI (Table 13). STPK-mFc1 and STPK-mFc9 showed specific binding properties for mFcγRII (FIGS. 17A-D and Table 12). The $IC_{50}$ of STPK-mFc1 for mFcγRII is 10±1 nM, which is 37-fold enhanced affinity than STPK-mFc. The $IC_{50}$ of STPK-mFc9 for mFcγRII is 60±7 nM, which is 6-fold enhanced affinity than STPK-mFc. The STPK-mFc1 and STPK-mFc9 did not show any binding activities for other mFcγRs (FIGS. 17A-D and Table 13).

TABLE 13

$IC_{50}$ (nM) values of STPK-Fc variants with FcγRs (data correspond to FIGS. 16A-F and FIGS. 17A-D).

|  | STPK-wtFc | STPK-B13 | STPK-B21 | STPK-mFc | STPK-mFc1 | STPK-mFc9 |
| --- | --- | --- | --- | --- | --- | --- |
| FcγRI | 18 ± 1 | Weak | Weak | 45 ± 2 | >6000 | 130 ± 9 |
| FcγRIIa H131 | 38 ± 3 | — | — | 2.0 ± 0.3 | >200 | 39 ± 1 |
| FcγRIIa R131 | 47 ± 3 | — | — | 51 ± 4 | — | 24 ± 1 |

TABLE 13-continued

IC$_{50}$ (nM) values of STPK-Fc variants with FcγRs (data correspond to FIGS. 16A-F and FIGS. 17A-D).

|  | STPK-wtFc | STPK-B13 | STPK-B21 | STPK-mFc | STPK-mFc1 | STPK-mFc9 |
|---|---|---|---|---|---|---|
| FcγRIIb | 63 ± 5 | 9 ± 1 | 18 ± 2 | >100 | 42 ± 2 | 57 ± 3 |
| FcγRIIIa F158 | 7 ± 1 | — | — | >1000 | — | — |
| FcγRIIIa V158 | 4 ± 1 | — | — | >300 | — | >1000 |
| mFcγRI | 32 ± 2 | Weak | Weak | Weak | — | — |
| mFcγRII | 715 ± 65 | 40 ± 8 | 210 ± 31 | 375 ± 15 | 10 ± 1 | 60 ± 7 |
| mFcγRIII | 230 ± 14 | Weak | Weak | 9 ± 1 | — | — |
| mFcγRIV | 47 ± 3 | >6000 | >6000 | — | — | — |

Figure 18:
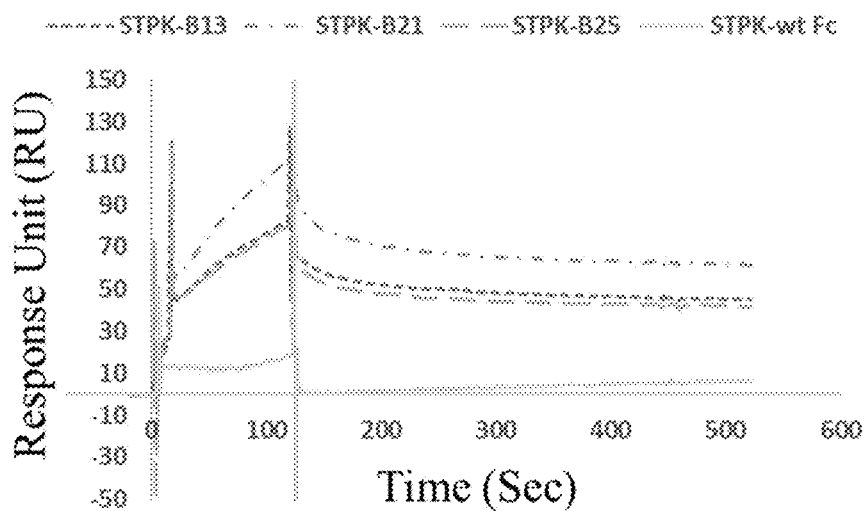
FIG. 18: The kinetic properties and surface plasmon resonance (SPR) sensorgrams of STPK-wt Fc, and the selected STPK-Fc variants STPK-B13, STPK-B21, and STPK-B25 with dimeric FcγRIIB.

SPR Measurements of STPK-Fc Variants with FcγRs:

SPR Measurements were performed on Biacore® 3000 (GE Healthcare) instrument. Bovine serum albumin (BSA) was immobilized in the reference channels of the CM5 sensor chip to subtract buffer effect and non-specific binding signal. STPK-wt Fc, STPK-B13 Fc, STPK-B21 Fc, STPK-B25 Fc, STPK-mFc, and STPK-mFc9 were immobilized on the CM5 sensor chips by amine coupling at pH 5.0. In order to compare the binding activities of STPK-human Fc variants, 600 nM of dimeric FcγRIIb was injected in the CM5 chip at 30 µL/min for 2 min. RU max of each STPK-Fc variants w83 RU for STPK-B13 Fc, 111 RU for STPK-B21 Fc, 81 RU for STPK-B25 Fc, and 19 RU for STPK-wt Fc (FIG. 18). The FcγRIIb specific STPK-Fc variants showed about 4-6 fold higher RU max by SPR analysis. The serial diluted mFcγRs-his (188 nM-6000 nM) was injected in the CM5 chip at 30 µL/min for 2 min. The chip was regenerated after each binding event with 10 mM glycine (pH3.0) with a contact time of 1 min. The resulting sensorgrams were fit with a 1:1 Lagmuir model or steady state model using Biaevaluation 3.0 software (Table 14). As a result of these experiments, STPK-mFc9 showed 3.75 fold enhanced affinity as compared to STPK-wt mFc for mFcγRII. STPK-mFc9 showed only 3.5 RU with 6 µM of mFcγRIII and K$_D$ of it is over 50 µM. For mFcγRI and mFcγRIV, STPK-mFc9 did not show any binding response.

TABLE 14

Kinetic properties and surface plasmon resonance (SPR) sensorgrams of STPK-wt mFc and STPK-mFc9 with mFcγRs

|  | STPK-mFc | | STPK-mFc9 | | | |
|---|---|---|---|---|---|---|
|  | K$_D$ (µM) | Chi$^2$ | K$_{on}$ (×10$^3$/MS) | K$_{off}$ (×10$^{-4}$/S) | K$_D$ (µM) | Chi$^2$ |
| mFcγRI | No binding | | None response | | | |
| mFcγRII | 16.1 ± 5.3 | 1.72 | 8.97 ± 0.24 | 5.39 ± 0.19 | 0.60 ± 0.04 | 1.11 |
| mFcγRIII | 14.9 ± 1.03 | 1.11 | — | — | No binding | — |
| mFcγRIV | No binding | | No binding | | | |

TABLE 8

Primers used in this study.

| SEQ ID NO: | Primer Name | Primer nucleotide sequence (5'→ 3') |
|---|---|---|
| 10 | PCH016 | GTTATTACTCGCGGCCCAGCCG |
| 11 | PCH017 | GGGGAAGAGGAAGACTGACGGN(A10% T70% G10% C10%)N(A10% T10% G10% C70%)N(A10% T10% G10% C70%)N(A10% T10% G10% C70%)N(A10% T10% G10% C70%)N(A10% T10% G10% C70%)N(A70% T10% G10% C10%)N(A10% T10% G70% C10%)N(A10% T10% G70% C10%)N(A70% T10% G10% C10%)N(A10% T10% G70% C10%)N(A10% T70% G10% C10%)N(A10% T70% G10% C10%)N(A10% T10% G10% C70%)AGGTGCTGGGCACGGTGGG |
| 12 | PCH018 | CCGTCAGTCTTCCTCTTCCCC |
| 13 | PCH021 | CGGCCGCGAATTCGGCCCC |
| 14 | TH083 | GTCGACAAGAAAGTTGAGCCCAAATCTTGCGACAAAACTCACACATGCCCACCG |
| 15 | TH084 | CTCGAGCGGCCGCTCATTTACCCGGGGACAGGGAGAGGTTTACCCGGGGACAGGGAGAGG |
| 16 | TH081 | TGAGCGGCCGCTCGAG |
| 17 | TH082 | GCAAGATTTGGGCTCAACTTTCTTGTCGAC |
| 18 | WK68 | GCCGCGGGAGGAGCAGTACAACAGCCTGTACCGTGTGG |
| 19 | WK69 | GTGAGGACGCTGACCACACGGTACAGGCTGTTGTACTGCTC |
| 20 | PCH059 | CAAACCGTGCATTTGCACCGTTCCG |
| 21 | PCH050 | TTC GGC CCC CGA GGC CCC TTT ACC CGG GCT GTG AGA CAG |

TABLE 8-continued

Primers used in this study.

| SEQ ID NO: | Primer Name | Primer nucleotide sequence (5'→ 3') |
|---|---|---|
| 22 | PCH096 | CCT TGC CGG CCT CGA GCG GCC GCT CAT TTA CCC GGG CTG TGA GAC AGA GAT TTT TC |
| 23 | PCH109 | GGT GCA AAT GCA CGG TTT GCA ACC GCA AGA TTT GGG CTC AAC TTT CTT GTC GAC |
| 24 | PCH132 | CCA CGC GAA GAA CAG TTC AAC AGC TTC TTC CGC TCT GTA AGC GAA CTG CCG |
| 25 | PCH133 | CGG CAG TTC GCT TAC AGA GCG GAA CAG GCT GTT GAA CTG TTC TTC GCG TGG |
| 26 | STPK107 | ACACTGGACACCTTTGAGCAC |
| 27 | STPK108 | ATGAGCGGCCGCTCG |
| 28 | PCH061 | GGCACGGTGGGCATGTGTGAGTTTTGTC |

TABLE 9

| Plasmids used in this study | | |
|---|---|---|
| Plasmids | Relevant characteristics | Reference or Source |
| pMopac12-pelB-IgG-VH-CH1-CH2-CH3-FLAG | Bacterial display vector containing IgGVH1-CH1-CH2 and CH3 domains of trastuzumab | Jung et al., 2012 |
| pMopac12-pelB-IgG-VH-CH1-mFc-FLAG | Bacterial display vector containing IgGVH1-CH1 domains of trastuzumab and Fc domains of mIgG1 | This study |
| pBAD30-PelB-VL-Ck-NlpA-VL-Ck-His-cMyc | Bacterial display vector containing IgGVL-Ck domains of trastuzumab | Jung et al., 2012 |
| pBAD33-NlpA-PA domain 4-His | Bacterial display vector containing PA domain 4 | Leysath al., 2009 |
| pMAZ IgH M18 | Mammalian expression vector containing M18 heavy chain | Leysath et al., 2009 |
| pMAZ IgL M18 | Mammalian expression vector containing M18 light chain | Leysath et al., 2009 |
| pMaz-IgH-FcγRI-His | FcγRI gene in pMaz-IgH for monomeric mammalian expression | Jung et al., 2012 |
| pMaz-IgH-FcγRIIA$_{H131}$-GST | FcγRIIA$_{H131}$ gene in pMaz-IgH for dimeric mammalian expression | Jung et al., 2012 |
| pMaz-IgH-FcγRIIA$_{R131}$-GST | FcγRIIA$_{R131}$ gene in pMaz-IgH for dimeric mammalian expression | Jung et al., 2012 |
| pMaz-IgH-FcγRIIB-GST | FcγRIIB gene in pMaz-IgH for dimeric mammalian expression | Jung et al., 2012 |
| pMaz-IgH-FcγRIIIA$_{V158}$-GST | FcγRIIIA$_{V158}$ gene in pMaz-IgH for dimeric mammalian expression | Jung et al., 2012 |
| pMaz-IgH-FcγRIIIA$_{F158}$-GST | FcγRIIIA$_{F158}$ gene in pMaz-IgH for dimeric mammalian expression | Jung et al., 2012 |
| pcDNA3.4-FcγRIIA$_{H131}$-His | FcγRIIA$_{H131}$ gene in pcDNA3.4 for monimeric mammalian expression | Kelton et al., 2015 |
| pcDNA3.4-FcγRIIA$_{R131}$-His | FcγRIIA$_{R131}$ gene in pcDNA3.4 for monimeric mammalian expression | Kelton et al., 2015 |
| pcDNA3.4-FcγRIIB-His | FcγRIIB gene in pcDNA3.4 for monimeric mammalian expression | Kelton et al., 2015 |
| pcDNA3.4-FcγRIIIA$_{V158}$-His | FcγRIIIA$_{V158}$ gene in pcDNA3.4 for monimeric mammalian expression | Kelton et al., 2015 |
| pcDNA3.4-FcγRIIIA$_{F158}$-His | FcγRIIIA$_{F158}$ gene in pcDNA3.4 for monimeric mammalian expression | Kelton et al., 2015 |
| pcDNA3.4-mFcγRI-His | Mouse FcγRI gene in pcDNA3.4 for monimeric mammalian expression | This study |
| pcDNA3.4-mFcγRII-His | Mouse FcγRII gene in pcDNA3.4 for monimeric mammalian expression | This study |
| pcDNA3.4-mFcγRIII-His | Mouse FcγRIII gene in pcDNA3.4 for monimeric mammalian expression | This study |
| pcDNA3.4-mFcγRIV-His | Mouse FcγRIV gene in pcDNA3.4 for monimeric mammalian expression | This study |
| pcDNA3.4-IgH-Rituximab | Mammalian expression vector containing Rituximab heavy chain | This study |
| pcDNA3.4-IgL-Rituximab | Mammalian expression vector containing Rituximab light chain | This study |
| pcDNA3.4-IgH-Rituximab V12 | Mammalian expression vector containing Rituximab V12 heavy chain | This study |
| pcDNA3.4-IgH-Rituximab B13 | Mammalian expression vector containing Rituximab B13 heavy chain | This study |
| pcDNA3.4-IgH-Rituximab B15 | Mammalian expression vector containing Rituximab B15 heavy chain | This study |

TABLE 9-continued

Plasmids used in this study

| Plasmids | Relevant characteristics | Reference or Source |
|---|---|---|
| pcDNA3.4-IgH-Rituximab B19 | Mammalian expression vector containing Rituximab B19 heavy chain | This study |
| pcDNA3.4-IgH-Rituximab B21 | Mammalian expression vector containing Rituximab B21 heavy chain | This study |
| pcDNA3.4-IgH-Rituximab B25 | Mammalian expression vector containing Rituximab B25 heavy chain | This study |
| pcDNA3.4-IgH-Rituximab B29 | Mammalian expression vector containing Rituximab B29 heavy chain | This study |
| pcDNA3.4-IgH-Rituximab B41 | Mammalian expression vector containing Rituximab B41 heavy chain | This study |
| pcDNA3.4-IgH-Rituximab B90 | Mammalian expression vector containing Rituximab B90 heavy chain | This study |
| pcDNA3.4-IgH-ABn2 | Mammalian expression vector containing Abn2 heavy chain | This study |
| pcDNA3.4-IgH-ABn15 | Mammalian expression vector containing Abn15 heavy chain | This study |
| pcDNA3.4-IgH-ABn17 | Mammalian expression vector containing Abn17 heavy chain | This study |
| pcDNA3.4-IgH-RA-wt mFc | Mammalian expression vector containing Rituximab-wt mFc heavy chain | This study |
| pcDNA3.4-IgH-RAmFc1 | Mammalian expression vector containing Rituximab-mFc1 heavy chain | This study |
| pcDNA3.4-IgH-RAmFc9 | Mammalian expression vector containing Rituximab-mFc9 heavy chain | This study |
| pcDNA3.4-IgH-RAmFc34 | Mammalian expression vector containing Rituximab-mFc34 heavy chain | This study |
| pcDNA3.4-IgH-S2C6-wt mFc | Mammalian expression vector containing S2C6-wt mFc heavy chain | This study |
| pcDNA3.4-IgH-S2C6-mFc1 | Mammalian expression vector containing S2C6-mFc1 heavy chain | This study |
| pcDNA3.4-IgH-S2C6-mFc9 | Mammalian expression vector containing S2C6-mFc9 heavy chain | This study |
| pcDNA3.4-IgH-S2C6-mFc34 | Mammalian expression vector containing S2C6-mFc34 heavy chain | This study |
| pcDNA3.4-STPK - his | Mammalian expression vector containing 6x his-tagged streptokinase | This study |
| pcDNA3.4-STPK - hFc | Mammalian expression vector containing hFc of IgG1 fused streptokinase | This study |
| pcDNA3.4-STPK - B13 T299L Fc | Mammalian expression vector containing B13 T299L Fc fused streptokinase | This study |
| pcDNA3.4-STPK - B21 T299L Fc | Mammalian expression vector containing B21 T299L Fc fused streptokinase | This study |
| pcDNA3.4-STPK - B25 T299L Fc | Mammalian expression vector containing B25 T299L Fc fused streptokinase | This study |
| pcDNA3.4-STPK - B90 T299L Fc | Mammalian expression vector containing B90 T299L Fc fused streptokinase | This study |
| pcDNA3.4-STPK - mFc | Mammalian expression vector containing mFc of mIgG1 fused streptokinase | This study |
| pcDNA3.4-STPK - mFc1 T299L | Mammalian expression vector containing mFc1 T299L fused streptokinase | This study |
| pcDNA3.4-STPK - mFc9 T299L | Mammalian expression vector containing mFc9 T299L fused streptokinase | This study |

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Pat. No. 3,817,837
U.S. Pat. No. 3,826,364
U.S. Pat. No. 3,850,752
U.S. Pat. No. 3,939,350
U.S. Pat. No. 3,996,345
U.S. Pat. No. 4,275,149
U.S. Pat. No. 4,277,437
U.S. Pat. No. 4,284,412
U.S. Pat. No. 4,366,241
U.S. Pat. No. 4,472,509
U.S. Pat. No. 4,498,766
U.S. Pat. No. 4,661,913

U.S. Pat. No. 4,683,195
U.S. Pat. No. 4,683,202
U.S. Pat. No. 4,714,682
U.S. Pat. No. 4,767,206
U.S. Pat. No. 4,774,189
U.S. Pat. No. 4,800,159
U.S. Pat. No. 4,857,451
U.S. Pat. No. 4,870,287
U.S. Pat. No. 4,883,750
U.S. Pat. No. 4,938,948
U.S. Pat. No. 4,988,618
U.S. Pat. No. 4,989,977
U.S. Pat. No. 5,021,236
U.S. Pat. No. 5,160,974
U.S. Pat. No. 5,302,523
U.S. Pat. No. 5,322,783
U.S. Pat. No. 5,384,253
U.S. Pat. No. 5,464,765
U.S. Pat. No. 5,478,722
U.S. Pat. No. 5,538,877
U.S. Pat. No. 5,538,880
U.S. Pat. No. 5,550,318
U.S. Pat. No. 5,563,055
U.S. Pat. No. 5,567,326
U.S. Pat. No. 5,580,859
U.S. Pat. No. 5,589,466
U.S. Pat. No. 5,610,042
U.S. Pat. No. 5,656,610
U.S. Pat. No. 5,702,932
U.S. Pat. No. 5,736,524
U.S. Pat. No. 5,739,169
U.S. Pat. No. 5,760,395
U.S. Pat. No. 5,779,907
U.S. Pat. No. 5,780,448
U.S. Pat. No. 5,789,215
U.S. Pat. No. 5,801,005
U.S. Pat. No. 5,824,311
U.S. Pat. No. 5,824,520
U.S. Pat. No. 5,830,880
U.S. Pat. No. 5,843,650
U.S. Pat. No. 5,846,709
U.S. Pat. No. 5,846,783
U.S. Pat. No. 5,846,945
U.S. Pat. No. 5,849,497
U.S. Pat. No. 5,849,546
U.S. Pat. No. 5,849,547
U.S. Pat. No. 5,858,652
U.S. Pat. No. 5,866,366
U.S. Pat. No. 5,882,864
U.S. Pat. No. 5,889,155
U.S. Pat. No. 5,912,148
U.S. Pat. No. 5,916,776
U.S. Pat. No. 5,916,779
U.S. Pat. No. 5,922,574
U.S. Pat. No. 5,928,905
U.S. Pat. No. 5,928,906
U.S. Pat. No. 5,932,451
U.S. Pat. No. 5,935,825
U.S. Pat. No. 5,939,291
U.S. Pat. No. 5,942,391
U.S. Pat. No. 5,945,100
U.S. Pat. No. 5,981,274
U.S. Pat. No. 5,994,624
U.S. Pat. No. 7,094,571
U.S. Pat. No. 7,666,422
U.S. Pat. No. 7,109,304
U.S. Pat. No. 8,465,743

U.S. Patent Publ. 2003/0180937
U.S. Patent Publ. 2003/0219870
U.S. Patent Publ. 2005/0260736
U.S. Patent Publ. 2006/0173170
U.S. Patent Publ. 2008/0292646
U.S. Patent Publ. 2009/0304666
Abbondanzo et al., *Breast Cancer Res. Treat.*, 16:182(151), 1990.
Ahmed et al., *Clinical Cancer Research*, 16(2):474-485, 2010.
Ahouse et al., *J. Immunol.*, 151:6076-6088, 1993.
Allen and Seed, *Nucleic Acids Res.*, 16:11824, 1988.
Andersen et al., *Eur. J. Immunol.*, 36:3044-3051, 2006.
Antibodies: A Laboratory Manual, Cold Spring Harbor Laboratory, 1988
Atherton et al., *Biol. Reprod.*, 32(1):155-171, 1985.
Austin-Ward and Villaseca, *Revista Medica de Chile*, 126(7):838-845, 1998.
Ausubel et al., *In: Current Protocols in Molecular Biology*, John, Wiley & Sons, Inc, N Y, 1994.
Baneyx and Mujacic, *Nat. Biotechnol.*, 22:1399-1408, 2004.
Barrington, R. A. et al., *J. Exp. Med.* 196, 1189-1199, 2002.
Bellus, *J. Macromol. Sci. Pure Appl. Chem.*, A31(1): 1355-1376, 1994.
Bemrntzen et al., *J. Immunol. Methods*, 298:93-104, 2005.
Better et al., *Science*, 240: 1041-10433, 1988.
Bocek and Pecht, *FEBS Lett.*, 331, 86-90, 1993.
Boeke et al., *Mol. Gen. Genet.*, 186, 1982.
Bolland and Ravetch, *Adv. Immunol.*, 72:149-177, 1999.
Borrok et al., *ACS Chem. Biol.*, 7:1596-1602, 2012.
Boruchov et al., *J. Clin. Invest.*, 115:2914-2923, 2005.
Boss et al., *Nucleic Acids Res.*, 12:3791-3806, 1984.
Bowden and Georgiou, *J. Biol. Chem.*, 265:16760-16766, 1990.
Bukau et al., *J. Bacteriol.*, 163:61, 1985.
Bukowski et al., *Clinical Cancer Res.*, 4(10):2337-2347, 1998.
Burman et al., *J. Bacteriol.*, 112:1364, 1972.
Burton and Burton, *Nat. Rev. Immunol.*, 4:89-99, 2004.
Cabilly et al., *Proc. Natl. Acad. Sci. USA*, 81:3273-3277, 1984.
Carbonelli et al., *FEMS Microbiol Lett.*, 177:75-82. 1999
Chames et al., *Proc. Natl. Acad. Sci. USA*, 97:7969-7974, 2000.
Chen and Guillemin, *Int J Tryptophan Res*, 2:1-19, 2009.
Chen and Okayama, *Mol. Cell Biol.*, 7(8):2745-2752, 1987.
Christodoulides et al., *Microbiology*, 144(Pt 11):3027-3037, 1998.
Cocea, *Biotechniques*, 23(5):814-816, 1997.
Collins et al., *Immunogenetics*, 45:440-443, 1997.
Curran et al., *Proceedings of the National Academy of Sciences*, 107:4275-4280, 2010.
Daeron, *Annu. Rev. Immunol.*, 15:203-234, 1997.
Dall'Acqua et al., *J. Immunol.*, 177:1129-1138, 2006.
Daugherty et al., *Protein Eng.*, 12:613 621, 1999.
Davidson et al., *J. Immunother.*, 21(5):389-398, 1998.
De Jager et al., *Semin. Nucl. Med.*, 23(2): 165-179, 1993.
de Jong et al., *Int J Gynecol Cancer*, 21(7):1320-1327, 2011.
de Kruif and Logtenberg, *J. Biol. Chem.*, 271:7630-7634, 1996.
Decad and Nikaido, *J. Bacteriol.*, 128:325, 1976.
Della Chiesa et al., *Blood*, 108(13):4118-4125, 2006.
Desai et al., *Cancer Res.*, 58:2417-2425, 1998.
Dholakia et al., *J. Biol. Chem.*, 264(34):20638-20642, 1989.
Diebolder et al., *Science*, 343:1260-1263, 2014.
Doolittle and Ben-Zeev, *Methods Mol Biol*, 109:215-237, 1999.

Edelman et al., *Proc Natl Acad Sci USA*, 63:78-85, 1969.
Eigenbrot et al., *J. Molec. Biol.*, 229:969-995, 1993.
Elbein et al., *Glycobiology*, 13:17R-27, 2003.
Elvin et al., *Int. J. Pharm.*, 440:83-98, 2013.
European Appln. 320 308
European Appln. 329 822
Fahnestock et al., *J. Bacteriol.*, 167:870-880, 1986.
Farmer et al., *FEMS Microbiol. Lett.*, 176:11, 1999.
Fechheimer, et al., *Proc Natl. Acad. Sci. USA*, 84:8463-8467, 1987.
Fraley et al., *Proc. Natl. Acad. Sci. USA*, 76:3348-3352, 1979.
Francisco et al., *Proc. Natl. Acad. Sci. USA*, 90:10444-10448, 1993.
Frohman, In: *PCR Protocols: A Guide To Methods And Applications*, Academic Press, N.Y., 1990.
Fromant et al., *Anal. Biochem.*, 224:347-353, 1995.
Gaboriaud et al., *J. Biol. Chem.*, 278:46974-46982, 2003.
Garinot-Schneider et al., *J. Mol. Biol.*, 260:731-742, 1996.
GB Appln. 2 202 328
Georgiou and Segatori, *Current Opin. Biotech.*, 16:538-545, 2005.
Ghetie and Ward, *Annu. Rev. Immunol.*, 18:739-766, 2000.
Godin-Ethier et al., *Clinical Cancer Research*, 17(22):6985-6991, 2011.
Golay et al., *Blood*, 95:3900-3908, 2000.
Gomi et al., *J. Immunol.*, 144:4046-4052, 1990.
Gopal, *Mol. Cell Biol.*, 5:1188-1190, 1985.
Graham and Van Der Eb, *Virology*, 52:456-467, 1973.
Griffiths and Duncan, *Curr Opin. Biotechnol.*, 9:102-108, 1998.
Guddat et al., *Proc. Natl. Acad. Sci. USA*, 90:4271-4275, 1993.
Gulbis and Galand, *Hum. Pathol.*, 24(12):1271-1285, 1993.
Guzman et al., *J. Bacteriol.*, 177:4121-4130, 1995.
Halloran et al., *J. Immunol.*, 153:2631-2641, 1994.
Hanibuchi et al., *Int. J. Cancer*, 78(4):480-485, 1998.
Harkki et al., *BioTechnology*, 7:596-603, 1989.
Harland and Weintraub, *J. Cell Biol.*, 101(3):1094-1099, 1985.
Harvey et al., *J. Immunol. Methods*. 308:43-52, 2006.
Harvey et al., *Proc. Natl. Acad. Sci. USA*, 101:9193-9198, 2004.
Hayhurst et al., *J. Immunol. Methods*, 276:185-196, 2003.
Hellstrand et al., *Acta Oncologica*, 37(4):347-353, 1998.
Hobot et al., *J. Bacteriol.*, 160:143, 1984.
Hollander, *Front. Immun.*, 3:3, 2012.
Holmgaard et al., *The Journal of Experimental Medicine*, 210:1389-1402, 2013.
Hoogenboom and Winter, *J. Mol. Biol.*, 227:381-388, 1992.
Hoogenboom et al., *Immunotechnology*, 4:1-20, 1998.
Hoover and Lubkowski, *Nucl. Acids Res.*, 30:e43, 2002.
Hopwood et al., In: Genetic Manipulation of *Streptomyces, A Laboratory Manual*, The John Innes Foundation, Norwich, Conn., 1985.
Horton et al., *J. Immunol.*, 186(7):4223-4233, 2011.
Hughes-Jones and Gardner, *Mol. Immunol.*, 16:697-701, 1979.
Hui and Hashimoto, *Infection Immun.*, 66(11):5329-5336, 1998.
Idusogie et al., *J. Immunol.*, 166:2571-2575, 2001.
Innis et al., *Proc. Natl. Acad. Sci. USA*, 85(24):9436-9440, 1988.
Irvin et al., *J. Bacteriol.*, 145:1397, 1981.
Ito et al., *J. Biochem.*, 79:1263, 1976.
Janeway et al., *Immunobiology: The Immune System in Health and Disease.* 6th Edition. New York: Garland Publishing, 2005.
Jefferis, *Adv. Exp. Med. Biol.*, 564:143-148, 2005.
Jefferis, *Biotechnol. Prog.*, 21:11-16, 2005.
Jeong and Lee, *Appl. Environ. Microbiol.*, 69:1295-1298, 2003.
Jouenne and Junter, *FEMS Microbiol. Lett.*, 56:313, 1990.
Jung et al., *ACS Chem. Biol.*, 8:368-375, 2012.
Jung et al., *Biotechnol Bioeng*, 98:39-47, 2007
Jung et al., *Proc. Natl. Acad. Sci. USA*, 107:604-609, 2010.
Jung et al., *Protein Expr. Purif.*, 31:240-246, 2003.
Kabat et al., In: *Sequences of Proteins of Immunological Interest*, U. S. Dept. of Health and Hum. Serv., Bethesda, 1991.
Kaeppler et al., *Plant Cell Reports*, 9:415-418, 1990.
Kalergis and Ravetch, *J. Exp. Med.*, 195:1653-1659, 2002.
Kaneda et al., *Science*, 243:375-378, 1989.
Kaper et al., *PLoS Biology*, 5(10):e257, 2007.
Kato et al, *J. Biol. Chem.*, 266:3361-3364, 1991.
Kawarasaki et al., *Nucleic Acids Res.*, 31:e126, 2003.
Kelton et al., *Chemistry & Biology*, 21(12): 1603-1609, 2014.
Khatoon et al., *Ann. Neurol*, 26(2):210-215, 1989.
Kim et al., *Eur. J. Immunol.*, 24:2429-2434, 1994.
King et al., *J. Biol. Chem.*, 264(17):10210-10218, 1989.
Kipriyanov and Little, *Mol. Biotechnol.*, 12:173-201, 1999.
Kjaer et al., *FEBS Lett.*, 431:448-452, 1998.
Knight et al., *Mol. Immunol.*, 32:1271-1281, 1995.
Kohler and Milstein, *Nature*, 256:495-497, 1975.
Kouzarides and Ziff, *Nature*, 336:646-6451, 1988.
Kuroda et al., *Lancet.*, 357:1225-1240, 2001.
Kwoh et al., *Proc. Natl. Acad. Sci. USA*, 86:1173, 1989.
Labischinski et al., *J. Bacteriol.*, 162:9, 1985.
Landschulz et al., *Science*, 240:1759-1764, 1988.
Lanio and Jeltsch, *Biotechniques*, 25:962-955, 1998.
Lazar et al., *Proc. Natl. Acad. Sci. USA*, 103:4005-4010, 2006.
Lei et al., *J. Bacteriol.*, 169:4379-4383, 1987.
Levenson et al., *Hum. Gene Ther.*, 9(8):1233-1236, 1998.
Leysath et al., *J. Mol. Biol.*, 387:680-693, 2009.
Li et al., *J. Mol. Biol.*, 337:743-759, 2004.
Lipowska-Bhalla et al., *Cancer Immunology Immunotherapy*, 61(7):953-962, 2012.
Lob et al., *Nat Rev Cancer*, 9(6):445-452, 2009.
Lordanescu, *J. Bacteriol*, 12:597 601, 1975.
Mandi and Vecsei, *J Neural Transm*, 119(2):197-209, 2012.
Maniatis, et al., Molecular Cloning, A Laboratory Manual, Cold Spring Harbor Press, Cold Spring Harbor, N.Y., 1988.
Marciano et al., *Science*, 284:1516, 1999.
Masaki et al., *Nucleic Acids Res.*, 13:1623-1635, 1985.
Mazor et al., *Nat. Biotech.*, 25(5):563-565, 2007.
Mellor et al., *Gene*, 24:1-14, 1983.
Mezrich et al., *The Journal of Immunology*, 185(6):3190-3198, 2010.
Michaelsen et al., *Scand. J. Immunol.*, 70:553-564, 2009.
Moore et al., *mAbs*, 2:181-189, 2010.
Munson and Pollard, *Anal. Biochem.*, 107:220, 1980.
Nagaoka and Akaike, *Protein Engineering*, 16: 243-245, 2003.
Natsume et al., *Cancer Res.*, 68:3863-3872, 2008.
Nicolau and Sene, *Biochim. Biophys. Acta*, 721:185-190, 1982.
Nicolau et al., *Methods Enzymol.*, 149:157-176, 1987.
Nikaido and Nakae, *Adv. Microb. Physiol.*, 20:163, 1979.
Nikaido and Vaara, *Microbiol. Rev.*, 49:1, 1985.

Nikaido, *J. Bacteriology*, 178(20):5853-5859, 1996.
Nimmerjahn F. and Ravetch J V, *Science*. 310(5753):1510-1512, 2005.
O'Brien et al., *Protein Expr. Purif*, 24:43-50, 2002.
Ober et al., *J. Immunol.*, 172:2021-2029, 2004b.
Ober et al., *Proc. Natl. Acad. Sci. USA*, 101:11076-11081, 2004a.
Olsson et al., *Eur. J. Biochem.*, 168:319-324, 1987.
Opitz et al., *Nature*, 478(7368): 197-203, 2011.
Opitz et al., *PLoS One*, 6(5):e19823, 2011.
Orlandi et al., *Proc. Natl. Acad. Sci. USA*, 86:3833-3837, 1989.
Osborn et al., *J. Biol. Chem*, 247:3973-3986, 1972.
Owens and Haley, *Biochem. Biophys. Res. Commun.*, 142(3):964-971, 1987.
Painbeni et al., *Proc Natl. Acad. Sci. USA*, 94:6712, 1997.
Pavlou and Belsey, *Eur. J. Pharm. Biopharm.*, 59:389-396, 2005.
PCT Appln. PCT/US87/00880
PCT Appln. PCT/US89/01025
PCT Appln. WO 2012/031744
PCT Appln. WO 2012/079000
PCT Appln. WO 2013/059593
PCT Appln. WO 88/10315
PCT Appln. WO 89/06700
PCT Appln. WO 90/07641
PCT Appln. WO 93/06213
PCT Appln. WO 94/09699
PCT Appln. WO 95/06128
Penttila et al., *Gene*, 61:155-164, 1987.
Phillips, N. E. & Parker, D. C. *J. Immunol.* 132, 627-632, 1984.
Pilotte et al., *Proc Natl Acad Sci USA*, 109(7):2497-2502, 2012.
Potrykus et al., *Mol. Gen. Genet.*, 199(2):169-177, 1985.
Potter and Haley, *Methods Enzymol*, 91:613-633, 1983.
Prendergast, *Nature*, 478(7368): 192-194, 2011.
Purvis et al., *Appl. Environ. Microbiol.*, 71:3761-3769, 2005.
Qin et al., *Proc. Natl. Acad. Sci. USA*, 95(24):14411-14416, 1998.
Qin, D. et al. *J. Immunol.* 164, 6268-6275, 2000.
Raghavan and Bjorkman, *Annu. Rev. Cell Dev. Biol.*, 12:181-220, 1996.
Ramsland et al., *J. Immunol.*, 187:3208-3217, 2011.
Rankin et al., *Blood* 108: 2384-2391, 2006.
Rao and Torriani, *J. Bacteriol.*, 170, 5216, 1988.
Ravetch and Perussia et al., *J. Exp. Med.*, 170:481-497, 1989.
Ravetch et al., *Science*, 234:718-725, 1986.
Remington's Pharmaceutical Sciences, 18th Ed. Mack Printing Company, 1289-1329, 1990.
Rippe, et al., *Mol. Cell Biol.*, 10:689-695, 1990.
Rodewald, *J. Cell Biol.*, 71:666-669, 1976.
Ruhlmann et al., *FEBS Lett.*, 235:262-266, 1988.
Rutella et al., *Endocr Metab Immune Disord Drug Targets*, 9(2): 151-177, 2009.
Sambrook et al., In: *Molecular cloning: a laboratory manual*, 2d Ed., Cold Spring Harbor Laboratory Press, Cold Spring Harbor, N.Y., 1989.
Sazinsky et al., *Proc. Natl. Acad. Sci. USA*, 105:20167-20172, 2008.
Schellenberger et al., *Nature Biotech.*, 27:1186-1190, 2009.
Schierle et al., *J. Bacteriol.*, 185:5706-5713, 2003.
Schneider and Zacharias, *Mol. Immunol.*, 51:66-72, 2012.
Sears et al., *J. Immunol.*, 144:371-378, 1990.
Sergina and Moasser, *Trends in Molec. Med.*, 13:527-534, 2007.
Shields et al., *J. Biol. Chem.*, 276:6591-6604, 2001.
Shin et al., *Proc Natl Acad Sci USA*, 110(30): 12391-12396, 2013.
Shuttleworth et al., *Gene*, 58(2-3):283-295, 1987.
Sibakov et al., *Eur. J. Biochem.*, 145:567 572, 1984.
Sidman, C. L. and Unanue, E. R. *J. Exp. Med.* 144, 882-896, 1976.
Simister and Mostov, *Nature*, 337(6203):184-187, 1989.
Sinclair, N. R. *J. Exp. Med.* 129, 1183-1201, 1969.
Sledge and Bing, *J. Biol. Chem.*, 248:2818-2823, 1973.
Sondermann et al., *J. Mol. Biol.*, 309:737-749, 2001.
Song et al., *International Immunopharmacology*, 11(8):932-938, 2011.
Stenberg et al., *Mol. Microbiol.*, 6:1185-1194, 1992.
Stengelin et al., *Embo J*, 7:1053-1059, 1988.
Stone et al., *ACS Chemical Biology*, 5:333-342, 2010.
Stuart et al., *Embo J.*, 8:3657-3666, 1989.
Stuart et al., *J. Exp. Med.*, 166:1668-1684, 1987.
Tominaga et al., *Biochem. Biophys. Res. Commun.*, 168:683-689, 1990.
Uhlen et al., *J. Biol. Chem.*, 259:1695-702, 1984.
Van Wielink and Duine, *Trends Biochem Sci.*, 15:136, 1990.
Wada et al., *J. Biol. Chem.*, 274:17353-17357, 1999.
Walker et al., *Nucleic Acids Res.*, 20(7):1691-1696, 1992.
Walport, Complement. First of two parts. *N. Engl. J. Med.*, 344:1058-1066, 2001.
Walport, Complement. Second of two parts. *N. Engl. J. Med.*, 344:1140-1144, 2001.
Ward, Proc, Embo-Alko Workshop on Molecular Biology of Filamentous Fungi, Helsinki, 119-128, 1989.
Wawrzynczak and Thorpe, In: Immunoconjugates, Antibody Conuugates In Radioimaging And Therapy Of Cancer, Vogel (Ed.), NY, Oxford University Press, 28, 1987.
Wilson et al., *Cancer Cell*, 19(1):101-113, 2011
Wong et al., *Gene*, 10:87-94, 1980.
Wright and Morrison, *Trends Biotechnol.*, 15:26-32, 1997.
Yao et al., *Mol Biosyst*, 7(9):2608-2614, 2011.
Yoshikawa et al., *Eur J Haematol*, 84(4):304-309, 2010.
Zeger et al., *Proc. Natl. Acad. Sci. USA*, 87:3425-3429, 1990.
Zhang et al., *Immunogenetics*, 39:423-437, 1994.
Zhang et al., *Microbiology*, 144(Pt 4):985-991, 1998.
Zohair et al., *Biochem. J.*, 257:865-873, 1989.

What is claimed is:

1. A polypeptide comprising an aglycosylated mutant or variant human IgG Fc domain capable of binding human FcγRIIb; and
at least one of:
(i) substitution mutations of arginine at position 234 (L234R), glutamic acid at position 235 (L235E), glutamic acid at position 236 (G236E), arginine at position 238 (P238R), and glutamine at position 351 (L351Q);
(ii) substitution mutations of glutamine at position 246 (K246Q), alanine at position 260 (T260A); glutamine at position (L351Q), arginine at position 386 (Q386R); phenylalanine at position 396 (P396F), and methionine at position 397 (V397M); or
(iii) substitution mutations of alanine at amino acid 264 (V264A), serine at amino acid 328 (L328S), cysteine at amino acid 329 (P329C), tryptophan at amino acid 330 (A330W), asparagine at amino acid 332 (I332N), glycine at position 333 (E333G), and valine at amino acid position 336 (I336V); or
(iv) substitution mutations of valine at amino acid 233 (E233V), phenylalanine at amino acid 234 (L234F), proline at amino acid 236 (G236P), valine at amino acid 237 (G237V), alanine at position 348 (V348A), and arginine at position 362 (Q362R);
wherein the mutations are in Kabat numbering.

2. The polypeptide of claim 1, wherein the Fc domain has substitution mutations of arginine at position 234 (L234R), glutamic acid at position 235 (L235E), glutamic acid at position 236 (G236E), arginine at position 238 (P238R), and glutamine at position 351 (L351Q).

3. The polypeptide of claim 2, wherein the Fc domain comprises or consists of the sequence of B21 or SEQ ID NO: 7.

4. The polypeptide of claim 1, wherein the Fc domain has substitution mutations of glutamine at position 246 (K246Q), alanine at position 260 (T260A); glutamine at position (L351Q), arginine at position 386 (Q386R); phenylalanine at position 396 (P396F), and methionine at position 397 (V397M).

5. The polypeptide of claim 4, wherein the Fc domain comprises or consists of the sequence of Bn2 or SEQ ID NO:9.

6. The polypeptide of claim 1, wherein the Fc domain has substitution mutations of alanine at amino acid 264 (V264A), serine at amino acid 328 (L328S), cysteine at amino acid 329 (P329C), tryptophan at amino acid 330 (A330W), asparagine at amino acid 332 (I332N), glycine at position 333 (E333G), and valine at amino acid position 336 (I336V).

7. The polypeptide of claim 6, wherein the Fc domain comprises or consists of the sequence of B13 or SEQ ID NO: 6.

8. The polypeptide of claim 1, wherein the Fc domain does not selectively or detectably bind to a human FcγRI, FcγRIIa H131, FcγRIIa R131, FcγRIIIa F158, and/or FcγRIIIa V158 polypeptide.

9. The polypeptide of claim 8, wherein the Fc domain does not selectively or detectably bind to a human FcγRI.

10. The polypeptide of claim 8, wherein the Fc domain does not detectably bind to human FcγRIIa H131, FcγRIIa R131, FcγRIIIa F158, and FcγRIIIa V158.

11. The polypeptide of claim 1, wherein the Fc domain binds FcγRIIB with an equilibrium constant of less than 1 μM and does not display detectable binding to FcγRI, FcγRIIa H131, FcγRIIa R131, FcγRIIIa F158, and FcγRIIIa V158.

12. The polypeptide of claim 1, wherein the Fc domain further comprises a substitution mutation at amino acid 299.

13. The polypeptide of claim 12, wherein the Fc domain comprises a leucine at amino acid position 299 (T299L).

14. The polypeptide of claim 1, further comprising a non-Fc receptor (non-FcR) binding domain.

15. The polypeptide of claim 14, wherein the non-FcR binding domain is an Ig variable domain.

16. The polypeptide of claim 15, wherein the polypeptide is a full-length antibody.

17. The polypeptide of claim 16, wherein the antibody is an agonistic antibody.

18. The polypeptide of claim 16, wherein the antibody selectively binds CD20, CD40, IL-10, or 4-1BB.

19. The polypeptide of claim 1, wherein the antibody is chemically conjugated to or covalently bound to a toxin.

20. The polypeptide of claim 14, wherein the non-FcR binding region is not an antigen binding site of an antibody.

21. The polypeptide of claim 14, wherein the non-FcR binding region binds a cell-surface protein.

22. The polypeptide of claim 14, wherein the non-FcR binding regions binds a soluble protein.

23. A pharmaceutical formulation comprising a polypeptide of claim 1 in a pharmaceutically acceptable carrier.

* * * * *

SEQUENCE LISTING

<160> NUMBER OF SEQ ID NOS: 29

<210> SEQ ID NO 1
<211> LENGTH: 222
<212> TYPE: PRT
<213> ORGANISM: Homo sapiens

<400> SEQUENCE: 1

```
Cys Pro Pro Cys Pro Ala Pro Glu Leu Leu Gly Gly Pro Ser Val Phe
1               5                   10                  15

Leu Phe Pro Pro Lys Pro Lys Asp Thr Leu Met Ile Ser Arg Thr Pro
            20                  25                  30

Glu Val Thr Cys Val Val Val Asp Val Ser His Glu Asp Pro Glu Val
            35                  40                  45

Lys Phe Asn Trp Tyr Val Asp Gly Val Glu Val His Asn Ala Lys Thr
        50                  55                  60

Lys Pro Arg Glu Glu Gln Tyr Asn Ser Thr Tyr Arg Val Val Ser Val
65                  70                  75                  80

Leu Thr Val Leu His Gln Asp Trp Leu Asn Gly Lys Glu Tyr Lys Cys
                85                  90                  95

Lys Val Ser Asn Lys Ala Leu Pro Ala Pro Ile Glu Lys Thr Ile Ser
                100                 105                 110

Lys Ala Lys Gly Gln Pro Arg Glu Pro Gln Val Tyr Thr Leu Pro Pro
            115                 120                 125

Ser Arg Asp Glu Leu Thr Lys Asn Gln Val Ser Leu Thr Cys Leu Val
        130                 135                 140

Lys Gly Phe Tyr Pro Ser Asp Ile Ala Val Glu Trp Glu Ser Asn Gly
145                 150                 155                 160

Gln Pro Glu Asn Asn Tyr Lys Thr Thr Pro Pro Val Leu Asp Ser Asp
                165                 170                 175

Gly Ser Phe Phe Leu Tyr Ser Lys Leu Thr Val Asp Lys Ser Arg Trp
            180                 185                 190

Gln Gln Gly Asn Val Phe Ser Cys Ser Val Met His Glu Ala Leu His
        195                 200                 205

Asn His Tyr Thr Gln Lys Ser Leu Ser Leu Ser Pro Gly Lys
    210                 215                 220

<210> SEQ ID NO 2
<211> LENGTH: 222
<212> TYPE: PRT
<213> ORGANISM: Artificial Sequence
<220> FEATURE:
<223> OTHER INFORMATION: Synthetic peptide

<400> SEQUENCE: 2

Cys Pro Pro Cys Pro Ala Pro Glu Leu Leu Gly Gly Pro Ser Val Phe
1               5                   10                  15

Leu Phe Pro Pro Lys Pro Lys Asp Thr Leu Met Ile Ser Arg Thr Pro
            20                  25                  30

Glu Val Thr Cys Val Val Val Ala Asp Val Ser His Glu Asp Pro Glu Val
            35                  40                  45

Lys Phe Asn Trp Tyr Val Asp Gly Val Glu Val His Asn Ala Lys Thr
        50                  55                  60

Lys Pro Arg Glu Glu Gln Tyr Asn Ser Leu Tyr Arg Val Val Ser Val
65                  70                  75                  80

Leu Thr Val Leu His Gln Asp Trp Leu Asn Gly Lys Glu Tyr Lys Cys
                85                  90                  95

Lys Val Ser Asn Lys Ala Ser Cys Trp Pro Asn Gly Lys Thr Val Ser
                100                 105                 110

Lys Ala Lys Gly Gln Pro Arg Glu Pro Gln Val Tyr Thr Leu Pro Pro
            115                 120                 125

Ser Arg Asp Glu Leu Thr Lys Asn Gln Val Ser Leu Thr Cys Leu Val
        130                 135                 140
```

```
Lys Gly Phe Tyr Pro Ser Asp Ile Ala Val Glu Trp Glu Ser Asn Gly
145                 150                 155                 160

Gln Pro Glu Asn Asn Tyr Lys Thr Thr Pro Pro Val Leu Asp Ser Asp
                165                 170                 175

Gly Ser Phe Phe Leu Tyr Ser Lys Leu Thr Val Asp Lys Ser Arg Trp
            180                 185                 190

Arg Gln Gly Asn Val Phe Ser Cys Ser Val Met His Glu Ala Leu His
        195                 200                 205

Asn His Tyr Thr Gln Lys Ser Leu Ser Leu Ser Pro Gly Lys
    210                 215                 220
```

<210> SEQ ID NO 3
<211> LENGTH: 222
<212> TYPE: PRT
<213> ORGANISM: Artificial Sequence
<220> FEATURE:
<223> OTHER INFORMATION: Synthetic peptide

<400> SEQUENCE: 3

```
Cys Pro Pro Cys Pro Ala Pro Glu Arg Glu Glu Gly Arg Ser Val Phe
1               5                   10                  15

Leu Phe Pro Pro Lys Pro Lys Asp Thr Leu Met Ile Ser Arg Thr Pro
            20                  25                  30

Glu Val Thr Cys Val Val Val Asp Val Ser His Glu Asp Pro Glu Val
        35                  40                  45

Lys Phe Asn Trp Tyr Val Asp Gly Val Glu Val His Asn Ala Lys Thr
    50                  55                  60

Lys Pro Arg Glu Glu Gln Tyr Asn Ser Leu Tyr Arg Val Val Ser Val
65                  70                  75                  80

Leu Thr Val Leu His Gln Asp Trp Leu Asn Gly Lys Glu Tyr Lys Cys
                85                  90                  95

Lys Val Ser Asn Lys Ala Leu Pro Ala Pro Ile Glu Lys Thr Ile Ser
            100                 105                 110

Lys Ala Lys Gly Gln Pro Arg Glu Pro Gln Val Tyr Thr Gln Pro Pro
        115                 120                 125

Ser Arg Asp Glu Leu Thr Lys Asn Gln Val Ser Leu Thr Cys Leu Val
    130                 135                 140

Lys Gly Phe Tyr Pro Ser Asp Ile Ala Val Glu Trp Glu Ser Asn Gly
145                 150                 155                 160

Gln Pro Glu Asn Asn Tyr Lys Thr Thr Pro Pro Val Leu Asp Ser Asp
                165                 170                 175

Gly Ser Phe Phe Leu Tyr Ser Lys Leu Thr Val Asp Lys Ser Arg Trp
            180                 185                 190

Gln Gln Gly Asn Val Phe Ser Cys Ser Val Met His Glu Ala Leu His
        195                 200                 205

Asn His Tyr Thr Gln Lys Ser Leu Ser Leu Ser Pro Gly Lys
    210                 215                 220
```

<210> SEQ ID NO 4
<211> LENGTH: 222
<212> TYPE: PRT
<213> ORGANISM: Artificial Sequence
<220> FEATURE:
<223> OTHER INFORMATION: Synthetic peptide

<400> SEQUENCE: 4

```
Cys Pro Pro Cys Pro Ala Pro Glu Leu Leu Gly Gly Pro Ser Val Phe
```

```
              1               5                  10                 15
            Leu Phe Pro Pro Lys Pro Lys Asp Thr Leu Met Ile Ser Arg Thr Pro
                            20                 25                 30
            Glu Val Thr Cys Val Val Val Asp Val Ser His Glu Asp Pro Glu Val
                        35                 40                 45
            Lys Phe Asn Trp Tyr Val Asp Gly Val Glu Val His Asn Ala Lys Thr
             50                 55                 60
            Lys Pro Arg Glu Glu Gln Tyr Asn Ser Leu Tyr Arg Val Val Ser Val
             65                 70                 75                 80
            Leu Thr Val Leu His Lys Asp Trp Leu Asn Gly Lys Glu Tyr Lys Cys
                            85                 90                 95
            Lys Val Ser Asn Lys Ala Leu Pro Ala Pro Ile Glu Lys Thr Ile Ser
                           100                105                110
            Lys Ala Lys Gly Gln Pro Arg Glu Pro Gln Val Tyr Thr Leu Pro Pro
                           115                120                125
            Ser Arg Asp Glu Leu Thr Lys Asn Gln Val Ser Leu Thr Cys Leu Val
            130                135                140
            Lys Gly Phe Tyr Pro Ser Asp Ile Ala Val Glu Trp Glu Ser Asn Gly
            145                150                155                160
            Gln Pro Glu Asn Asn Tyr Lys Thr Thr Pro Pro Val Leu Asp Ser Asp
                           165                170                175
            Gly Ser Phe Phe Leu Tyr Ser Lys Leu Thr Val Asp Lys Ser Arg Trp
                           180                185                190
            Gln Gln Gly Asn Val Phe Ser Cys Ser Val Met His Glu Ala Leu His
                           195                200                205
            Asn His Tyr Thr Gln Lys Ser Leu Ser Leu Ser Pro Gly Lys
                           210                215                220

<210> SEQ ID NO 5
<211> LENGTH: 222
<212> TYPE: PRT
<213> ORGANISM: Artificial Sequence
<220> FEATURE:
<223> OTHER INFORMATION: Synthetic peptide

<400> SEQUENCE: 5

Cys Pro Pro Cys Pro Ala Pro Glu Leu Leu Gly Gly Pro Ser Val Phe
             1               5                  10                 15
            Leu Phe Pro Pro Gln Pro Lys Asp Thr Leu Met Ile Ser Arg Thr Pro
                            20                 25                 30
            Glu Val Ala Cys Val Val Val Asp Val Ser His Glu Asp Pro Glu Val
                        35                 40                 45
            Lys Phe Asn Trp Tyr Val Asp Gly Val Glu Val His Asn Ala Lys Thr
             50                 55                 60
            Lys Pro Arg Glu Glu Gln Tyr Asn Ser Leu Tyr Arg Val Val Ser Val
             65                 70                 75                 80
            Leu Thr Val Leu His Gln Asp Trp Leu Asn Gly Lys Glu Tyr Lys Cys
                            85                 90                 95
            Lys Val Ser Asn Lys Ala Leu Pro Ala Pro Ile Glu Lys Thr Ile Ser
                           100                105                110
            Lys Ala Lys Gly Gln Pro Arg Glu Pro Gln Val Tyr Thr Gln Pro Pro
                           115                120                125
            Ser Arg Asp Glu Leu Thr Lys Asn Gln Val Ser Leu Thr Cys Leu Val
            130                135                140
            Lys Gly Phe Tyr Pro Ser Asp Ile Ala Val Glu Trp Glu Ser Asn Gly
```

```
            145                 150                 155                 160
Arg Pro Glu Asn Asn Tyr Lys Thr Thr Pro Phe Met Leu Asp Ser Asp
                165                 170                 175

Gly Ser Phe Phe Leu Tyr Ser Lys Leu Thr Val Asp Lys Ser Arg Trp
                180                 185                 190

Gln Gln Gly Asn Val Phe Ser Cys Ser Val Met His Glu Ala Leu His
                195                 200                 205

Asn His Tyr Thr Gln Lys Ser Leu Ser Leu Ser Pro Gly Lys
                210                 215                 220

<210> SEQ ID NO 6
<211> LENGTH: 222
<212> TYPE: PRT
<213> ORGANISM: Artificial Sequence
<220> FEATURE:
<223> OTHER INFORMATION: Synthetic peptide

<400> SEQUENCE: 6

Cys Pro Pro Cys Pro Ala Pro Glu Leu Leu Gly Gly Pro Ser Val Phe
1               5                   10                  15

Leu Phe Pro Pro Lys Pro Lys Asp Thr Leu Met Ile Ser Arg Thr Pro
                20                  25                  30

Glu Val Thr Cys Val Val Ala Asp Val Ser His Glu Asp Pro Glu Val
                35                  40                  45

Lys Phe Asn Trp Tyr Val Asp Gly Val Glu Val His Asn Ala Lys Thr
                50                  55                  60

Lys Pro Arg Glu Glu Gln Tyr Asn Ser Thr Tyr Arg Val Val Ser Val
65                  70                  75                  80

Leu Thr Val Leu His Gln Asp Trp Leu Asn Gly Lys Glu Tyr Lys Cys
                85                  90                  95

Lys Val Ser Asn Lys Ala Ser Cys Trp Pro Asn Gly Lys Thr Val Ser
                100                 105                 110

Lys Ala Lys Gly Gln Pro Arg Glu Pro Gln Val Tyr Thr Leu Pro Pro
                115                 120                 125

Ser Arg Asp Glu Leu Thr Lys Asn Gln Val Ser Leu Thr Cys Leu Val
                130                 135                 140

Lys Gly Phe Tyr Pro Ser Asp Ile Ala Val Glu Trp Glu Ser Asn Gly
145                 150                 155                 160

Gln Pro Glu Asn Asn Tyr Lys Thr Thr Pro Pro Val Leu Asp Ser Asp
                165                 170                 175

Gly Ser Phe Phe Leu Tyr Ser Lys Leu Thr Val Asp Lys Ser Arg Trp
                180                 185                 190

Arg Gln Gly Asn Val Phe Ser Cys Ser Val Met His Glu Ala Leu His
                195                 200                 205

Asn His Tyr Thr Gln Lys Ser Leu Ser Leu Ser Pro Gly Lys
                210                 215                 220

<210> SEQ ID NO 7
<211> LENGTH: 222
<212> TYPE: PRT
<213> ORGANISM: Artificial Sequence
<220> FEATURE:
<223> OTHER INFORMATION: Synthetic peptide

<400> SEQUENCE: 7

Cys Pro Pro Cys Pro Ala Pro Glu Arg Glu Gly Arg Ser Val Phe
1               5                   10                  15
```

```
Leu Phe Pro Pro Lys Pro Lys Asp Thr Leu Met Ile Ser Arg Thr Pro
             20                   25                  30

Glu Val Thr Cys Val Val Val Asp Val Ser His Glu Asp Pro Glu Val
             35                  40                  45

Lys Phe Asn Trp Tyr Val Asp Gly Val Glu Val His Asn Ala Lys Thr
 50                      55                  60

Lys Pro Arg Glu Glu Gln Tyr Asn Ser Thr Tyr Arg Val Val Ser Val
 65                  70                  75                  80

Leu Thr Val Leu His Gln Asp Trp Leu Asn Gly Lys Glu Tyr Lys Cys
                 85                  90                  95

Lys Val Ser Asn Lys Ala Leu Pro Ala Pro Ile Glu Lys Thr Ile Ser
                100                 105                 110

Lys Ala Lys Gly Gln Pro Arg Glu Pro Gln Val Tyr Thr Gln Pro Pro
            115                 120                 125

Ser Arg Asp Glu Leu Thr Lys Asn Gln Val Ser Leu Thr Cys Leu Val
        130                 135                 140

Lys Gly Phe Tyr Pro Ser Asp Ile Ala Val Glu Trp Glu Ser Asn Gly
145                 150                 155                 160

Gln Pro Glu Asn Asn Tyr Lys Thr Thr Pro Pro Val Leu Asp Ser Asp
                165                 170                 175

Gly Ser Phe Phe Leu Tyr Ser Lys Leu Thr Val Asp Lys Ser Arg Trp
            180                 185                 190

Gln Gln Gly Asn Val Phe Ser Cys Ser Val Met His Glu Ala Leu His
        195                 200                 205

Asn His Tyr Thr Gln Lys Ser Leu Ser Leu Ser Pro Gly Lys
    210                 215                 220

<210> SEQ ID NO 8
<211> LENGTH: 222
<212> TYPE: PRT
<213> ORGANISM: Artificial Sequence
<220> FEATURE:
<223> OTHER INFORMATION: Synthetic peptide

<400> SEQUENCE: 8

Cys Pro Pro Cys Pro Ala Pro Glu Leu Leu Gly Gly Pro Ser Val Phe
 1               5                  10                  15

Leu Phe Pro Pro Lys Pro Lys Asp Thr Leu Met Ile Ser Arg Thr Pro
             20                   25                  30

Glu Val Thr Cys Val Val Val Asp Val Ser His Glu Asp Pro Glu Val
             35                  40                  45

Lys Phe Asn Trp Tyr Val Asp Gly Val Glu Val His Asn Ala Lys Thr
 50                      55                  60

Lys Pro Arg Glu Glu Gln Tyr Asn Ser Thr Tyr Arg Val Val Ser Val
 65                  70                  75                  80

Leu Thr Val Leu His Lys Asp Trp Leu Asn Gly Lys Glu Tyr Lys Cys
                 85                  90                  95

Lys Val Ser Asn Lys Ala Leu Pro Ala Pro Ile Glu Lys Thr Ile Ser
                100                 105                 110

Lys Ala Lys Gly Gln Pro Arg Glu Pro Gln Val Tyr Thr Leu Pro Pro
            115                 120                 125

Ser Arg Asp Glu Leu Thr Lys Asn Gln Val Ser Leu Thr Cys Leu Val
        130                 135                 140

Lys Gly Phe Tyr Pro Ser Asp Ile Ala Val Glu Trp Glu Ser Asn Gly
145                 150                 155                 160
```

Gln Pro Glu Asn Asn Tyr Lys Thr Thr Pro Val Leu Asp Ser Asp
            165                 170                 175

Gly Ser Phe Phe Leu Tyr Ser Lys Leu Thr Val Asp Lys Ser Arg Trp
        180                 185                 190

Gln Gln Gly Asn Val Phe Ser Cys Ser Val Met His Glu Ala Leu His
    195                 200                 205

Asn His Tyr Thr Gln Lys Ser Leu Ser Leu Ser Pro Gly Lys
210                 215                 220

<210> SEQ ID NO 9
<211> LENGTH: 222
<212> TYPE: PRT
<213> ORGANISM: Artificial Sequence
<220> FEATURE:
<223> OTHER INFORMATION: Synthetic peptide

<400> SEQUENCE: 9

Cys Pro Pro Cys Pro Ala Pro Glu Leu Leu Gly Gly Pro Ser Val Phe
1               5                   10                  15

Leu Phe Pro Pro Gln Pro Lys Asp Thr Leu Met Ile Ser Arg Thr Pro
            20                  25                  30

Glu Val Ala Cys Val Val Val Asp Val Ser His Glu Asp Pro Glu Val
        35                  40                  45

Lys Phe Asn Trp Tyr Val Asp Gly Val Glu Val His Asn Ala Lys Thr
    50                  55                  60

Lys Pro Arg Glu Glu Gln Tyr Asn Ser Thr Tyr Arg Val Val Ser Val
65                  70                  75                  80

Leu Thr Val Leu His Gln Asp Trp Leu Asn Gly Lys Glu Tyr Lys Cys
                85                  90                  95

Lys Val Ser Asn Lys Ala Leu Pro Ala Pro Ile Glu Lys Thr Ile Ser
            100                 105                 110

Lys Ala Lys Gly Gln Pro Arg Glu Pro Gln Val Tyr Thr Gln Pro Pro
        115                 120                 125

Ser Arg Asp Glu Leu Thr Lys Asn Gln Val Ser Leu Thr Cys Leu Val
    130                 135                 140

Lys Gly Phe Tyr Pro Ser Asp Ile Ala Val Glu Trp Glu Ser Asn Gly
145                 150                 155                 160

Arg Pro Glu Asn Asn Tyr Lys Thr Thr Pro Phe Met Leu Asp Ser Asp
                165                 170                 175

Gly Ser Phe Phe Leu Tyr Ser Lys Leu Thr Val Asp Lys Ser Arg Trp
            180                 185                 190

Gln Gln Gly Asn Val Phe Ser Cys Ser Val Met His Glu Ala Leu His
        195                 200                 205

Asn His Tyr Thr Gln Lys Ser Leu Ser Leu Ser Pro Gly Lys
    210                 215                 220

<210> SEQ ID NO 10
<211> LENGTH: 22
<212> TYPE: DNA
<213> ORGANISM: Artificial sequence
<220> FEATURE:
<223> OTHER INFORMATION: Synthetic primer

<400> SEQUENCE: 10
gttattactc gcggcccagc cg                                          22

<210> SEQ ID NO 11
<211> LENGTH: 55

-continued

```
<212> TYPE: DNA
<213> ORGANISM: Artificial sequence
<220> FEATURE:
<223> OTHER INFORMATION: Synthetic primer
<220> FEATURE:
<221> NAME/KEY: misc_feature
<222> LOCATION: (22)..(36)
<223> OTHER INFORMATION: n is a, c, g, or t

<400> SEQUENCE: 11
ggggaagagg aagactgacg gnnnnnnnnn nnnnnnaggt gctgggcacg gtggg          55

<210> SEQ ID NO 12
<211> LENGTH: 21
<212> TYPE: DNA
<213> ORGANISM: Artificial sequence
<220> FEATURE:
<223> OTHER INFORMATION: Synthetic primer

<400> SEQUENCE: 12
ccgtcagtct tcctcttccc c                                               21

<210> SEQ ID NO 13
<211> LENGTH: 19
<212> TYPE: DNA
<213> ORGANISM: Artificial sequence
<220> FEATURE:
<223> OTHER INFORMATION: Synthetic primer

<400> SEQUENCE: 13
cggccgcgaa ttcggcccc                                                  19

<210> SEQ ID NO 14
<211> LENGTH: 54
<212> TYPE: DNA
<213> ORGANISM: Artificial sequence
<220> FEATURE:
<223> OTHER INFORMATION: Synthetic primer

<400> SEQUENCE: 14
gtcgacaaga aagttgagcc caaatcttgc gacaaaactc acacatgccc accg           54

<210> SEQ ID NO 15
<211> LENGTH: 60
<212> TYPE: DNA
<213> ORGANISM: Artificial sequence
<220> FEATURE:
<223> OTHER INFORMATION: Synthetic primer

<400> SEQUENCE: 15
ctcgagcggc cgctcattta cccggggaca gggagaggtt tacccgggga cagggagagg     60

<210> SEQ ID NO 16
<211> LENGTH: 16
<212> TYPE: DNA
<213> ORGANISM: Artificial sequence
<220> FEATURE:
<223> OTHER INFORMATION: Synthetic primer

<400> SEQUENCE: 16
tgagcggccg ctcgag                                                     16

<210> SEQ ID NO 17
<211> LENGTH: 30
<212> TYPE: DNA
<213> ORGANISM: Artificial sequence
<220> FEATURE:
```

<223> OTHER INFORMATION: Synthetic primer

<400> SEQUENCE: 17
gcaagatttg ggctcaactt tcttgtcgac                                      30

<210> SEQ ID NO 18
<211> LENGTH: 38
<212> TYPE: DNA
<213> ORGANISM: Artificial sequence
<220> FEATURE:
<223> OTHER INFORMATION: Synthetic primer

<400> SEQUENCE: 18
gccgcgggag gagcagtaca acagcctgta ccgtgtgg                             38

<210> SEQ ID NO 19
<211> LENGTH: 41
<212> TYPE: DNA
<213> ORGANISM: Artificial sequence
<220> FEATURE:
<223> OTHER INFORMATION: Synthetic primer

<400> SEQUENCE: 19
gtgaggacgc tgaccacacg gtacaggctg ttgtactgct c                         41

<210> SEQ ID NO 20
<211> LENGTH: 25
<212> TYPE: DNA
<213> ORGANISM: Artificial sequence
<220> FEATURE:
<223> OTHER INFORMATION: Synthetic primer

<400> SEQUENCE: 20
caaaccgtgc atttgcaccg ttccg                                           25

<210> SEQ ID NO 21
<211> LENGTH: 39
<212> TYPE: DNA
<213> ORGANISM: Artificial sequence
<220> FEATURE:
<223> OTHER INFORMATION: Synthetic primer

<400> SEQUENCE: 21 ttcggcccccc gaggcccctt tacccgggct gtgagacag                           39

<210> SEQ ID NO 22
<211> LENGTH: 56
<212> TYPE: DNA
<213> ORGANISM: Artificial sequence
<220> FEATURE:
<223> OTHER INFORMATION: Synthetic primer

<400> SEQUENCE: 22
ccttgccggc ctcgagcggc cgctcattta cccgggctgt gagacagaga tttttc         56

<210> SEQ ID NO 23
<211> LENGTH: 54
<212> TYPE: DNA
<213> ORGANISM: Artificial sequence
<220> FEATURE:
<223> OTHER INFORMATION: Synthetic primer

<400> SEQUENCE: 23
ggtgcaaatg cacggtttgc aaccgcaaga tttgggctca actttcttgt cgac           54

```
<210> SEQ ID NO 24
<211> LENGTH: 51
<212> TYPE: DNA
<213> ORGANISM: Artificial sequence
<220> FEATURE:
<223> OTHER INFORMATION: Synthetic primer

<400> SEQUENCE: 24
ccacgcgaag aacagttcaa cagcctgttc cgctctgtaa gcgaactgcc g         51

<210> SEQ ID NO 25
<211> LENGTH: 51
<212> TYPE: DNA
<213> ORGANISM: Artificial sequence
<220> FEATURE:
<223> OTHER INFORMATION: Synthetic primer

<400> SEQUENCE: 25
cggcagttcg cttacagagc ggaacaggct gttgaactgt tcttcgcgtg g         51

<210> SEQ ID NO 26
<211> LENGTH: 21
<212> TYPE: DNA
<213> ORGANISM: Artificial sequence
<220> FEATURE:
<223> OTHER INFORMATION: Synthetic primer

<400> SEQUENCE: 26
acactggaca cctttgagca c                                           21

<210> SEQ ID NO 27
<211> LENGTH: 15
<212> TYPE: DNA
<213> ORGANISM: Artificial sequence
<220> FEATURE:
<223> OTHER INFORMATION: Synthetic primer

<400> SEQUENCE: 27
atgagcggcc gctcg                                                  15

<210> SEQ ID NO 28
<211> LENGTH: 28
<212> TYPE: DNA
<213> ORGANISM: Artificial sequence
<220> FEATURE:
<223> OTHER INFORMATION: Synthetic primer

<400> SEQUENCE: 28
ggcacggtgg gcatgtgtga gttttgtc                                    28

<210> SEQ ID NO 29
<211> LENGTH: 5
<212> TYPE: PRT
<213> ORGANISM: Artificial sequence
<220> FEATURE:
<223> OTHER INFORMATION: Synthetic peptide

<400> SEQUENCE: 29

Glu Leu Leu Gly Gly
1               5
```